(12) United States Patent
Lv et al.

(10) Patent No.: US 11,142,531 B2
(45) Date of Patent: Oct. 12, 2021

(54) CYANO SUBSTITUTED HETEROARYLPYRIMIDINONE DERIVATIVE, PREPARATION METHOD AND USE THEREOF

(71) Applicant: ZHEJIANG HISUN PHARMACEUTICAL CO., LTD., Zhejiang (CN)

(72) Inventors: Hejun Lv, Zhejiang (CN); Dongliang Guan, Zhejiang (CN); Mingxiao Chen, Zhejiang (CN); Jinglu Wang, Zhejiang (CN); Lin Qian, Zhejiang (CN)

(73) Assignee: ZHEJIANG HISUN PHARMACEUTICAL CO., LTD., Zhejiang (CN)

( * ) Notice: Subject to any disclaimer, the term of this patent is extended or adjusted under 35 U.S.C. 154(b) by 133 days.

(21) Appl. No.: 16/496,861

(22) PCT Filed: Mar. 23, 2018

(86) PCT No.: PCT/CN2018/080118
§ 371 (c)(1),
(2) Date: Sep. 23, 2019

(87) PCT Pub. No.: WO2018/171699
PCT Pub. Date: Sep. 27, 2018

(65) Prior Publication Data
US 2020/0102322 A1    Apr. 2, 2020

(30) Foreign Application Priority Data
Mar. 24, 2017  (CN) .................. 201710182808.X

(51) Int. Cl.
*C07D 495/04* (2006.01)

(52) U.S. Cl.
CPC .................................. *C07D 495/04* (2013.01)

(58) Field of Classification Search
CPC ..................................................... C07D 495/04
See application file for complete search history.

(56) References Cited

FOREIGN PATENT DOCUMENTS

| WO | 2013071169 A1 | 5/2013 |
| WO | 2014182943 A1 | 11/2014 |
| WO | 2014182945 A1 | 11/2014 |
| WO | 2014182950 A1 | 11/2014 |
| WO | 2016112305 A1 | 7/2016 |

OTHER PUBLICATIONS

Cancer and Metastasis Reviews (1998), 17(1), 91-106.*
Science (1999), vol. 286, 531-537.*
International Search Report for PCT/CN2018/080118 dated Jun. 29, 2018, ISA/CN.

* cited by examiner

*Primary Examiner* — Rebecca L Anderson
(74) *Attorney, Agent, or Firm* — Yue (Robert) Xu; Apex Attorneys at Law, LLP

(57) ABSTRACT

The present invention relates to a cyano-substituted heteroarylpyrimidinone derivative represented by formula (I), a preparation method therefor and a use thereof as a therapeutic agent, in particular a use as an acetyl-CoA carboxylase (ACC) inhibitor, and the definition of each substituent in formula (I) is the same as the definition in the description.

21 Claims, No Drawings

CYANO SUBSTITUTED HETEROARYLPYRIMIDINONE DERIVATIVE, PREPARATION METHOD AND USE THEREOF

CROSS REFERENCE TO RELATED APPLICATIONS

This application is the national phase of International Application No. PCT/CN2018/080118, titled "CYANO SUBSTITUTED HETEROARYLPYRIMIDINONE DERIVATIVE, PREPARATION METHOD AND USE THEREOF", filed on Mar. 23, 2018, which claims the priority of Chinese Patent Application No. 201710182808.X, titled "CYANO SUBSTITUTED HETEROARYLPYRIMIDINONE DERIVATIVE, PREPARATION METHOD AND USE THEREOF", filed on Mar. 24, 2017 with the China National Intellectual Property Administration, which is incorporated herein by reference in entirety.

FIELD

The present disclosure relates to a cyano-substituted heteroarylpyrimidinone derivative, a method for preparing the same, a pharmaceutical composition containing the derivative and a use thereof as a therapeutic agent, especially as an acetyl-CoA carboxylase (ACC) inhibitor.

BACKGROUND

Acetyl-CoA carboxylase (ACC) is one of the important proteins involved in fatty acid metabolism. It uses bitten as a coenzyme to catalyze the irreversible reaction of forming malonyl-CoA from acetyl-CoA, thereby providing a substrate for the subsequent synthesis of fatty acids or regulating fatty acid oxidation signals. This reaction is the first step of fatty acid metabolism and is a rate limiting step. The catalytic reaction can be divided into two steps, depending on the bitten carboxylase (BC) and carboxyltransferase (CT) activities of ACC, respectively.

There are two subtypes of ACC in human body, namely ACC1 and ACC2, which are separately encoded by two genes, ACACA and ACACB. They are different in tissue distribution and intracellular distribution. ACC1 is a cytosolic enzyme that is expressed at high levels in adipose synthesis tissue (such as fat and breast tissue). ACC2 is localized in the mitochondrial membrane and is mainly enriched in oxidization tissue (such as heart and skeletal muscle). Both are expressed at high levels in the liver. Therefore, ACC1 is mainly involved in the regulation of fatty acid synthesis, and ACC2 is mainly responsible for the regulation of the oxidation process of fatty acids. The activity of ACC is regulated by a variety of proteins, cytokines, endocrine hormones and receptors. Among them, AMPK is the main substance regulating ACC activity, and its activity can be inhibited by direct phosphorylation of ACC. Protein phosphorylase 2 can dephosphorylate ACC, thereby enhancing the effect of ACC. Under physiological conditions, free fatty acids synthesized in the cytosol are transported to the mitochondria via the carnitine palmitoyl-transferase 1 (CPT1) on the mitochondrial membrane for oxidative energy supply. Malonyl-CoA in the cytosol allosterically inhibits CPT1, leaving its activity at a lower level, thereby limiting fatty acid oxidation. When the body is under stress or the energy consumption increases, the AMPK pathway can be activated immediately, the downstream ACC is inactivated, and the level of malonyl-CoA is rapidly decreased, which further relieves the inhibition of CPT1, promotes the oxidation of fatty acids, and provides more adenosine triphosphate (ATP) for the body.

The fatty acid metabolic disorder caused by increase in fatty acid synthesis and impaired fatty acid oxidation is a common feature of various metabolic diseases, including diseases such as hepatic steatosis, dyslipidemia, obesity, metabolic syndrome, non-alcoholic steatohepatitis (NASH), type 2 diabetes (T2DM), and atherosclerosis. In addition, abnormal fatty acid metabolism is also one of the characteristics of tumor diseases, and participates in regulating the abnormal cell proliferation process of malignant tumors. Since ACC is a key regulatory protein of lipid metabolism, drug inhibition of ACC may stimulate the oxidation of fatty acids in oxidization tissues while limiting the synthesis of fatty acids in adipose-derived tissues, thereby providing an attractive method for the treatment of the above-mentioned abnormal lipid metabolism diseases.

At present, a series of ACC inhibitor patents have been published, including WO2014182943, WO2014182945, WO2014182950, etc. Currently, the drugs in clinical phase II are mainly GS-0976. However, the compounds disclosed in these conventional arts and the test drugs are still unsatisfactory in terms of effectiveness, safety or applicability. At present, the research on ACC inhibitors is far from enough. It is still necessary to research and develop new ACC inhibitors to meet the growing medical and health needs of people.

SUMMARY

Through experimental research, the inventor unexpectedly find that the compound of Formula (I) can effectively inhibit ACC.

Thus, in a first aspect, the present disclosure provides a new type of cyano-substituted heteroarylpyrimidinone derivative as shown in Formula (I):

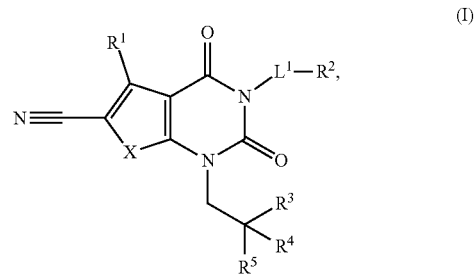

wherein,

X is selected from —NH—, —O— or —S—; preferably —S—;

$L^1$ is selected from alkylene, cycloalkylene or heterocyclylene;

$R^1$ is selected from hydrogen atom, alkyl, halogen, alkoxy or cyano, wherein the alkyl or alkoxy is optionally further substituted by one or more substituent groups selected from halogen, hydroxy, cyano, nitro, alkoxy, cycloalkyl, heterocyclyl, aryl, heteroaryl, —$NR^8R^9$, —$C(O)NR^8R^9$, —$C(O)R^6$, —$C(O)R^6$, —$S(O)_qNR^8R^9$, —$NR^8S(O)_2R^9$ or —$NR^8C(O)R^9$;

$R^2$ is selected from hydrogen atom, hydroxy, halogen, nitro, cyano, alkyl, alkoxy, cycloalkyl, heterocyclyl, aryl, heteroaryl, —$NR^8R^9$, —$C(O)NR^8R^9$, —$C(O)R^6$, —OC(O)

$R^6$, —S(O)$_q$NR$^8$R$^9$, —NR$^8$S(O)$_2$R$^9$ or —NR$^8$C(O)R$^9$, wherein the alkyl, alkoxy, cycloalkyl, heterocyclyl, aryl or heteroaryl is optionally further substituted by one or more substituent groups selected from hydroxy, halogen, nitro, cyano, alkyl, alkoxy, cycloalkyl, heterocyclyl, aryl, heteroaryl, —NR$^{10}$R$^{11}$, —C(O)NR$^{10}$R$^{11}$, —C(O)R$^{12}$, —C(O)OR$^{12}$ or —NR$^{10}$C(O)R$^{11}$;

$R^3$ is selected from aryl or heteroaryl, wherein the aryl or heteroaryl is optionally further substituted by one or more substituent groups selected from R$^7$;

$R^4$ and $R^5$ are each independently selected from hydrogen atom, alkyl, —OR$^6$, —SR$^6$, —NR$^8$R$^9$, —C(O)NR$^8$R$^9$, —C(O)R$^6$, —C(O)R$^6$, —S(O)$_q$NR$^8$R$^9$, —NR S(O)$_2$R$^9$ or —NR$^8$C(O)R$^9$;

or, $R^4$ and $R^5$, together with the atom to which they are attached, form a C$_{3-8}$ saturated or partly unsaturated cycloalkyl, or form a C$_{4-8}$ saturated or partly unsaturated heterocyclyl having one or more heteroatoms selected from N, O and S(O)q, wherein the cycloalkyl or heterocyclyl is optionally further substituted by one or more substituent groups selected from hydroxy, halogen, nitro, cyano, alkyl, alkoxy, cycloalkyl, heterocyclyl, aryl, heteroaryl, —NR$^8$R$^9$, —C(O)NR$^8$R$^9$, —C(O)R$^6$, —C(O)R$^6$, —S(O)$_q$NR$^8$R$^9$, —NR$^8$S(O)$_2$R$^9$ or —NR$^8$C(O)R$^9$;

$R^7$ is each independently selected from hydrogen atom, hydroxy, halogen, cyano, nitro, alkyl, alkoxy, cycloalkyl, heterocyclyl, aryl, heteroaryl, —NR$^8$R$^9$, —C(O)NR$^8$R$^9$, —C(O)R$^6$, —OC(O)R$^6$, —S(O)$_q$NR$^8$R$^9$, —NR$^8$S(O)$_2$R$^9$ or —NR$^8$C(O)R$^9$, wherein the alkyl, alkoxy, cycloalkyl, heterocyclyl, aryl or heteroaryl is optionally further substituted by a substituent group selected from hydroxy, halogen, nitro, cyano, alkyl, alkoxy, cycloalkyl, heterocyclyl, aryl, heteroaryl, —NR$^8$R$^9$, —C(O)NR$^8$R$^9$, —C(O)R$^6$, —C(O)R$^6$, —S(O)$_q$NR$^8$R$^9$, —NR S(O)$_2$R or —NR$^9$C(O)R$^9$;

$R^6$, $R^8$ and $R^9$ are each independently selected from hydrogen atom, alkyl, —OR$^{12}$, cyano, hydroxy, halogen, cycloalkyl, heterocyclyl, aryl or heteroaryl, wherein the alkyl, cycloalkyl, heterocyclyl, aryl or heteroaryl is optionally further substituted by one or more substituent groups selected from hydroxy, halogen, nitro, cyano, alkyl, alkoxy, cycloalkyl, heterocyclyl, aryl, heteroaryl, —NR$^{10}$R$^{11}$, —C(O)NR$^{10}$R$^{11}$, —C(O)R$_{12}$, —C(O)OR$^{12}$ or —NR$^{10}$C(O)R$^{11}$, or, $R^8$ and $R^9$, together with the N atom to which they are attached, form a C$_{4-8}$ heterocyclyl, wherein the C$_{4-8}$ heterocycle comprises one or more atoms selected from N, O and S(O)$_q$, and the C$_{4-8}$ heterocycle is optionally further substituted by one or more substituent groups selected from hydroxy, halogen, nitro, cyano, alkyl, alkoxy, cycloalkyl, heterocyclyl, aryl, heteroaryl, =O, —NR$^{10}$R$^{11}$, —C(O)NR$^{10}$R$^{11}$, —C(O)R$^{12}$, —C(O)OR$^{12}$ or —NR$^{10}$(O)R$^{11}$, $R^{10}$, $R^{11}$ and $R^{12}$ are each independently selected from hydrogen atom, alkyl, alkenyl, cycloalkyl, heterocyclyl, aryl or heteroaryl, wherein the alkyl, cycloalkyl, heterocyclyl, aryl or heteroaryl is optionally further substituted by one or more substituent groups selected from hydroxy, halogen, nitro, cyano, alkyl, alkoxy, cycloalkyl, heterocyclyl, aryl, heteroaryl, carboxylic acid or carboxylic ester; and q is 0, 1 or 2.

In this article, the compound of Formula (I) (and the compound of Formula (II) to (IV), the compound of Formula IA, etc.) also comprises the stereoisomers, tautomers or pharmaceutically acceptable salts thereof.

In some preferred embodiments of the present disclosure, the compound of Formula (I) has a structure of Formula (II):

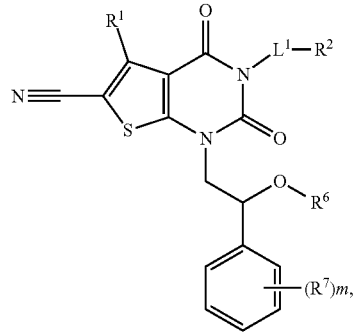

wherein, m is 1, 2, 3, 4 or 5; and $L^1$, $R^1$, $R^2$, $R^6$ and $R^7$ are as defined in Formula (I).

In some preferred embodiments of the present disclosure, the compound of Formula (II) has a structure of Formula (III):

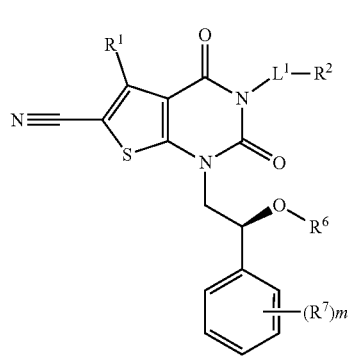

wherein, m is 1, 2, 3, 4 or 5; and $L^1$, $R^1$, $R^2$, $R^6$ and $R^7$ are as defined in Formula (I).

In some preferred embodiments of the present disclosure, the compound of Formula (II) has a structure of Formula (IV):

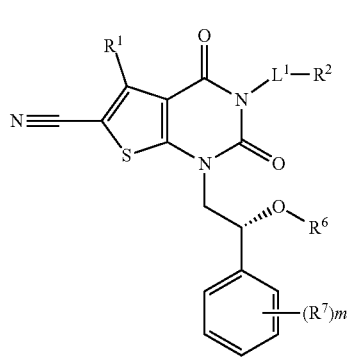

wherein, m is 1, 2, 3, 4 or 5; and $L^1$, $R^1$, $R^2$, $R^6$ and $R^7$ are as defined in Formula (I).

In some preferred embodiments of the present disclosure, the compounds as shown in Formula (I), (II), (III) or (IV) are provided, wherein $R^1$ is selected from methyl or trifluoromethyl.

In some preferred embodiments of the present disclosure, the compounds as shown in Formula (I), (II), (III) or (IV) are provided, wherein:

$R^2$ is selected from tetrazolyl, —C(O)OR$^{12}$ or —C(O)NR$^8$R$^9$;

$R^8$ is selected from hydrogen atom or alkyl;

$R^9$ is selected from cyano or —OR$^{12}$; and $R^{12}$ is selected from hydrogen atom, alkyl, alkenyl, cycloalkyl, heterocyclyl, aryl or heteroaryl, wherein the alkyl, cycloalkyl, heterocyclyl, aryl or heteroaryl is optionally further substituted by one or more substituent groups selected from hydroxy, halogen, nitro, cyano, alkyl, alkoxy, cycloalkyl, heterocyclyl, aryl, heteroaryl, carboxylic acid or carboxylic ester.

In some preferred embodiments of the present disclosure, the compounds as shown in Formula (I), (II), (III) or (IV) are provided, wherein $L^1$ is —C(O)OH.

In some preferred embodiments of the present disclosure, the compounds as shown in Formula (I), (II), (III) or (IV) are provided, wherein $L^1$ is:

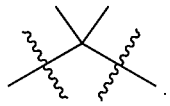

In some preferred embodiments of the present disclosure, the compounds as shown in Formula (I), (II), (III) or (IV) are provided, wherein $R^6$ is selected from tetrahydropyranyl.

In some preferred embodiments of the present disclosure, the compounds as shown in Formula (I), (II), (III) or (IV) are provided, wherein $R^7$ is selected from alkoxy or halogen, wherein the alkoxy is optionally further substituted by halogen or cycloalkyl; and $R^7$ is preferably methoxy, ethoxy, fluoro, trifluoromethyl, difluoromethoxy, fluoroethoxy or cyclopropyl methoxy.

The typical compounds of the present disclosure include, but are not limited to:

| Example No. | Structure | Name |
|---|---|---|
| 1 | 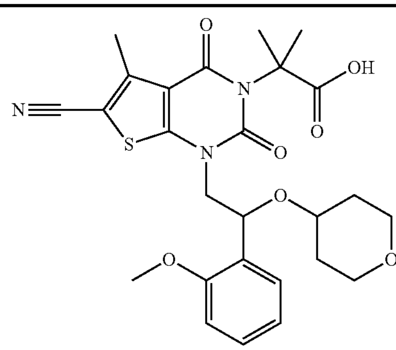 | 2-(6-Cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid |
| 2 | 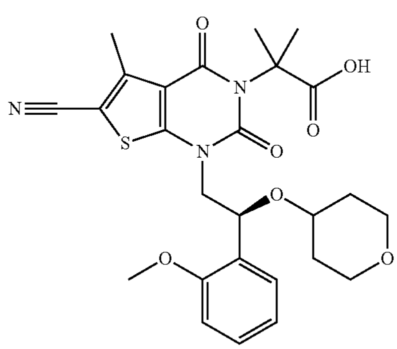 | (S)-2-(6-cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid |
| 3 | 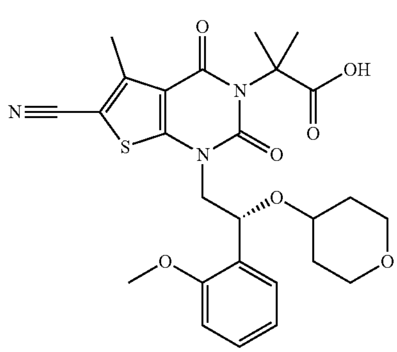 [SMILES: COc1ccccc1C(Cn1c(=O)n(C(C)(C)C(=O)O)c(=O)c2c(C)c(C#N)sc21)OC1CCOCC1] | (R)-2-(6-cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid |

| Example No. | Structure | Name |
|---|---|---|
| 4 | 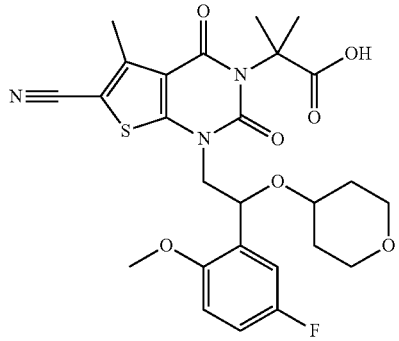 | 2-(6-Cyano-1-(2-(5-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid |
| 5 | 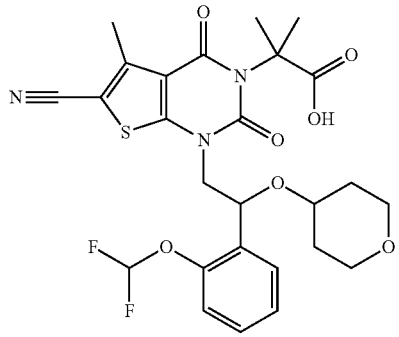 [SMILES: Cc1c(C#N)sc2c1c(=O)n(C(C)(C)C(=O)O)c(=O)n2CC(OC1CCOCC1)c1ccccc1OC(F)F] | 2-(6-Cyano-1-(2-(2-(difluoromethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid |
| 6 | 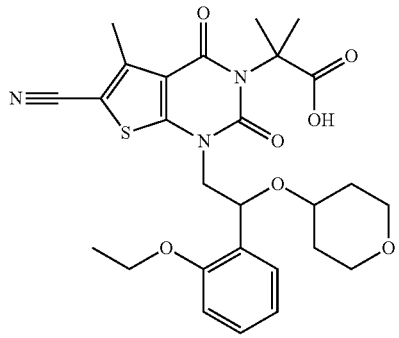 [SMILES: CCOc1ccccc1C(Cn1c(=O)n(C(C)(C)C(=O)O)c(=O)c2c(C)c(C#N)sc21)OC1CCOCC1] | 2-(6-Cyano-1-(2-(2-ethoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid |
| 7 | 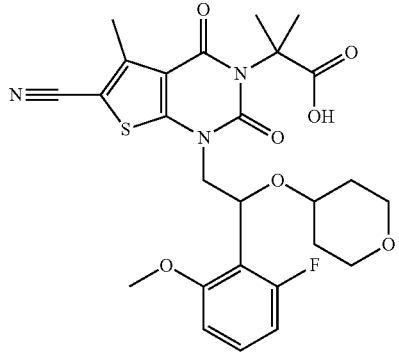 [SMILES: COc1cccc(F)c1C(Cn1c(=O)n(C(C)(C)C(=O)O)c(=O)c2c(C)c(C#N)sc21)OC1CCOCC1] | 2-(6-Cyano-1-(2-(2-fluoro-6-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid |

-continued

| Example No. | Structure | Name |
|---|---|---|
| 8 | 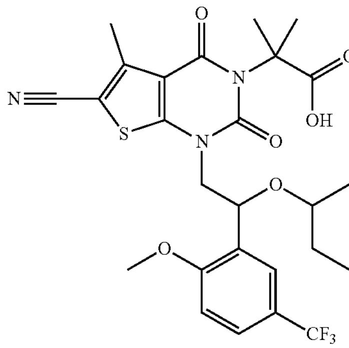 | 2-(6-Cyano-1-(2-(2-methoxy-5-(trifluoromethyl)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid |
| 9 | 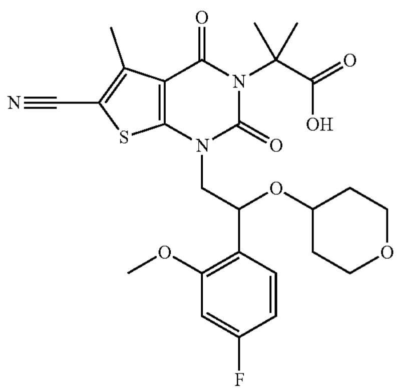 [SMILES: COc1cc(F)ccc1C(Cn1c(=O)n(C(C)(C)C(=O)O)c(=O)c2c(C)c(C#N)sc21)OC1CCOCC1] | 2-(6-Cyano-1-(2-(4-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid |
| 10 | 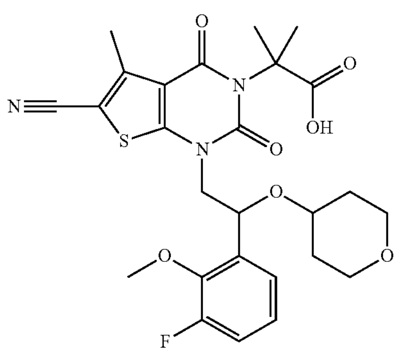 [SMILES: COc1c(F)cccc1C(Cn1c(=O)n(C(C)(C)C(=O)O)c(=O)c2c(C)c(C#N)sc21)OC1CCOCC1] | 2-(6-Cyano-1-(2-(3-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid |
| 11 | 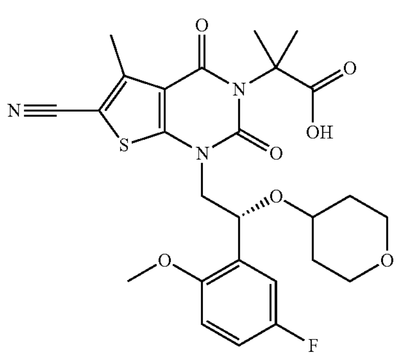 [SMILES: COc1ccc(F)cc1[C@H](Cn1c(=O)n(C(C)(C)C(=O)O)c(=O)c2c(C)c(C#N)sc21)OC1CCOCC1] | (R)-2-(6-cyano-1-(2-(5-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid |

-continued

| Example No. | Structure | Name |
|---|---|---|
| 12 | 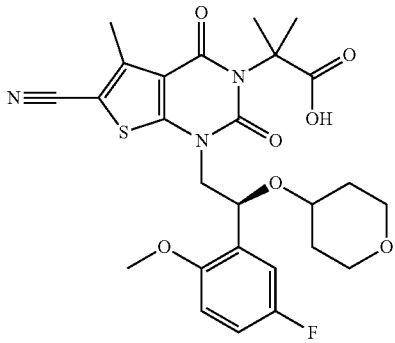 [SMILES: COc1ccc(F)cc1[C@@H](Cn1c(=O)n(C(C)(C)C(=O)O)c(=O)c2c(C)c(C#N)sc21)OC1CCOCC1] | (S)-2-(6-cyano-1-(2-(5-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid |
| 13 | 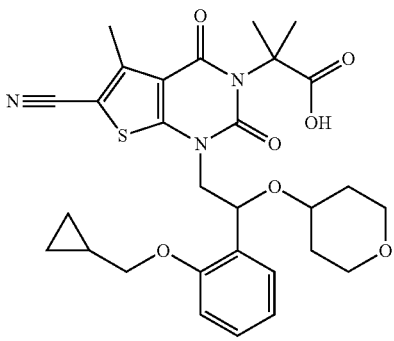 [SMILES: Cc1c(C#N)sc2c1c(=O)n(C(C)(C)C(=O)O)c(=O)n2CC(OC1CCOCC1)c1ccccc1OCC1CC1] | 2-(6-Cyano-1-(2-(2-(cyclopropylmethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid |
| 14 | 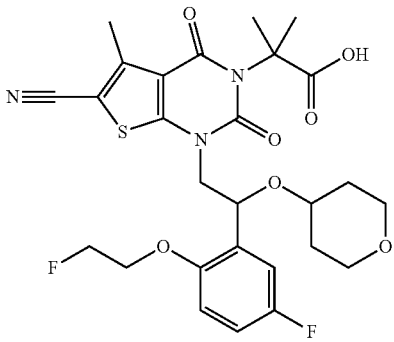 [SMILES: Cc1c(C#N)sc2c1c(=O)n(C(C)(C)C(=O)O)c(=O)n2CC(OC1CCOCC1)c1cc(F)ccc1OCCF] | 2-(6-Cyano-1-(2-(5-fluoro-2-(2-fluoroethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid |
| 15 | 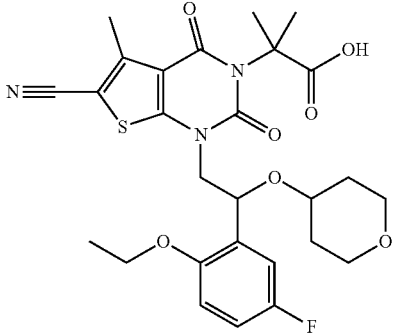 [SMILES: CCOc1ccc(F)cc1C(Cn1c(=O)n(C(C)(C)C(=O)O)c(=O)c2c(C)c(C#N)sc21)OC1CCOCC1] | 2-(6-Cyano-1-(2-(2-ethoxy-5-fluorophenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid |

| Example No. | Structure | Name |
|---|---|---|
| 16 | 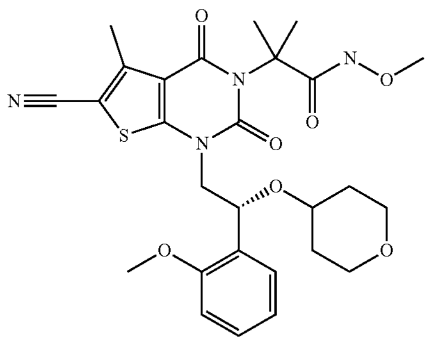 [SMILES: CONC(=O)C(C)(C)n1c(=O)c2c(C)c(C#N)sc2n(C[C@H](OC2CCOCC2)c2ccccc2OC)c1=O] | (R)-2-(6-cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-N-methoxy-2-methyl-propanamide |
| 17 | 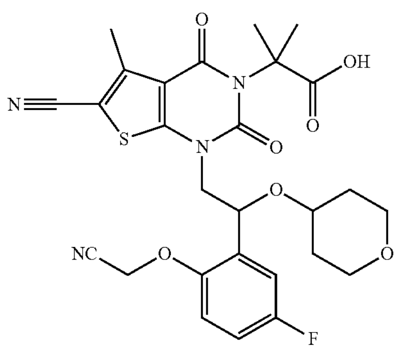 [SMILES: Cc1c(C#N)sc2c1c(=O)n(C(C)(C)C(=O)O)c(=O)n2CC(OC1CCOCC1)c1cc(F)ccc1OCC#N] | 2-(6-Cyano-1-(2-(2-(cyanomethoxy)-5-fluorophenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid |
| 18 | 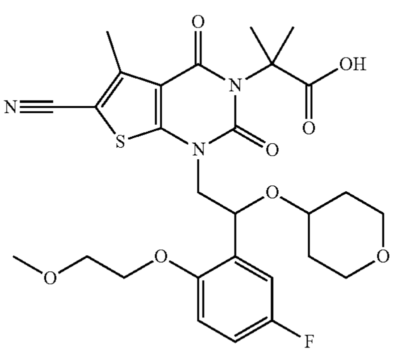 [SMILES: COCCOc1ccc(F)cc1C(Cn1c(=O)n(C(C)(C)C(=O)O)c(=O)c2c(C)c(C#N)sc21)OC1CCOCC1] | 2-(6-Cyano-1-(2-(5-fluoro-2-(2-methoxyethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methyl-propionic acid |
| 19 | 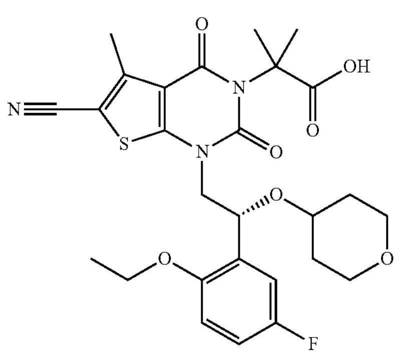 [SMILES: CCOc1ccc(F)cc1[C@H](Cn1c(=O)n(C(C)(C)C(=O)O)c(=O)c2c(C)c(C#N)sc21)OC1CCOCC1] | (R)-2-(6-cyano-1-(2-(2-ethoxy-5-fluoro-phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid |

| Example No. | Structure | Name |
|---|---|---|
| 20 | 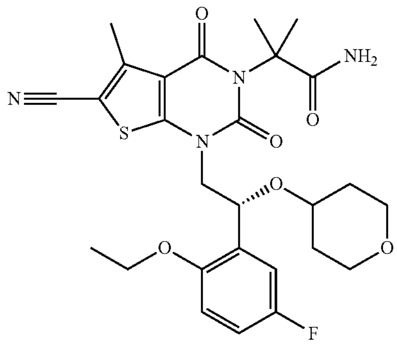 | (R)-2-(6-cyano-1-(2-(2-ethoxy-5-fluorophenyl)-2-((tetra-hydro-2H-pyran-4-yl)oxy)ethyl)-5-methyl-2,4-dioxo-1,2-di-hydrothiopheno[2,3-d]pyrimidin-3(4H)-yl)-2-methylpropanamide |
| 21 | 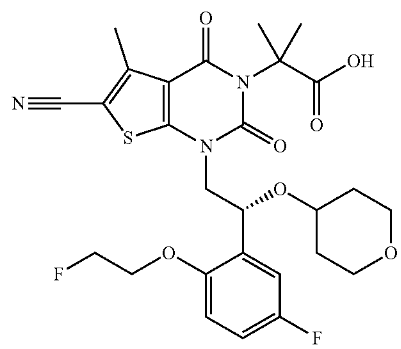 [SMILES: Cc1c(C#N)sc2c1c(=O)n(C(C)(C)C(=O)O)c(=O)n2C[C@H](OC1CCOCC1)c1cc(F)ccc1OCCF] | (R)-2-(6-cyano-1-(2-(5-fluoro-2-(2-fluoroethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methyl-propionic acid |

The typical compounds comprises the stereoisomers, tautomers or pharmaceutically acceptable salts thereof.

Further, the present disclosure provides a method for preparing the compound of Formula (I), comprising:

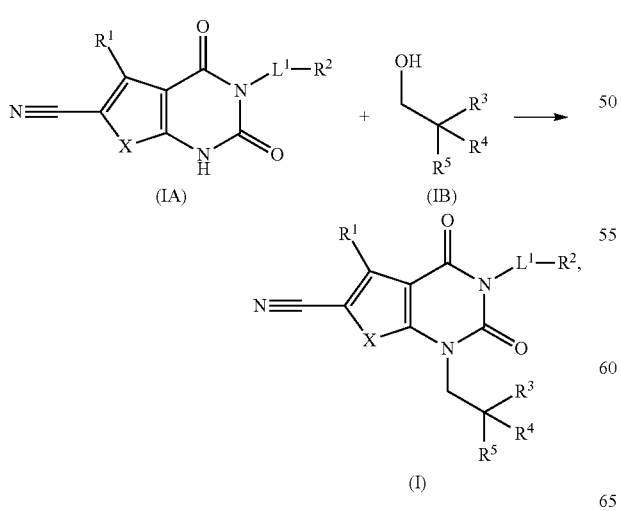

reacting a compound of Formula (IA) with a compound of Formula (IB) or a salt thereof in the presence of triphenylphosphine and diisopropyl azodicarboxylate, optionally further performing esterolysis, or optionally further reacting with $NHR^8R^9$ or a salt thereof, to obtain the compound of Formula (1);

wherein X, $L^1$, $R^1$-$R^5$, $R^8$ and $R^9$ are as defined in Formula (I); and $R^2$ is preferably —C(O)OH or —C(O)$NR^8R^9$.

The present disclosure further provides a compound as shown in Formula (IA)

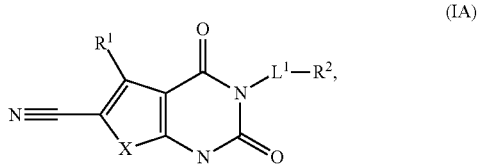

wherein X, $L^1$, $R^1$ and $R^2$ are as defined in Formula (I).

The typical compounds of Formula (IA) include, but are not limited to the following compound I1:

| Intermediate No. | Structure | Name |
|---|---|---|
| 11 | 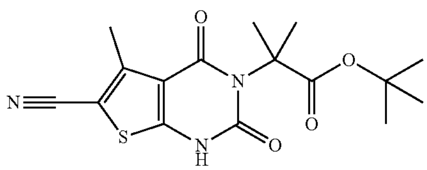 | tert-butyl 2-(6-cyano-5-methyl-2,4-dioxo-1,2-dihydrothieno[2,3-d]pyrimidin-3(4H)-yl)-2-methylpropionate 11 |

The present disclosure further provides a method for preparing the compound of
Formula (IA), comprising,

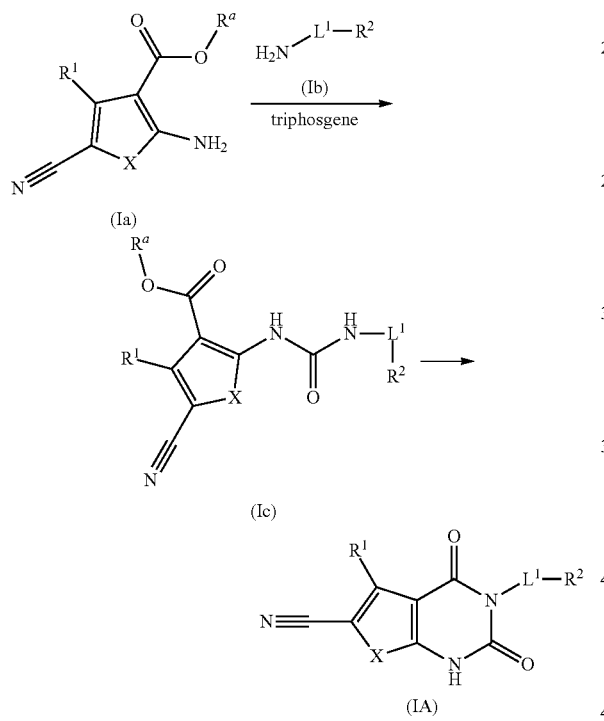

reacting a compound of Formula (Ia) and a compound of Formula (Ib) in the presence of triphosgene under alkaline conditions in ice bath, to obtain a compound of Formula (Ic); reacting the compound of Formula (Ic) under alkaline conditions to obtain the compound of Formula (IA);
wherein
$R^a$ is selected from alkyl; and
X, $L^1$, $R^1$ and $R^2$ are defined as in Formula (I).

In the above preparation method, the alkaline condition is provided by an organic base or an inorganic base. The organic base is selected from diisopropylethylamine, pyridine, triethylamine, piperidine, N-methylpiperazine, 4-dimethylaminopyridine or potassium tert-butoxide, preferably diisopropylethylamine, triethylamine or potassium tert-butoxide; and the inorganic base is selected from sodium carbonate, potassium carbonate, cesium carbonate, sodium hydride, sodium hydroxide, potassium hydroxide, lithium hydroxide or potassium hydride, preferably triethylamine or sodium hydride.

In another aspect, the present disclosure provides a pharmaceutical composition, which comprises an effective amount of the compound as shown in Formula (I) (including forms of stereoisomers, tautomers or pharmaceutically acceptable salts thereof), and optionally pharmaceutically acceptable carrier, excipient or a combination thereof.

In another aspect, the present disclosure provides a method for inhibiting ACC, comprising contacting ACC with the compound of Formula (I) or the pharmaceutical composition thereof in the present disclosure. The present disclosure further provides a method for preventing or treating ACC-related diseases or conditions, comprising administering the compound or the pharmaceutical composition according to Formula (I) to a subject in need thereof.

In another aspect, the present disclosure provides use of the compound of Formula (I) or the pharmaceutical composition thereof in the manufacture of a medicament as an ACC inhibitor.

The present disclosure further provides use of the compound of Formula (I) and the pharmaceutical composition thereof in the manufacture of a medicament for preventing or treating ACC related diseases or conditions, wherein the diseases or conditions are preferably metabolic diseases, cancer, fungus, parasitic or bacterial infection; wherein the metabolic diseases are preferably hepatic steatosis, non-alcoholic fatty liver disease, obesity, dyslipidemia, hyperlipidemia, type II diabetes or metabolic syndrome, wherein the obesity is preferably Prader-Willi syndrome, Bardet-Biedl syndrome, Cohen syndrome or MOMO syndrome, wherein the cancer is preferably hepatocellular carcinoma, non-small cell lung cancer, small cell lung cancer, gastric cancer, colorectal cancer, head and neck tumor, melanoma, ovarian cancer or cervical cancer, more preferably hepatocellular carcinoma and non-small cell lung cancer.

DETAILED DESCRIPTION OF THE DISCLOSURE

Unless otherwise stated, some of the terms used in the specification and claims of the present disclosure are defined as follows.

"Alkyl", as a group or part of a group, represents for straight or branched $C_1$-$C_{20}$ aliphatic hydrocarbon groups, preferably $C_1$-$C_{10}$ alkyl, more preferably $C_1$-$C_6$ alkyl, and especially preferably $C_1$-$C_4$ alkyl. Examples of alkyl groups include, but are not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, etc. Alkyl may be substituted or unsubstituted.

"Alkylene" is a divalent alkyl group, preferably $C_1$-$C_{10}$ alkylene, more preferably $C_1$-$C_6$ alkylene, especially preferably $C_1$-$C_4$ alkylene. Examples of alkylene groups include, but are not limited to methylene, ethylene,

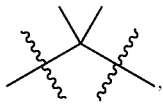

n-propylene, etc. Alkylene may be substituted or unsubstituted.

"Alkenyl" represents for an alkyl group as defined above composed of at least two carbon atoms and at least one carbon-carbon double bond. Typical examples include, but are not limited to vinyl, 1-propenyl, 2-propenyl, 1-, 2- or 3-butenyl, etc., preferably $C_2$-$C_4$ alkenyl. Alkenyl may be optionally substituted or unsubstituted.

"Alkynyl", as a group or part of a group, represents for straight or branched aliphatic hydrocarbon groups including a carbon-carbon triple bond, preferably $C_2$-$C_{10}$ alkynyl, more preferably $C_2$-$C_6$ alkynyl, most preferably $C_2$-$C_4$ alkynyl. Examples of alkynyl groups inlcude, but are not limited to ethynyl, 1-propynyl, 2-propynyl, 1-, 2- or 3-butynyl, etc. Alkynyl may be substituted or unsubstituted.

"Cycloalkyl" represents for saturated or partly saturated carbon rings of monocyclic rings, fused rings, bridged rings or spiro rings, preferably $C_3$-$C_{12}$ cycloalkyl, more preferably $C_3$-$C_8$ cycloalkyl, most preferably $C_3$-$C_6$ cycloalkyl. Examples of monocyclic ring cycloalkyl include, but are not limited to cyclopropyl, cyclobutyl, cyclopentyl, cyclopentenyl, cyclohexyl, cyclohexenyl, cyclohexadienyl, cycloheptyl, cycloheptatrienyl, cyclooctyl, etc. preferably cyclopropyl and cyclohexenyl.

"Cycloalkylene" is a divalent cycloalkyl, preferably $C_3$-$C_{12}$ cycloalkylene, more preferably $C_3$-$C_8$ cycloalkylene, and most preferably $C_3$-$C_6$ cycloalkylene. Examples of cycloalkylene include, but are not limited to cyclopropylidene, cyclobutylidene, cyclopentylidene, etc. Cycloalkylene may be substituted or unsubstituted.

"Cyclopropylidene" represents for

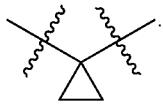

"Cyclobutylidene" represents for

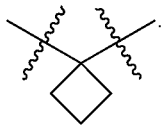 [SMILES: *C1(*)CCC1]

"Spiro cycloalkyl" represents for a 5 to 18 membered polycyclic group, having two or more than two ring structures and sharing one carbon atom between monocyclic rings (called a spiro atom). There may be one or more double bonds in the rings, but none of the rings has an aromatic system having fully conjugated π electrons. The spiro cycloalkyl is preferably 6 to 14 membered, and more preferably 7 to 10 membered. According to the number of the common spiro atoms between rings, the spiro cycloalkyl are classified into monospiro, bi-spiro and poly-spiro cycloalkyl, preferably monospiro and bi-spiro cycloalkyl, preferably 4 membered/5 membered, 4 membered/6 membered, 5 membered/5 membered or 5 membered/6 membered. Non-limiting examples of "spiro cycloalkyl" include, but are not limited to spiro[4.5]decyl, spiro[4.4]nonyl, spiro[3.5]nonyl, and spiro[2.4]heptyl.

"Fused cycloalkyl" represents for a 5 to 18 membered all-carbon polycyclic group, having two or more ring structures which share a pair of carbon atoms, wherein one or more rings may have one or more double bonds, but none of the rings has an aromatic system having fully conjugated π electrons. The fused cycloalkyl is preferably 6 to 12 membered, more preferably 7 to 10 membered. According to the number of rings, the fused cycloalkyl may be classified into bicyclic, tricyclic, pyridone or polycyclic fused cycloalkyl, preferably bicyclic or tricyclic, and more preferably 5 membered/5 membered or 5 membered/6 membered bicycloalkyl group. The unlimited examples of "fused cycloalkyl" include, but are not limited to bicyclo[3.1.0]hexyl, bicyclo[3.2.0]hept-1-enyl, bicyclo[3.2.0]heptyl, decahydronaphthyl or tetradecahydrophenanthrenyl.

"Bridged cycloalkyl" represents for a 5 to 18 membered all-carbon polycyclic group, having two or more ring structures which share two non-directly bonded carbon atoms, wherein one or more rings may have one or more double bonds, but none of the rings has an aromatic system having fully conjugated π electrons. The bridged cycloalkyl is preferably 6 to 14 membered, more preferably 7 to 10 membered. According to the number of rings, the bridged cycloalkyl may be classified into bicyclic, tricyclic, pyridone or polycyclic bridged cycloalkyl, preferably bicyclic, tricyclic or pyridone, and more preferably bicyclic or tricyclic. The unlimited examples of "bridged cycloalkyl" include, but are not limited to (1s,4s)-bicyclo[2.2.1]heptyl, bicyclo[3.2.1]octyl, (1s,5s)-bicyclo[3.3.1]nonyl, bicyclo[2.2.2]octyl, and (1r,5r -bicyclo[3.3.2]decyl.

The cycloalkyl rings may be fused on an aryl, a heteroaryl or a heterocyclyl ring, wherein the rings to which the parent structure is attached are cycloalkyl. The unlimited examples include indanyl, tetrahydronaphthyl, benzocycloheptyl, etc. The cycloalkyl may be optionally substituted or unsubstituted.

"Heterocyclyl", "heterocycle" or "heterocyclic" are used interchangeable herein, and they all represent for non-aromatic heterocyclyl, wherein one or more of the ring-forming atoms are heteroatoms such as oxygen, nitrogen, sulfur atoms, etc., including monocyclic ring, fused ring, bridged ring and spiro ring. Heterocyclyl is preferably 5 to 7 membered monocyclic ring or 7 to 10 membered bicyclic or tricyclic ring, which may contain 1, 2 or 3 atoms selected from nitrogen, oxygen and/or sulfur. Examples of "heterocyclyl" include, but are not limited to morpholinyl, oxetanyl, thiomorpholinyl, tetrahydropyranyl, 1,1-dioxo-thiomorpholinyl, piperidinyl, 2-oxo-piperidinyl, pyrrolidinyl, 2-oxo-pyrrolidinyl, piperazin-2-one, 8-oxa-3-aza-bicyclo[3.2.1]octyl and piperazinyl. Heterocyclyl may be substituted or unsubstituted.

"Spiro heterocyclyl" represents for a 5 to 18 membered polycyclic group, having two or more than two ring structures and sharing one carbon atom between monocyclic rings. There may be one or more double bonds in the rings, but none of the rings has an aromatic system having fully conjugated π electrons, wherein one or more ring atoms are heteroatoms selected from nitrogen, oxygen or $S(O)_q$ (wherein q is selected from 0, 1 or 2), and the other ring atoms are carbon. The spiro heterocyclyl is preferably 6 to 14 membered, and more preferably 7 to 10 membered. According to the number of the common Spiro atoms between rings, the spiro heterocyclyl are classified into monospiro heterocyclyl, bi-spiro heterocyclyl and polyspiro heterocyclyl, preferably monospiro heterocyclyl and bi-spiro heterocyclyl, more preferably 4 membered/4 membered, 4 membered/5 membered, 4 membered/6 membered, 5 membered/5 membered or 5 membered/6 membered monospiro heterocyclyl. Non-limiting examples of "spiro heterocyclyl" include, but are not limited to 1,7-dioxaspiro[4.5]decyl, 2-oxa-7-azaspiro[4.4]nonyl, 7-oxaspiro[3.5]nonyl and 5-oxaspiro[2.4]heptyl.

"Fused heterocyclyl" represents for an all-carbon polycyclic group, having two or more ring structures which share a pair of atoms, wherein one or more rings may have one or more double bonds, but none of the rings has an aromatic system having fully conjugated π electrons, wherein one or more ring atoms are heteroatoms selected from nitrogen, oxygen or $S(O)_q$ (wherein q is selected from 0, 1 or 2), and the other ring atoms are carbon. The fused heterocyclyl is preferably 6 to 14 membered, more preferably 7 to 10 membered. According to the number of rings, the fused heterocyclyl may be classified into bicyclic, tricyclic, pyridone or polycyclic fused heterocyclyl, preferably bicyclic or tricyclic, and more preferably 5 membered/5 membered or 5 membered/6 membered bicyclic fused heterocyclyl. The unlimited examples of "fused heterocyclyl" include, but are not limited to octahydropyrrolo[3,4-c]pyrrolyl, octahydro-1H-isoindolyl, 3-azabicyclo[3.1.0]hexyl, octahydrobenzo[b][1,4]dioxine.

"Bridged heterocyclyl" represents for a 5 to 18 membered, preferably 5 to 14 membered polycyclic group, having two or more ring structures which share two non-directly bonded atoms, wherein one or more rings may have one or more double bonds, but none of the rings has an aromatic system having fully conjugated π electrons, wherein one or more ring atoms are heteroatoms selected from nitrogen, oxygen or $S(O)_q$ (wherein q is selected from 0, 1 or 2), and the other ring atoms are carbon. The bridged heterocyclyl is preferably 6 to 14 membered, more preferably 7 to 12 membered. According to the number of rings, the bridged heterocyclyl may be classified into bicyclic, tricyclic, pyridone or polycyclic bridged heterocyclyl, preferably bicyclic, tricyclic or pyridone, and more preferably bicyclic or tricyclic. The unlimited examples of "bridged heterocyclyl" include, but are not limited to 2-azabicyclo[2.2.1]heptyl, 2-azabicyclo[2.2.2]octyl and 2-azabicyclo[3.3.2]decyl. The heterocyclyl rings may be fused on aryl, heteroaryl or cycloalkyl rings, wherein the rings to which the parent structure is attached are heterocyclyl. The heterocyclyl may be optional substituted or unsubstituted.

"Heterocyclylene" represents for divalent heterocyclyl, preferably 5 to 7 membered monocyclic heterocyclylene or 7 to 10 membered bicyclic heterocyclyl or tricyclic heterocyclylene, which may comprise 1, 2 or 3 atoms selected from nitrogen, oxygen and/or sulfur. Heterocyclylene may be substituted or unsubstituted.

"Aryl" represents for carbocyclic aromatic system containing one or two rings, wherein the rings may be joined together in a fused manner. The term "aryl" includes aromatic groups such as phenyl, naphthyl and tetrahydronaphthyl. Preferably, the aryl is a $C_6$-$C_{10}$ aryl group, and more preferably the aryl is a phenyl and naphthyl, and most preferably a phenyl. Aryl may be substituted or unsubstituted. The "alkyl" may be fused to heteroaryl, heterocyclyl or cycloalkyl, wherein aryl ring is attached to the parent structure. The unlimited examples include, but are not limited to

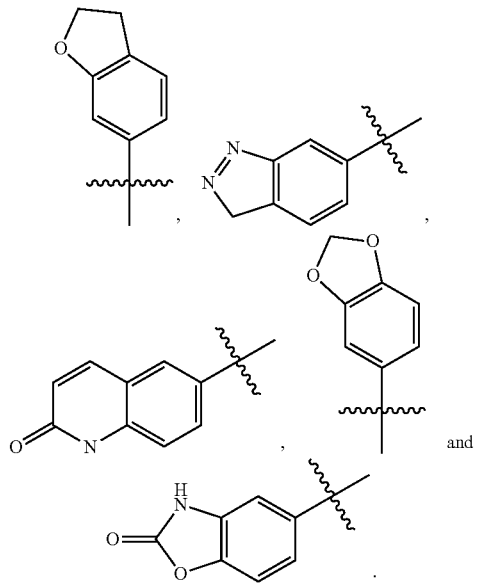

"Heteroaryl" represents for an aromatic 5 to 6 membered monocyclic or 9 to 10 membered bicyclic ring, which may contain 1 to 4 atoms selected from nitrogen, oxygen and/or sulfur. Examples of "heteroaryl" include, but are not limited to furyl, pyridyl, 2-oxo-1,2-dihydropyridyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzodioxolyl, benzimidazolyl, indolyl, isoindolyl, 1,3-dioxo-isoindolyl, quinolinyl, indazolyl, benzoisothiazolyl, benzoxazolyl and benzoisoxazolyl. Heteroaryl may be substituted or unsubstituted. The heteroaryl ring may be fused on aryl, heterocyclyl or cycloalkyl rings, wherein the rings to which the parent structure is attached are heteroaryl rings. The unlimited examples include, but are not limited to

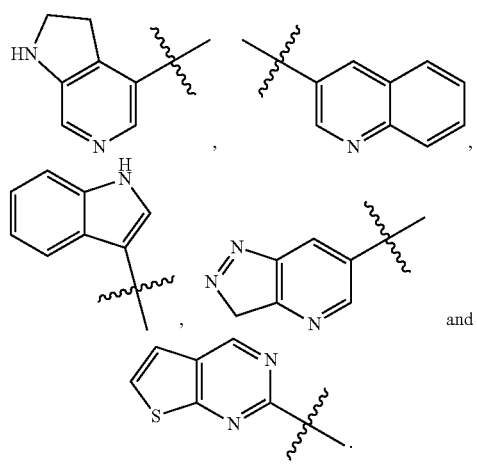

"Alkoxy" represents for alkyl-O— groups, wherein alkyl is as defined in this text. $C_1$-$C_6$ alkoxy is preferred, and $C_1$-$C_4$ alkoxy is particularly preferred. Examples thereof include, but are not limited to methoxy, ethoxy, n-propoxy, isopropoxy, n-butoxy, isobutoxy, tert-butoxy, etc.

"hydroxy" represents for —OH group.

"Halogen" represents for fluorine, chlorine, bromine and iodine, preferably fluorine, chlorine and bromine.

"Amino" represents for —$NH_2$.

"Cyano" represents for —CN.

"Nitro" represents for —$NO_2$.

"Benzyl" represents for —$CH_2$-phenyl.

"Carboxyl" represents for —C(O)OH.

"Carboxylic ester group" represents for —C(O)O(alkyl) or (cycloalkyl), wherein alkyl and cycloalkyl are defined as above.

"DMSO" represents for dimethyl sulfoxide.

"Sulfhydryl group" represents for —SH.

"Substituted" indicates that one or more (preferably at most 5, and more preferably 1-3 hydrogen atoms) hydrogen atoms are independently substituted by corresponding numbers of substituents. It is obvious that the substituents are only in their possible chemical positions, and those skilled in the art may determine (through experiments or theory) substitutions that may or may not be exist without overmuch efforts. For example, an amino or a hydroxy having a free hydrogen may be unstable when bonding with carbon atoms having an unsaturated (such as olefinic) bond.

In the present disclosure, the "substitution" or "substituted", unless otherwise indicated, all indicate that the groups may be substituted by one or more groups selected from alkyl, alkenyl, alkynyl, alkoxy, alkylthio, alkylamino, halogen, sulfhydryl, hydroxy, nitro, cyano, cycloalkyl, heterocyclyl, aryl, heteroaryl, cycloalkoxy, heterocycloalkoxy, cycloalkylthio, heterocycloalkylthio, amino, halogenated alkyl, hydroxyalkyl, carboxyl, carboxylic ester group, =O, —$OR^6$, —$SR^6$, —$NR^8R^9$, —$C(O)NR^8R^9$, —$C(O)R^6$, —$C(O)R^6$, —$S(O)_qNR8R^9$, —$C(O)OR^6$, —$NR^8S(O)_2R^9$ or —$NR^8C(O)R^9$, wherein q is 0, 1 or 2.

"Pharmaceutically acceptable salts" represents for certain salts of the compounds that retain their original biological activity and are suitable for pharmaceutical application. Pharmaceutically acceptable salts of compound of Formula (I) may be metal salts, amine salts forming from suitable acids. The metal salts are preferably select from alkali metal and alkaline earth metal salts. Suitable acids comprise inorganic acids and organic acids, such as acetic acid, benzenesulfonic acid, benzoic acid, camphorsulfonic acid, citric acid, ethanesulfonic acid, fumaric acid, gluconic acid, glutamic acid, hydrobromic acid, hydrochloric acid, isethionic acid, lactic acid, malic acid, maleic acid, mandelic acid, methanesulfonic acid, nitric acid, phosphoric acid, succinic acid, sulfuric acid, tartaric acid, p-toluenesulfonic acid, etc. Particularly preferred are hydrochloric acid, hydrobromic acid, phosphoric acid and sulfuric acid, and the most preferred are hydrochloride salt "Pharmaceutical composition" represents for a composition containing one or more compounds described herein (including pharmaceutically acceptable salts or stereoisomers, tautomers or prodrugs thereof) and optionally other pharmaceutical active ingredients, which may contain other components such as a pharmaceutically acceptable carrier and/or an excipient. The purpose of the pharmaceutical composition is to facilitate the administration on organisms, to facilitate the absorption of active ingredients, thereby exerting biological activity.

As used herein, the term "more" includes two or more, such as two, three, four, etc.

Method for Preparing the Compound of the Present Disclosure

In order to achieve the object of the present disclosure, the present disclosure adopts the following technical solutions.

The method for preparing the compound of Formula (I) in the present disclosure comprises the following steps:

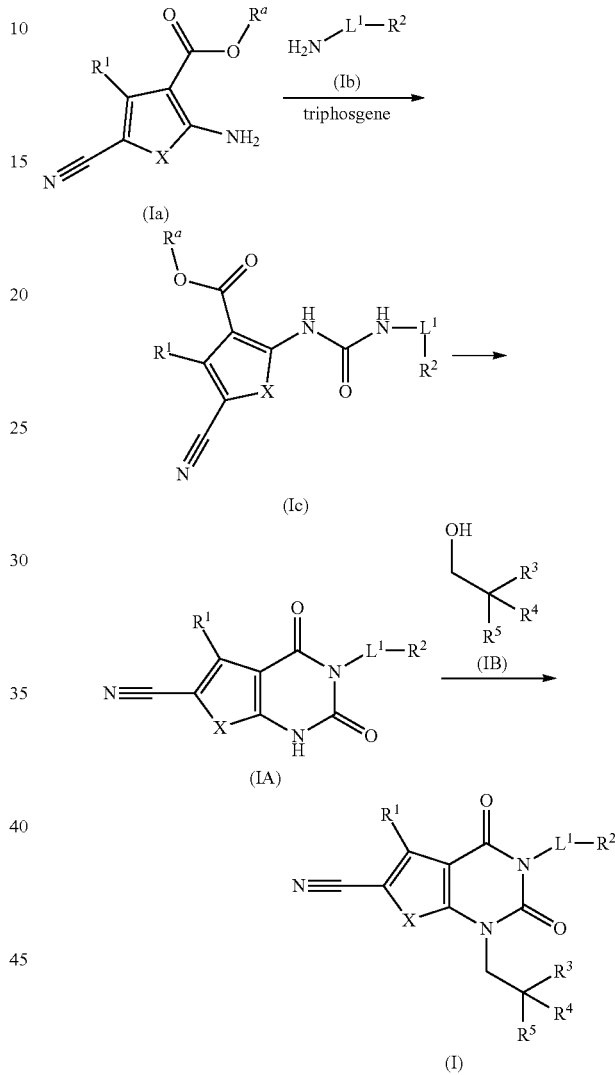

reacting a compound of Formula (Ia) and a compound of Formula (Ib) in the presence of triphosgene under alkaline conditions, to obtain a compound of Formula (Ic); reacting the compound of Formula (Ic) under alkaline conditions to obtain the compound of Formula (IA);

reacting a compound of Formula (IA) with a compound of Formula (IB) or the salts thereof in the presence of triphenylphosphine and diisopropyl azodicarboxylate, optionally further subjecting the resultant to esterolysis, or optionally further reacting the resultant with $NHR^8R^9$ or the salts thereof, to obtain the compound of Formula (I);

wherein, $R^a$ is selected from alkyl;

X, $L^1$, $R^1$-$R^5$, $R^8$ and $R^9$ are as defined in Formula (I) ; and $R^2$ is preferably —C(O)OH or —$C(O)NR^8R^9$.

In the above method for preparing, the alkaline condition is provided by an organic base or an inorganic base. The organic base is selected from diisopropylethylamine, pyridine, triethylamine, piperidine, N-methylpiperazine, 4-dimethylaminopyridine or potassium tert-butoxide, preferably diisopropylethylamine, triethylamine or potassium tert-butoxide; and the inorganic base is selected from sodium carbonate, potassium carbonate, cesium carbonate, sodium hydride, sodium hydroxide, potassium hydroxide, lithium hydroxide or potassium hydride, preferably triethylamine or sodium hydride.

DETAILED DESCRIPTION

The present disclosure will be further described in detail in conjunction with examples, but the examples do not limit the scope of the present disclosure The examples provide the preparation of representative compounds represented by formula (I) and related structural identification data. It should be noted that the following examples are intended to illustrate the disclosure and not to limit the disclosure. The $^1$H NMR spectrum was measured with a Bruker instrument (400 MHz) and the chemical shift was expressed in ppm. The internal standard of tetramethylsilane (0.00 ppm) was used. $^1$H NMR representation: s=singlet, d=doublet, t=triplet, q=quartet, m=multiplet, br=broadened, dd=doublet of the doublet, dt=doublet of the triplet. If a coupling constant is provided, its unit is Hz.

Mass spectrum was tested by LC/MS equipment. The method of ionization may be ESI or APCI.

The thin layer chromatography silica gel plates were Yantai Yellow Sea HSGF254 or Qingdao GF254 silica gel plate. The specification of silica gel plate used for thin layer chromatography (TLC) is 0.15 mm-0.2 mm, and The specification of thin layer chromatography separation and purification product is 0.4 mm-0.5 mm.

Column chromatography generally uses 200-300 meshes Yantai Huanghai silica gel as the carrier.

In the following examples, unless otherwise indicated, all temperatures are degrees Celsius. Unless otherwise indicated, the various starting materials and reagents are either commercially available or synthesized according to known methods, and commercially available starting materials and reagents are used without further purification. Unless otherwise indicated, commercial manufacturers include, but are not limited to, Aldrich Chemical Company, ABCR GmbH & Co. KG, Acros Organics, Guangzan Chemical Technology Co., Ltd. and Jingyan Chemical Technology Co., Ltd., etc.

CD$_3$OD: deuterated methanol.

CDCl$_3$: deuterated chloroform.

DMSO-d6: deuterated dimethyl sulfoxide.

Argon atmosphere indicates that the reaction flask is connected to an argon balloon with a volume of about 1 L.

In the examples, unless otherwise indicated, the solution in the reaction is aqueous solution.

The compounds are purified by silica gel column chromatography and thin layer chromatography, wherein the eluent or developing solvents are selected from A: petroleum ether and acetate system; B: dichloromethane and methanol system; and C: dichloromethane and ethyl acetate; and wherein the volume ratio of solvent depends on the polarity of compound, and may be adjusted by adding a small amount of acid or basic reagents such as acetic acid or triethylamine.

EXAMPLE 1

2-(6-Cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid

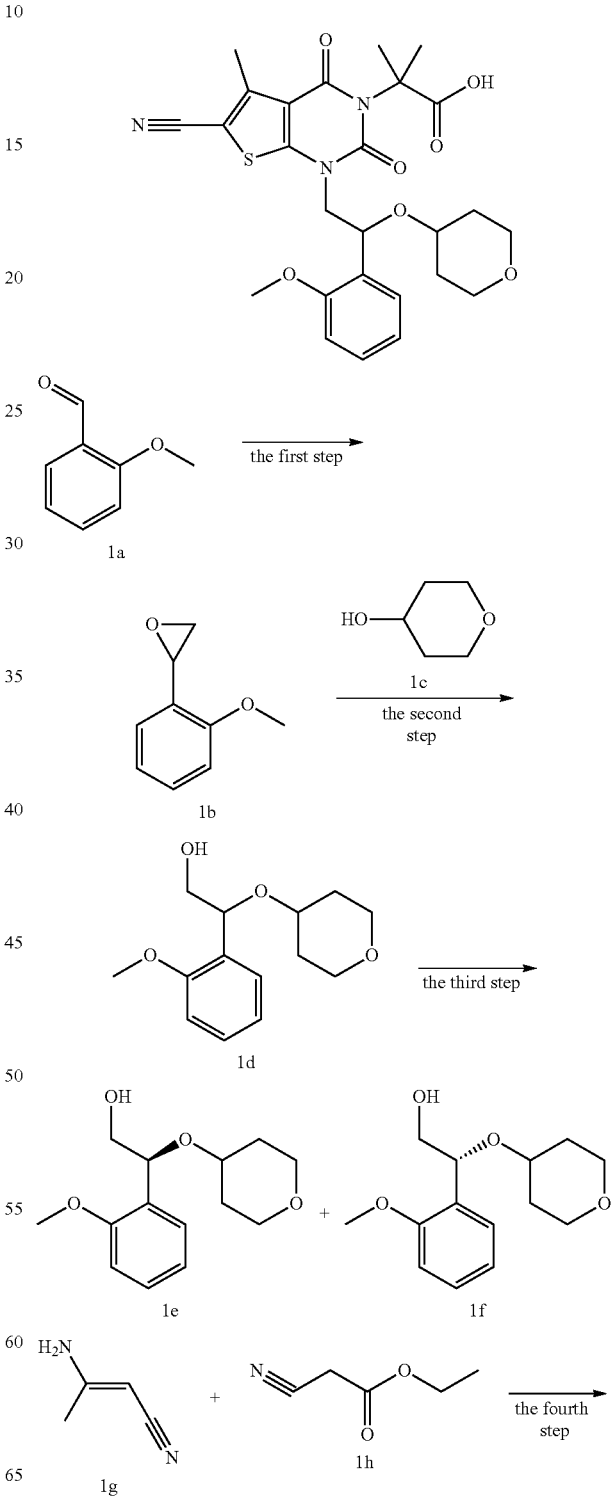

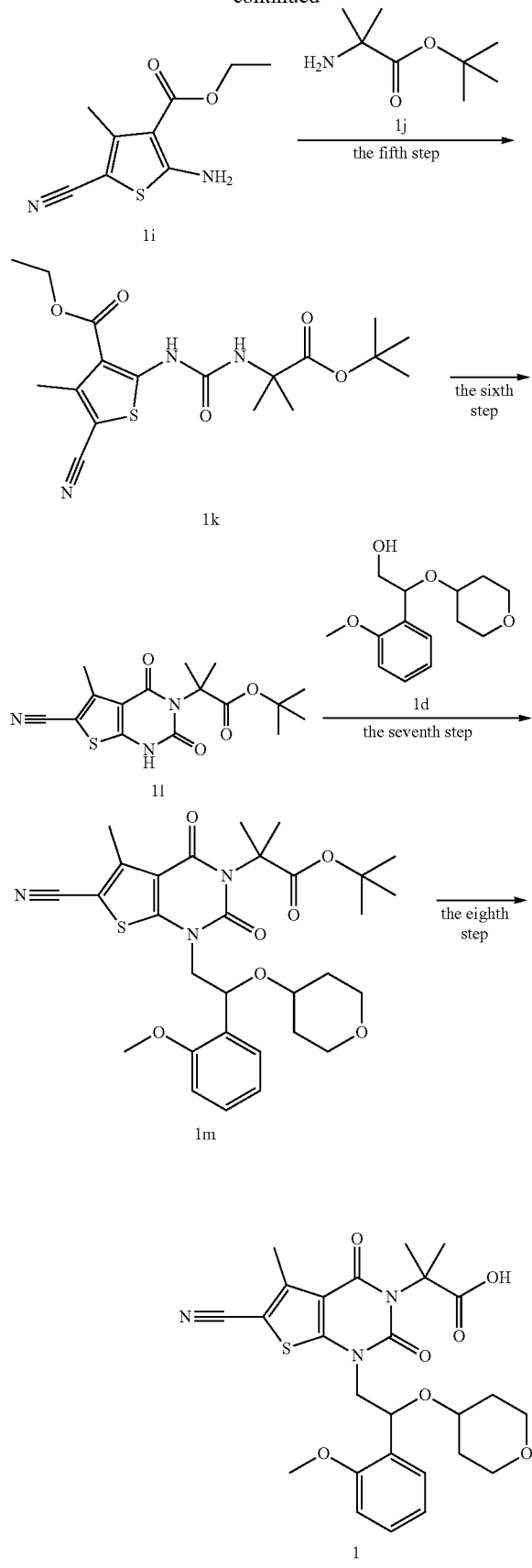

The First Step

(2-methoxyphenyl)ethylene oxide 2-methoxybenzaldehyde 1a (20.0 g, 146.9 mmol) was dissolved in dimethylsulfoxide (100 mL), tert-butylthiohypoiodite (36.0 g, 173.3 mmol) and sodium hydroxide (24.7 g, 441.0 mmol) were successively added in, and heated to 80° C. to react for 1.5 h. The reaction mixture was cooled to room temperature, and water (200 mL) was added in. The mixture was extracted with petroleum ether (200 mL×3). The organic phases were combined, washed with saturated sodium chloride solution (200 mL), dried with anhydrous sodium sulfate, filtered, and concentrated under reduced pressure. The residue was purified by silica gel column chromatography (eluent: A system), to give (2-methoxyphenyl)ethylene oxide 1b (13.1 g, colorless oily product), yield: 59.4%.

$^1$H NMR (400 MHz, CDCl$_3$) δ7.27 (t, J=1.2 Hz, 1H), 7.17 (d, J=7.6 Hz, 1H), 6.98 (t, J=1.2 Hz, 1H), 6.89 (d, J=7.6 Hz, 1H), 4.22 (t, J=0.4 Hz, 1 H), 3.87 (s, 3H), 2.71 (dd, J=5.6, 2.4 Hz, 1 H) 3.14 (dd, J=5.6, 2.4 Hz, 1H).

The Second Sstep

2-(2-methoxyphenyl)-2-((tetrahydro-2H-pyran-4-yl)oxy)ethanol 1d (2-methoxyphenyl)ethylene oxide 1b (26.0 g, 173.0 mmol) was added into tetrahydro-2H-pyran-4-ol 1c (53.1 g, 519.7 mmol) and aluminum trifluoromethanesulfonate (4.10 g, 8.65 mmol) with stirring. The mixture was reacted at room temperature for 3 h. 200 mL dichloromethane and 200 mL water was added into the reaction mixture and liquid separation was conducted. The organic phase was concentrated under reduced pressure. The residue was purified by silica gel column chromatography (eluent: A system), to give (2-methoxyphenyl)-2-((tetrahydro-2H-pyran-4-yl)oxy)ethanol 1d (13.0 g, white solid), yield: 30%.

1d $^1$H NMR (400 MHz, CDCl$_3$) δ7.42 (d, J=8.0 Hz, 1H), 7.26 (t, J=7.2 Hz, 1H), 6.98 (t, J=7.2 Hz, 1H), 6.87 (d, J=8.0 Hz, 1H), 5.07 (dd, J=8.0, 4.0 Hz, 1H), 3.87-4.00 (m, 2H), 3.83 (s, 3H), 3.62-3.72 (m, 1H), 3.46-3.58 (m, 2H), 3.32-3.43 (m, 2H), 2.35-2.(m, 1H), 1.99-2.03 (m, 1H), 1.77-1.80 (m, 1H), 1.60-1.70 (m, 2H).

The Third Step

(S)-2-(2-methoxyphenyl)-2-((tetrahydro-2H-pyran-4-yl)oxy)ethanol 1e

(R)-2-(2-methoxyphenyl)-2-((tetrahydro-2H-pyran-4-yl)oxy)ethanol 1f (2-methoxyphenyl)-2-((tetrahydro-2H-pyran-4-yl)oxy)ethanol 1d (9.0 g) was further separated by supercritical fluid chromatography (SFC) using preparative equipment and chiral column to separate chiral isomers (chiral column Pheno Lux Cellulose-2, 250×30 mm I.D., 5 μm; 60 mL/min; mobile phase A for CO$_2$ and B for iso-propanol), to give (S)-2-(2-methoxyphenyl)-2-((tetrahydro-2H-pyran-4-yl)oxy)ethanol 1e (4.00 g, white solid), yield: 30%, 100% ee, retention time: 1.521 min; and (R)-2-(2-methoxyphenyl)-2-((tetrahydro-2H-pyran-4-yl)oxy)ethanol 1f (4.74 g, white solid), yield: 30%, 100% ee, retention time: 1.679 mim.

The Fourth Step

Ethyl 2-amino-5-cyano-4-methylthiophene-3-carboxylate 3-aminobut-2-enenitrile 1g (25.0 g, 304 mmol), powdered sulfur (9.75 g, 304 mmol) and 2-cyanoethyl acetate 1h (32.44 mL, 304 mmol) were dissolved in 250 mL ethanol, pyridine (2.58 mL, 30.4 mmol) was added at 45° C. The mixture was heated and refluxed for 10 h. The reaction mixture was filtered, and the filter cake was washed with ethanol (5 mL×3). The obtained brown solid was recrystallized with 80 mL ethanol to give ethyl 2-amino-5-cyano-4-methylthiophene-3-carboxylate 1i (30.0 g, brown solid), yield: 47%.

MS m/z(ESI): 210.9 [M+1]

The Fifth Step

Ethyl 2-(3-(1-(tert-butoxy)-2-methyl-1-oxopropan-2-yl)ureido)-5-cyano-4-methylthiophene-3-formate Ethyl 2-amino-5-cyano-4-methylthiophene-3-carboxylate 1i (10.0 g, 47.56 mmol) was dissolved in 60 mL dichloromethane. In an ice bath, triethylamine (33 mL, 238 mmol) was added, and triphosgene (7.06 g, 23.8 mmol) in 10 mL dichloromethane was added, and the mixture was stirred in an ice bath for 1.5 h. Tert-butyl 2-amino-2-methyl propanoate 1j (9.3 g, 47.56 mmol) was added, and the mixture was reacted at room temperature for 12 h. 250 mL water was added into the reaction mixture, which then was layered. The water phase was extracted with dichloromethane (200 mL×2). The organic phases were combined, washed with saturated saline solution (250 mL×3), concentrated under reduced pressure. The obtained residue was triturated (with petroleum ether/ethyl acetate=6/1) to obtain ethyl 2-(3-(1-(tert-butoxy)-2-methyl-1-oxopropan-2-yl)ureido)-5-cyano-4-methylthiophene-3-formate 1k (13.0 g, light yellow solid), yield: 72.2%.

MS m/z(ESI): 395.9 [M+1].

The Sixth Step

Tert-butyl 2-(6-Cyano-5-methyl-2,4-dioxo-1,2-dihydrothieno[2,3-d]pyrimidin-3(4H)-yl)-2-methylpropionate Ethyl 2-(3-(1-(tert-butoxy)-2-methyl-1-oxopropan-2-yl) ureido)-5-cyano-4-methylthiophene-3-formate 1k (10.0 g, 25.0 mmol) was dissolved in 70 mL N,N-dimethylformamide. The mixture was cooled to 0° C., and 60% sodium hydride (2.02 g, 50.0 mmol) was added. After the completion of addition, the mixture was heated to 90° C. to react for 10min. The reaction mixture was cooled to room temperature, slowly poured to 250 mL saturated ammonium chloride solution, and extracted with dichloromethane (200 mL×4). The organic phases were combined, successively washed with water (200 mL×5) and saturated saline solution (200 mL), dried with anhydrous sodium sulfate, concentrated under reduced pressure to obtain the crude product tert-butyl 2-(6-cyano-5-methyl-2,4-dioxo-1,2-dihydrothieno[2,3-d] pyrimidin-3(4H)-yl)-2-methylpropionate 1l (3.45 g, white solid); yield: 39.5%.

MS m/z(ESI): 293.9 [M-56+1]

The Seventh Step

Tert-butyl 2-(6-cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate Under nitrogen protection, tert-butyl 2-(6-cyano-5-methyl-2,4-dioxo-1,2-dihydrothieno[2,3-d]pyrimidin-3 (4H)-yl)-2-methylpropionate 1l(180 mg, 0.515 mmol), 2-(2-methoxyphenyl)-2-((tetrahydro-2H-pyran-4-yl)oxy)ethanol 1d (263 mg, 0.973 mmol) and triphenylphosphine (270 mg, 1.03 mmol) were dissolved in 5 mL anhydrous tetrahydrofuran. The mixture was cooled to 0° C., and diisopropyl azodicarboxylate (204 µL, 1.03 mmol) was added. After the completion of addition, the mixture was heated to room temperature to react for 18 h. 8 mL water was added into the reaction mixture, which was extracted with ethyl acetate (5 mL×3). The organic phases were combined, washed with saturated saline solution (5 mL×2), dried with anhydrous sodium sulfate, and concentrated under reduced pressure. The obtained residue was purified by silica gel column chromatography (eluent: A system) to obtain the tert-butyl 2-(6-cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylproponate 1m (224 mg, white solid); yield: 74.5%.

MS m/z(ESI): 583.8 [M+1].

The Eighth Step

2-(6-Cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid Tert-butyl 2-(6-cyano-1-(2-(2-methoxyphenyl)-2-((tetrahydro-2H-pyran-4-yl)oxy)ethyl)-5-methyl-2,4-dioxo-1,2-dihydrothiophenо[2,3-d]pyrimidin-3(4H)-yl)-2-methylpropionate 1m (220 mg, 0.377 mmol) was dissolved in 10 mL dichloromethane. The mixture was cooled to 0° C., and 2 mL trifluoromethanesulfonic acid was added. After the completion of addition, the mixture was heated to room temperature to react for 3 h. The reaction mixture was added with 10 mL water, and extracted with dichloromethane (10 mL×3). The organic phases were combined, washed with water (10 mL×3), concentrated under reduced pressure. The obtained residue was purified by silica gel column chromatography (eluent: B system), and the obtained crude product was further purified by silica gel thin layer chromatography (developing solvent: B system) to obtain the 2-(6-cyano-1-(2-(2-methoxyphenyl)-2-((tetrahydro-2H-pyran-4-yl)oxy) ethyl)-5-methyl-2,4-dioxo-1,2-dihydrothiopheno[2,3-d]pyrimidin-3(4H)-yl)-2-methylpropionic acid 1 (72 mg, white solid); yield: 36.2%.

MS m/z(ESI): 549.9[M+23].

$^1$H NMR (400 MHz, CDCl$_3$) δ 7.51 (d, J=7.5 Hz, 1H), 7.31 (t, J=7.8 Hz, 1H), 7.03 (t, J=7.5 Hz, 1H), 6.85 (d, J=8.2 Hz, 1H), 5.43-5.29 (m, 1H), 4.08 (m, 2H), 3.83 (s, 3H), 3.79-3.61 (m, 2H), 3.51-3.40 (m, 1H), 3.39-3.25 (m, 2H), 2.63 (s, 3H), 1.82 (d, J=12.0 Hz, 6H), 1.81-1.62 (m, 2H), 1.49-1.35 (m, 2H).

EXAMPLE 2

(S)-2-(6-Cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid

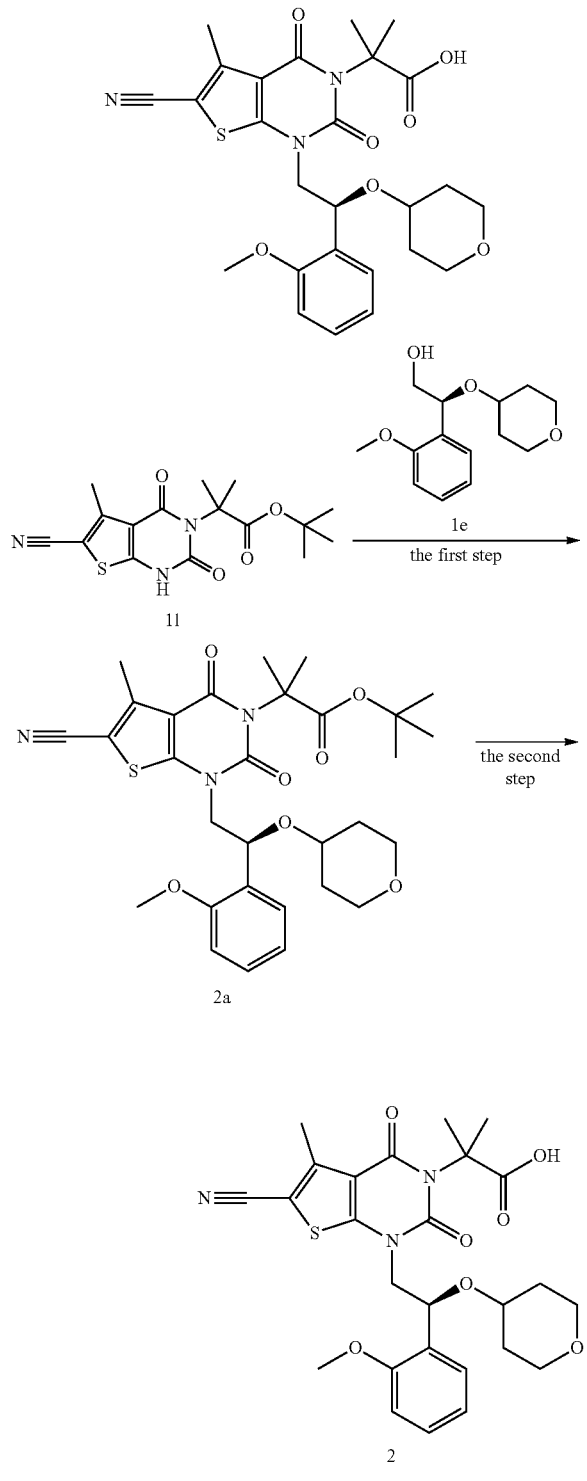

The First Step (S)-tert-butyl 2-(6-cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate Under nitrogen protection, tert-butyl 2-(6-cyano-5-methyl-2,4-dioxo-1,2-dihydrothieno[2,3-d]pyrimidin-3(4H)-yl)-2-methylpropionate 1l (180 mg, 0.515 mmol), (S)-2-(2-methoxyphenyl)-2-((tetrahydro-2H-pyran-4-yl)oxy)ethanol 1e (209 mg, 0.773 mmol) and triphenylphosphine (270 mg, 1.03 mmol) were dissolved in 5 mL tetrahydrofuran, cooled to 0° C., and diisopropyl azodicarboxylate (204 μL, 1.03 mmol) was added. After the completion of addition, the mixture was stirred at 0° C. for 5 min, and heated to room temperature to react for 16 h. The reaction mixture was concentrated under reduced pressure, and the obtained residue was purified by silica gel column chromatography (eluent: A system) to obtain (S)-tert-butyl 2-(6-cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate 2a (410 mg, sticky white solid); yield: 98%.

MS m/z(ESI): 605.9 [M+23].

The Second Step (S)-2-(6-cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid (S)-tert-butyl 2-(6-cyano-1-(2-(2-m ethoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate 2a (300 mg, 0.514 mmol) was dissolved in 20 mL dichloromethane, cooled to 0° C., and 4 mL trifluoromethanesulfonic acid was added. After the completion of addition, the mixture was stirred at 0° C. for 5 min, heated to room temperature and reacted for 3 h. 10 mL water was added into the reaction mixture, and the reaction mixture was extracted with dichloromethane (10 mL×3). The organic phases were combined, washed with water (10 mL×3), dried with anhydrous sodium sulfate, and filtered. The filtrate was concentrated under reduced pressure. The obtained residue was purified by silica gel column chromatography (eluent: B system), and the obtained crude product was further purified by silica gel thin layer chromatography (developing solvent: B system) to obtain (S)-2-(6-cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid 2 (82 mg, white solid); yield: 30.2%.

MS m/z(ESI): 549.8[M+23]

$^1$H NMR (400 MHz, CDCl$_3$) δ 7.51 (d, J=7.6 Hz, 1H), 7.31 (t, J=7.1 Hz, 1H), 7.03 (t, J=7.5 Hz, 1H), 6.86 (d, J=8.3 Hz, 1H), 5.37-5.30 (m, 1H), 4.21-4.01 (m, 2H), 3.83 (s, 3H), 3.79-3.67 (m, 2H), 3.47-3.40 (m, 1H), 3.39-3.29 (m, 2H), 2.64 (s, 3H), 1.82 (d, J=11.5 Hz, 6H), 1.75 (d, J=6.8 Hz, 2H), 1.46-1.36 (m, 2H).

EXAMPLE 3

(R)-2-(6-cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid

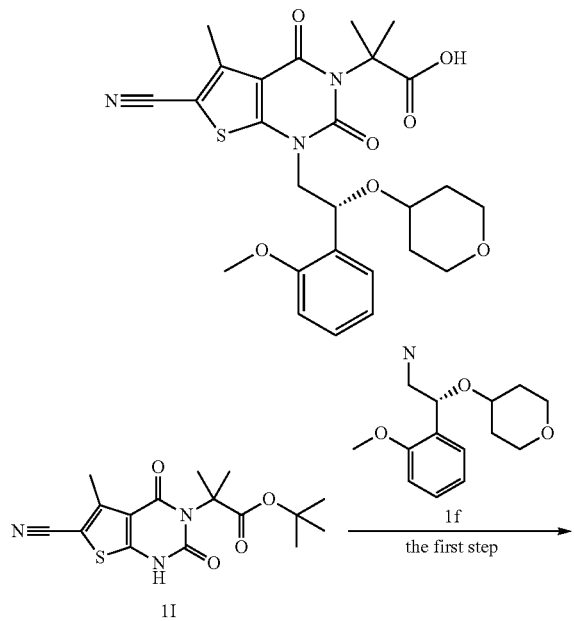

The First Step (R)-Tert-butyl 2-(6-cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate Under the protection of nitrogen, tert-butyl 2-(6-cyano-5-methyl-2,4-dioxo-1,2-dihydrothieno[2,3-d]pyrimidin-3(4H)-yl)-2-methylpropionate 1 (180 mg, 0.515 mmol), (R)-2-(2-methoxyphenyl)-2-((tetrahydro-2H-pyran-4-yl)oxy)ethanol 1f (209 mg, 0.773 mmol) and triphenylphosphine (270 mg, 1.03 mmol) were dissolved in 5 mL tetrahydrofuran. The resultant was cooled to 0° C. Diisopropyl azodicarboxylate (204 μL, 1.03 mmol) was added, and after the completion of addition, the mixture was stirred at 0° C. for 5 min, and then heated to room temperature to react for 18 h. The reaction mixture was concentrated under reduced pressure, and the obtained residue was purified by silica gel column chromatography (eluent: A system) to obtain the crude product (R)-tert-butyl 2-(6-cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate 3a (470 mg, sticky white solid). The product was directly used for the next reaction without further purification.

MS m/z(ESI): 583.9 [M+1]

The Second Step (R)-2-(6-cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid (R)-tert-butyl 2-(6-cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate 3a (300 mg, 0.514 mmol) was dissolved in 15 mL dichloromethane, cooled to 0° C., and 3 mL trifluoromethanesulfonic acid was added. After the completion of addition, the resultant was stirred at 0° C. for 5 min. The mixture was heated to room temperature to react for 2 h. 10 mL water was added into the reaction mixture, and the reaction mixture was extracted with dichloromethane (15 mL×3). The organic phases were combined, washed with water (15 mL×3), dried with anhydrous sodium sulfate, and filtered. The filtrate was concentrated under reduced pressure, and the obtained residue was purified by silica gel thin layer chromatography (developing solvent: B system) to obtain (R)-2-(6-cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid 3 (64 mg, white solid); yield: 23.6%.

MS m/z(ESI): 549.8[M+23].

$^1$H NMR (400 MHz, CDCl$_3$) δ 7.50 (d, J=6.4 Hz, 1H), 7.31 (t, J=7.1 Hz, 1H), 7.03 (t, J=7.5 Hz, 1H), 6.85 (d, J=8.2 Hz, 1H), 5.35-5.30 (m, 1H), 4.15-3.94 (m, 2H), 3.83 (s, 3H), 3.72 (dt, J=16.2, 4.9 Hz, 2H), 3.43 (dd, J=8.1, 4.1 Hz, 1H), 3.35 (tdd, J=8.6, 5.6, 2.7 Hz, 2H), 2.63 (s, 3H), 1.82 (d, J=11.6 Hz, 6H), 1.74 (s, 2H), 1.47-1.36 (m, 2H).

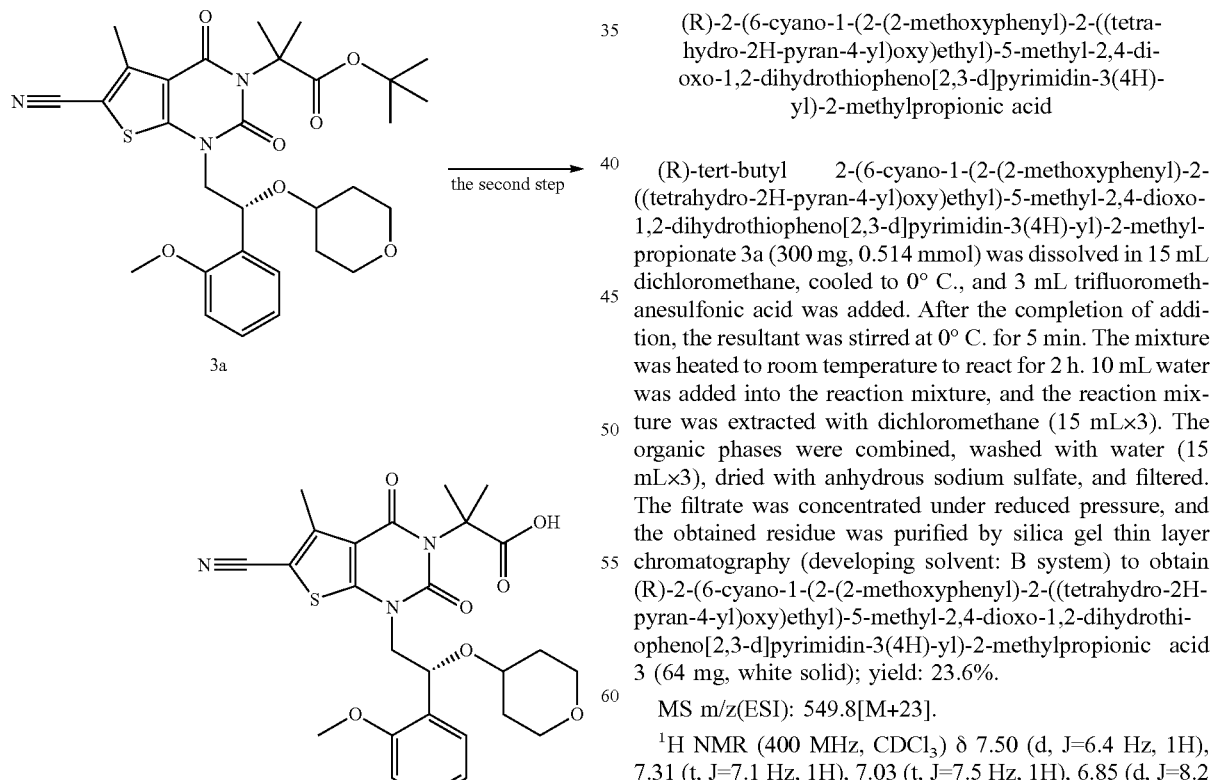

EXAMPLE 4

2-(6-Cyano-1-(2-(5-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid

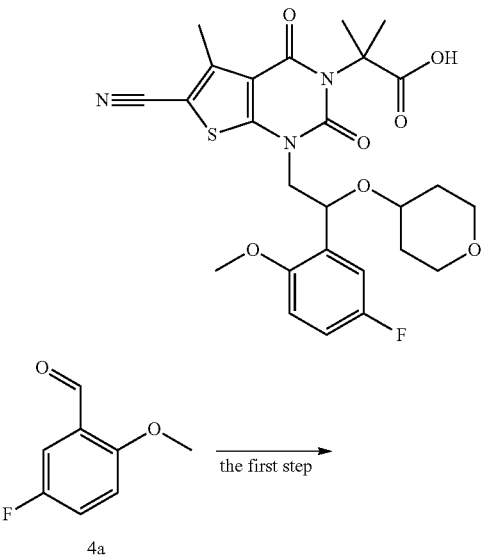

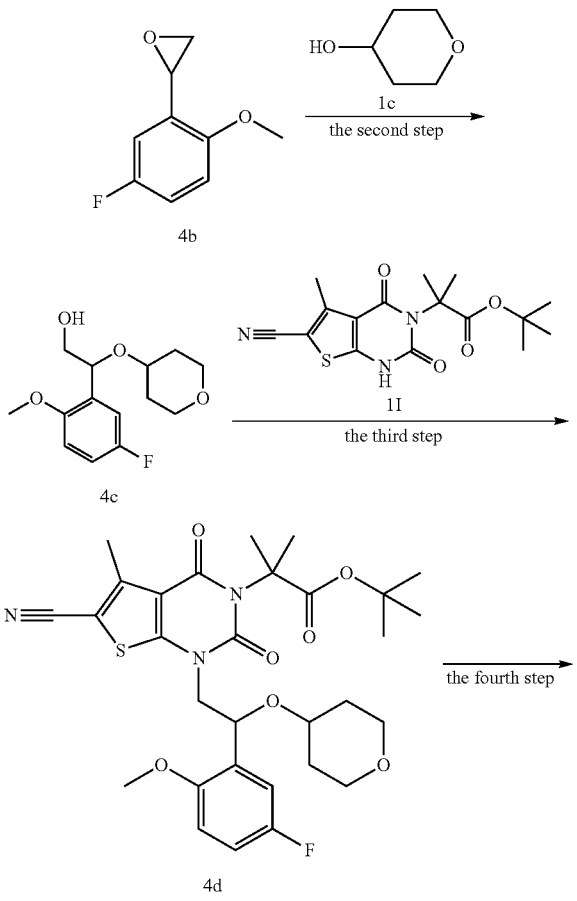

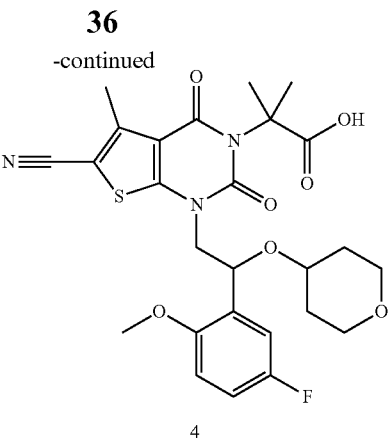

4

The First Step (5-fluoro-2-methoxyphenyl)ethylene oxide

Tert-butylthiohypoiodite (7.94 g, 38.9 mmol) and potassium hydroxide (24.7 g, 441.0 mmol) were dissolved in 50 mL dimethylsulfoxide, and 5-fluoro-2-methoxybenzaldehyde 4a (5.0 g, 32.4 mmol) was added, and the mixture was heated to 80° C. to react for 1 h. The reaction mixture was cooled to room temperature, and 200 mL water was added. The reaction mixture was extracted with ethyl acetate (200 mL×2). The organic phases were combined, washed with saturated sodium chloride solution (200 mL), dried with anhydrous sodium sulfate, filtered, and concentrated under reduced pressure. The residue was purified by silica gel column chromatography (eluent: A system) to obtain the (5-fluoro-2-methoxyphenyl)ethylene oxide 4b (4.5 g, light yellow oily product); yield: 83%.

$^1$H NMR (400 MHz, CDCl$_3$) δ 6.85-7.00 (m, 2H), 6.75-6.83 (m, 1H), 4.15-4.20 (m, 1H), 3.84 (s, 3H), 3.10-3.18 (m, 1H), 2.63-2.68 (m, 1H).

The Second Step 2-(5-fluoro-2-methoxyphenyl)-2-((tetrahydro-2H-pyran-4-yl)oxy)ethanol (5-Fluoro-2-methoxyphenyl)ethylene oxide 4b (1.40 g, 8.34 mmol) was added into tetrahydro-2H-pyran-4-ol 1c (2.56 g, 25.1 mmol) and aluminum trifluoromethanesulfonate (200 mg, 0.44 mmol), and reacted at room temperature for 3 h. 50 mL dichloromethane and 50 mL water were added into the reaction mixture, and the water layer was separated out. The mixture was washed with saturated sodium chloride solution (50 mL), dried with anhydrous sodium sulfate, filtered, and concentrated under reduced pressure. The residue was purified by silica gel column chromatography (eluent: A system) to obtain 2-(5-fluoro-2-methoxyphenyl)-2-((tetrahydro-2H-pyran-4-yl)oxy)ethanol 4c (1.0 g, colorless oily product); yield: 45%.

$^1$H NMR (400 MHz, CDCl3) δ 7.10-7.18 (m, 1H), 6.89-6.95 (m, 1H), 6.76-6.81 (m, 1H), 4.90-5.10 (m, 1H), 3.89-3.98 (m, 2H), 3.80 (s, 3H), 3.62-3.70 (m, 1H), 3.30-3.55 (m, 4H), 1.85-2.35 (m, 2H), 1.52-1.68 (m, 2H).

The Third Step

Tert-butyl 2-(6-cyano-1-(2-(5-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate Under nitrogen protection, tert-butyl 2-(6-cyano-5-methyl-2,4-dioxo-1,2-dihydrothieno[2,3-d]pyrimidin-3(4H)-yl)-2-methylpropionate 11 (140 mg, 0.40 mmol), 2-(2-methoxyphenyl)-2-((tetrahydro-2H-pyran-4-yl)oxy)ethanol 4c (162.2 mg, 0.60 mmol) and triphenylphosphine (209.7 mg, 0.80 mmol) were dissolved in 5 mL tetrahydrofuran, cooled to 0° C., and diisopropyl azodicarboxylate (158.6 μL, 0.80 mmol) was added. After the completion of addition, the mixture was heated to room temperature to react for 22 h. 5 mL water was added into the reaction mixture, and the reaction mixture was extracted with dichloromethane (5 mL×3). The organic phases were combined, washed with water (5 mL×2), dried with anhydrous sodium sulfate, and concentrated under reduced pressure. The obtained residue was purified by silica gel column chromatography (eluent: A system), and the obtained crude product was further purified by silica gel thin layer chromatography (developing solvent: A system) to obtain tert-butyl 2-(6-cyano-1-(2-(5-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate 4d (55 mg, white solid); yield: 23%.

MS m/z(ESI): 623.9 [M+23]

The Fourth Step 2-(6-Cyano-1-(2-(5-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid Tert-butyl 2-(6-cyano-1-(2-(5-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate 4d (60 mg, 0.099 mmol) was dissolved in 4 mL dichloromethane, cooled to 0° C., and 0.8 mL trifluoromethanesulfonic acid was added. After the completion of addition, the mixture was heated to room temperature to react for 5 h. 4 mL water was added into the reaction mixture, and the reaction mixture was extracted with dichloromethane (5 mL×3). The organic phases were combined, successively washed with water (5 mL×3) and saturated saline solution (5 mL), dried with anhydrous sodium sulfate, and filtered. The filtrate was concentrated under reduced pressure. The obtained residue was purified by silica gel thin layer chromatography (developing solvent: B system) to obtain 2-(6-cyano-1-(2-(5-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid 4 (33 mg, white solid); yield: 61.1%.

MS m/z(ESI): 543.9[M-1]

$^1$H NMR (400 MHz, CDCl$_3$) δ 7.23 (dd, J=8.9, 3.1 Hz, 1H), 6.98 (td, J=8.5, 3.1 Hz, 1H), 6.79 (dd, J=9.0, 4.1 Hz, 1H), 5.31-5.24 (m, 1H), 4.08 (s, 1H), 3.99 (s, 1H), 3.78 (s, 3H), 3.78-3.67 (m, 2H), 3.49-3.40 (m, 1H), 3.40-3.27 (m, 2H), 2.64 (s, 3H), 1.82 (d, J=12.4 Hz, 6H), 1.76 (d, J=13.3 Hz, 2H), 1.47-1.36 (m, 2H).

EXAMPLE 5

2-(6-Cyano-1-(2-(2-(difluoromethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid

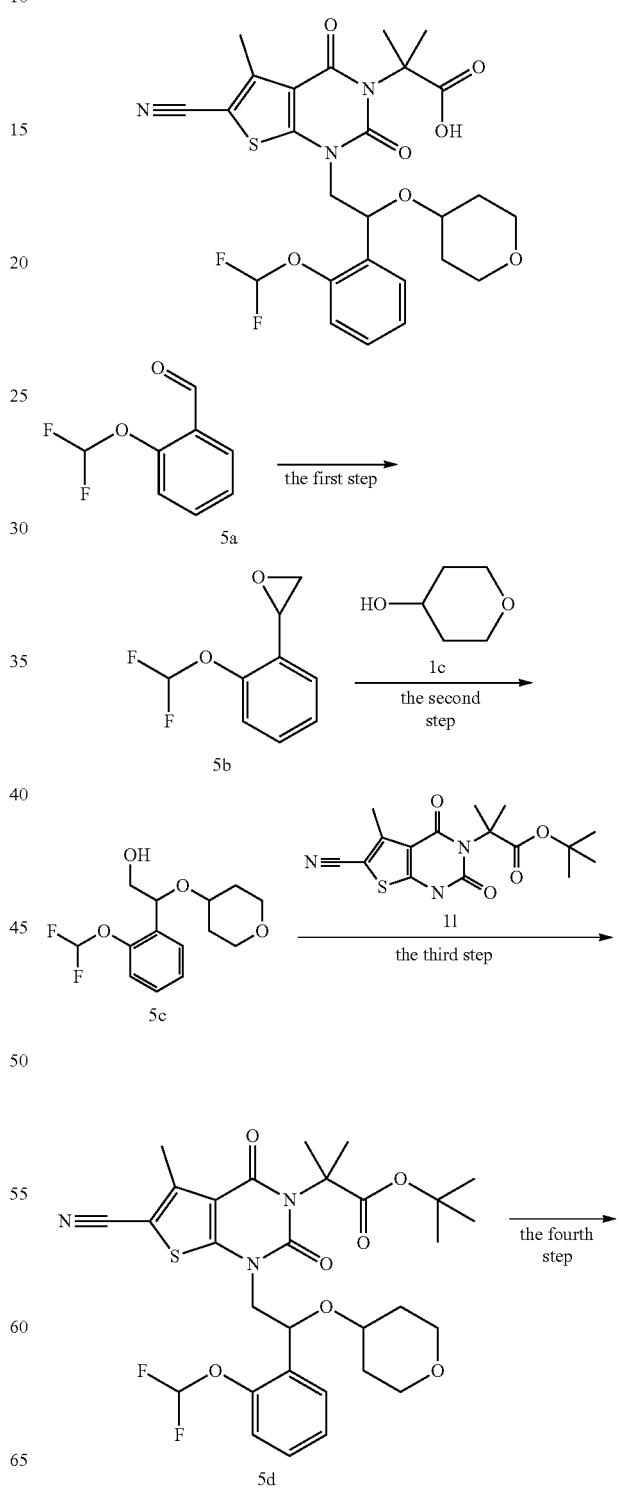

-continued

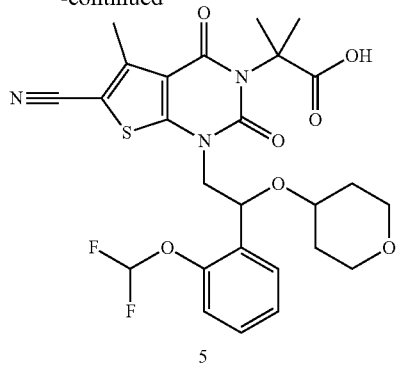

5

The First Step

2-(2-(Difluoromethoxy)phenyl)ethylene oxide

Tert-butylthiohypoiodite (2.45 g, 12.0 mmol) and potassium hydroxide (1.68 g, 30.0 mmol) were dissolved in 30 mL dimethylsulfoxide, and 2-(difluoromethoxy)benzaldehyde 5a (1.72 g, 10.0 mmol) was added. The mixture was heated to 80° C. to react for 1 h. The reaction mixture was cooled to room temperature, and 100 mL water was added. The reaction mixture was extracted with ethyl acetate (100 mL×2). The organic phases were combined, washed with saturated sodium chloride solution (100 mL×2), dried with anhydrous sodium sulfate, filtered, and concentrated under reduced pressure. The residue was purified by silica gel column chromatography (eluent: A system) to obtain 2-(2-(difluoromethoxy)phenyl)ethylene oxide 5b (1.3 g, colorless oily product); yield: 70%.

$^1$H NMR (400 MHz, CDCl$_3$) δ 7.20-7.31 (m, 3H), 7.11 (d, J=0.8 Hz, 1H), 6.56 (t, J=7.8 Hz, 1H), 4.15-4.19 (m, 1H), 3.15-3.17 (m, 1H), 2.69-2.71 (m, 1H).

The Second Step

2-(2-(difluoromethoxy)phenyl)-2-((tetrahydro-2H-pyran-4-yl)oxy)ethanol 2-(2-(Difluoromethoxy)phenyl)ethylene oxide 5b (1.30 g, 6.99 mmol) was added in tetrahydro-2H-pyran-4-ol 1c (2.14 g, 20.97 mmol) and aluminum trifluoromethanesulfonate (331 mg, 0.70 mmol) with stirring, and the mixture was reacted at room temperature for 2 h. 100 mL water was added into the reaction mixture, and the reaction mixture was extracted with ethyl acetate (100 mL×2). The organic phases were combined, washed with saturated sodium chloride solution (100 mL×2), dried with anhydrous sodium sulfate, filtered, and concentrated under reduced pressure. The residue was purified by silica gel column chromatography (eluent: A system) to obtain 2-(2-(difluoromethoxy)phenyl)-2-((tetrahydro-2H-pyran-4-yl)oxy)ethanol 5c (650 mg, colorless oily product); yield: 28%.

$^1$H NMR (400 MHz, CDCl$_3$) δ 7.54 (dd, J=0.4, 0.8 Hz, 1H), 7.24-7.34 (m, 2H), 7.12 (d, J=0.8 Hz, 1H), 6.57 (t, J=7.8 Hz, 1H), 5.02-5.05 (m, 1H), 3.88-3.98 (m, 2H), 3.35-3.68 (m, 5H), 2.25-2.30 (m, 1H), 1.95-2.05 (m, 1H), 1.61-1.75 (m, 2H).

The Third Step

Tert-butyl 2-(6-Cyano-1-(2-(2-(difluoromethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate Under nitrogen protection, tert-butyl 2-(6-cyano-5-methyl-2,4-dioxo-1,2-dihydrothieno[2,3-d]pyrimidin-3(4H)-yl)-2-methylpropionate 1l (150 mg, 0.43 mmol), 2-(2-(difluoromethoxy)phenyl)-2-((tetrahydro-2H-pyran-4-yl)oxy)ethanol 5c (186 mg, 0.65 mmol) and triphenylphosphine (169 mg, 0.65 mmol) were dissolved in 10 mL tetrahydrofuran, and diisopropyl azodicarboxylate (131 mg, 0.65 mmol) was added, and the mixture was reacted at room temperature for 18 h. 50 mL water was added into the reaction mixture, and the reaction mixture was extracted with ethyl acetate (100 mL×2). The organic phases were combined, washed with saturated sodium chloride solution (50 mL), dried with anhydrous sodium sulfate, filtered, and concentrated under reduced pressure. The residue was purified by silica gel column chromatography (eluent: A system), and the obtained crude product was further purified by silica gel thin layer chromatography (developing solvent: A system) to obtain tert-butyl2-(6-cyano-1-(2-(2-(difluoromethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate 5d (200 mg, white solid); yield: 75.2%.

MS m/z(ESI): 619.9 [M+1]

The Fourth Step

2-(6-Cyano-1-(2-(2-(difluoromethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid Tert-butyl 2-(6-cyano-1-(2-(2-(difluoromethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate 5d (200 mg, 0.323 mmol) was dissolved in 5 mL dichloromethane, and 1 mL trifluoroacetic acid was added in, and the mixture was reacted at room temperature for 1 h. 50 mL water was added into the reaction mixture, and the reaction mixture was extracted with ethyl acetate (50 mL×2). The organic phases were combined, washed with saturated sodium chloride solution (50 mL×3), dried with anhydrous sodium sulfate, filtered, and concentrated under reduced pressure. The residue was purified by silica gel column chromatography (eluent: A system), and the obtained crude product was further purified by silica gel thin layer chromatography (developing solvent: A system) to obtain the 2-(6-cyano-1-(2-(2-(difluoromethoxy)phenyl)-2-((tetrahydro-2H-pyran-4-yl)oxy)ethyl)-5-methyl-2,4-dioxo-1,2-dihydrothiopheno[2,3-d]pyrimidin-3 (4H)-yl)-2-methylpropionicacid 5 (20 mg, white solid); yield: 11%.

MS m/z(ESI): 545.8[M-18]

$^1$H NMR (400 MHz, CDCl$_3$) δ 7.59 (d, J=0.8 Hz, 1H), 7.27-7.39 (m, 2H), 7.16 (d, J=0.8 Hz, 1H), 6.67 (t, J=7.8 Hz, 1H), 5.30-5.35 (m, 1H), 4.20-4.30 (m, 2H), 3.50-3.70 (m,

2H), 3.30-3.50 (m, 3H), 2.64 (s, 3H), 1.54-1.80 (m, 7H), 1.27-1.54 (m, 1H), 1.24-1.27 (m, 2H).

EXAMPLE 6

2-(6-Cyano-1-(2-(2-ethoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid

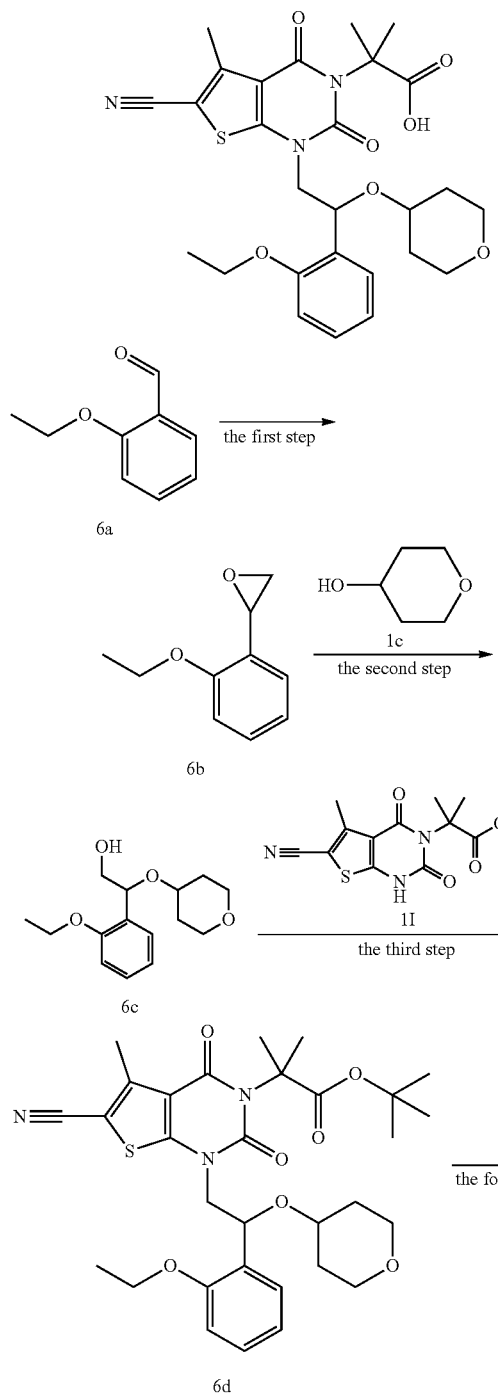

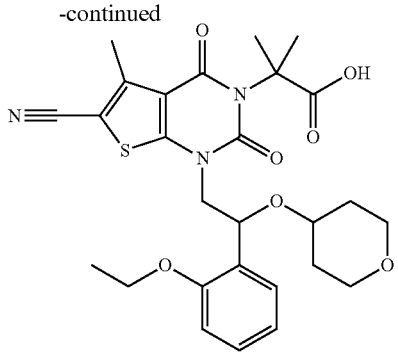

The First Step 2-(2-Ethoxyphenyl)ethylene oxide

2-Ethoxy-benzaldehyde 6a (5.00 g, 33.3 mmol) and tert-butylthiohypoiodite (8.16 g, 39.9 mmol) were dissolved in 20 mL dimethylsulfoxide, and potassium hydroxide (5.6 g, 99.9 mmol) were added, and the mixture was heated to 80° C. to react for 2 h. The reaction mixture was cooled to room temperature and filtered. 100 mL water was added into the filtrate, and the filtrate was extracted with ethyl acetate (40 mL×3). The organic phases were combined, successively washed with water (40 mL×2) and saturated sodium chloride solution (40 mL×2), dried with anhydrous sodium sulfate, filtered, and concentrated under reduced pressure. The residue was purified by silica gel column chromatography (eluent: A system) to obtain 2-(2-ethoxyphenyl)ethylene oxide 6b (5.0 g, light yellow oily product); yield: 91.6%.

MS m/z(ESI): 165.0 [M+1]

The Second Step 2-(2-Ethyoxyphenyl)-2-((tetrahydro-2H-pyran-4-yl)oxy)ethanol 2-(2-Ethoxyphenyl)ethylene oxide 6b (5.0 g, 30.5 mmol) was added into tetrahydro-2H-pyran-4-ol 1c (9.3 g, 91.4 mmol) and aluminum trifluoromethanesulfonate (580 mg, 1.22 mmol) with stirring, and the mixture was reacted at room temperature for 1.5 h. 50 mL water was added into the reaction mixture, and the reaction mixture was extracted with ethyl acetate (30 mL×3). The organic phases were combined, successively washed with water (30 mL×2) and saturated sodium chloride solution (30 mL), dried with anhydrous sodium sulfate, filtered, and concentrated under reduced pressure. The residue was purified by silica gel column chromatography (eluent: A system) to obtain 2-(2-ethoxyphenyl)-2-((tetrahydro-2H-pyran-4-yl)oxy)ethanol 6c (2.5 g, dark yellow oily product); yield: 30.8%.

¹H NMR (400 MHz, CDCl₃) δ 7.41 (dd, J=7.5, 1.4 Hz, 1H), 7.27-7.22 (t, J=7.5 Hz, 1H), 6.96 (t, J=7.5 Hz, 1H), 6.85 (d, J=8.2 Hz, 1H), 5.09 (dd, J=8.4, 3.3 Hz, 1H), 4.05 (qd, J=7.0, 1.7 Hz, 2H), 3.93 (ddt, J=20.5, 11.6, 4.2 Hz, 2H), 3.69 (dd, J=11.4, 3.4 Hz, 1H), 3.58-3.45 (m, 2H), 3.37 (ddd, J=21.9, 12.1, 2.8 Hz, 2H), 2.18 (s, 1H), 2.05-1.96 (m, 1H), 1.82-1.74 (m, 1H), 1.70-1.57 (m, 2H), 1.41 (t, J=5.7 Hz, 3H).

43

The Third Step

Tert-butyl 2-(6-cyano-1-(2-(2-ethoxyphenyl)-2-((tetrahydro-2H-pyran-4-yl)oxy)ethyl)-5-methyl-2,4-dioxo-1, 2-dihydrothiopheno[2,3-d]pyrimidin-3 (4H)-yl)-2-methylpropionate Under nitrogen protection, tert-butyl 2-(6-cyano-5-methyl-2,4-dioxo-1,2-dihydrothieno[2,3-d]pyrimidin-3 (4H)-yl)-2-methylpropionate 1l (200 mg, 0.57 mmol), 2-(2-ethoxyphenyl)-2-((tetrahydro-2H-pyran-4-yl)oxy)ethanol 6c (228 mg, 0.86 mmol) and triphenylphosphine (314 mg, 1.20 mmol) were dissolved in 5 mL tetrahydrofuran, cooled to 0° C., and diisopropyl azodicarboxylate (238 μL, 1.20 mmol) were added. After the completion of addition, the mixture was heated to room temperature to react for 18 h. LCMS test showed that a half of the raw materials did not completely react. (2-Ethoxyphenyl)-2-((tetrahydro-2H-pyran-4-yl)oxy)ethanol 6c (152 mg, 0.57 mmol), triphenylphosphine (157 mg, 0.60 mmol) and diisopropyl azodicarboxylate (119 μL, 0.60 mmol) were supplemented, and the mixture was continuously reacted for 22 h. 10 mL water was added into the reaction mixture, and the reaction mixture was extracted with ethyl acetate (10 mL×3). The organic phases were combined, successively washed with water (20 mL×2) and saturated sodium chloride solution (20 mL), dried with anhydrous sodium sulfate, and concentrated under reduced pressure. The obtained residue was purified by silica gel column chromatography (eluent: A system) to obtain tert-butyl 2-(6-cyano-1-(2-(2-ethoxyphenyl)-2-((tetrahydro-2H-pyran-4-yl)oxy)ethyl)-5-methyl-2,4-dioxo-1, 2-dihydrothiopheno[2,3-d]pyrimidin-3(4H)-yl)-2-methylpropionate 6d (130 mg, white solid); yield: 76%.

MS m/z(ESI): 597.9 [M+1]

The Fourth Step 2-(6-Cyano-1-(2-(2-ethoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid Tert-butyl 2-(6-cyano-1-(2-(2-ethoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate 6d (130 mg, 0.217 mmol) was dissolved in 3.5 mL dichloromethane, cooled to 0° C., and 0.7 mL trifluoroacetic acid was added in. After the completion of addition, the mixture was heated to room temperature to react for 3 h. 0.7 mL trifluoroacetic acid and 3.5 mL dichloromethane were supplemented, and the mixture was reacted at room temperature for 15 h. 5 mL water was added into reaction mixture, and the water phase was separated out. The mixture was extracted with dichloromethane (5 mL×3). The organic phases were combined, washed with water (5 mL×3), dried with anhydrous sodium sulfate, and filtered. The filtrate was concentrated under reduced pressure. The obtained residue was purified by silica gel thin layer chromatography (developing solvent: B system) to obtain 2-(6-cyano-1-(2-(2-ethoxyphenyl)-2-((tetrahydro-2H-pyran-4-yl)oxy)ethyl)-5-methyl-2,4-dioxo-1, 2-dihydrothiopheno[2,3-d]pyrimidin-3 (4H)-yl)-2-methylpropionic acid 6 (42 mg, white solid); yield: 35.8%.

MS m/z(ESI): 563.8[M+23]

$^1$H NMR (400 MHz, CDCl$_3$) δ 7.49 (d, J=7.8 Hz, 1H), 7.33-7.27 (m, 1H), 7.01 (t, J=7.3 Hz, 1H), 6.87 (d, J=8.5 Hz, 1H), 5.33 (dd, J=8.4, 3.3 Hz, 1H), 4.28 (s, 1H), 4.08 (dt, J=14.1, 7.1 Hz, 2H), 3.88 (dd, J=19.4, 12.1 Hz, 1H), 3.79-3.71 (m, 1H), 3.71-3.63 (m, 1H), 3.46-3.38 (m, 1H), 3.39-3.26 (m, 2H), 2.65 (s, 3H), 1.81 (d, J=6.6 Hz, 6H), 1.72 (s, 2H), 1.52 (s, 1H), 1.46 (t, J=7.0 Hz, 3H), 1.39-1.30 (m, 1H).

EXAMPLE 7

2-(6-Cyano-1-(2-(2-fluoro-6-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid

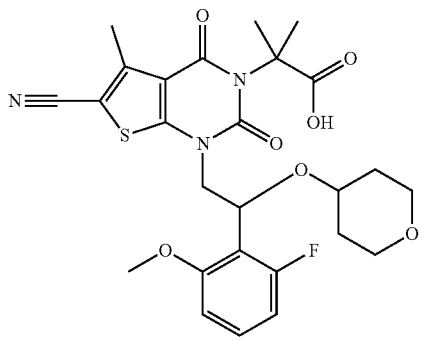

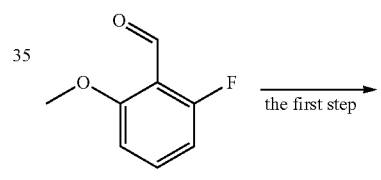

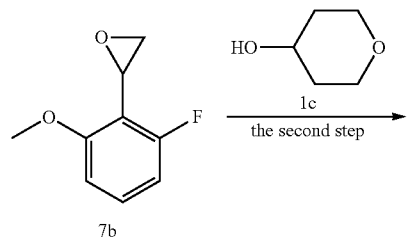

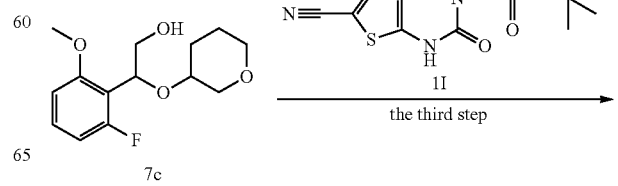

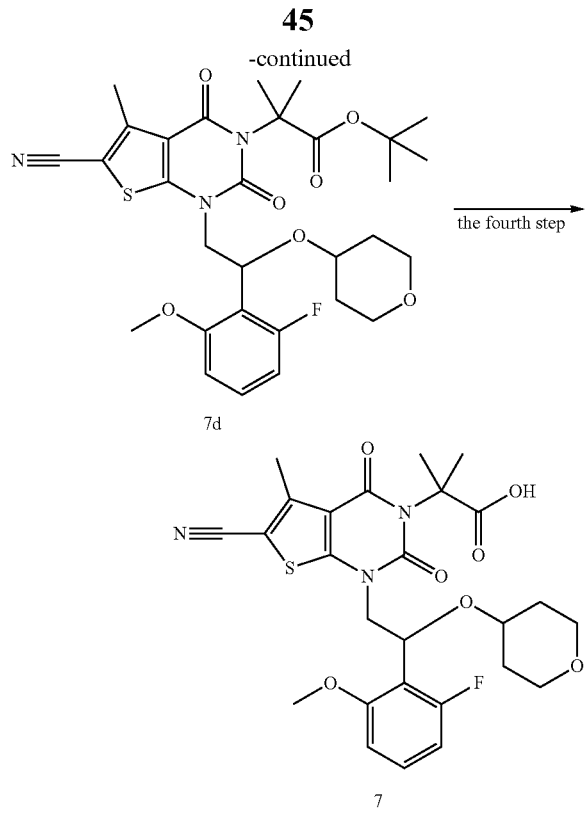

7d

7

The First Step 2-(2-Fluoro-6-methoxyphenyl)ethylene oxide

Tert-butylthiohypoiodite (2.45 g, 12.0 mmol) and potassium hydroxide (1.68 g, 30.0 mmol) were dissolved in 30 mL dimethylsulfoxide, and 2-fluoro-6-methoxybenzaldehyde 7a (1.54 g, 10.0 mmol) was added. The mixture was warmed up to 80° C. to react for 1 h. The reaction mixture was cooled to room temperature, and 100 mL water was added. The mixture was extracted with ethyl acetate (100 mL×2). The organic phases were combined, washed with saturated sodium chloride solution (100 mL×2), dried with anhydrous sodium sulfate, filtered, and concentrated under reduced pressure. The residue was purified by silica gel column chromatography (eluent: A system) to obtain 2-(2-fluoro-6-methoxyphenyl)ethylene oxide 7b (1.2 g, colorless oily product); yield: 72%.

$^1$H NMR (400 MHz, CDCl$_3$) δ 7.25-7.31 (m, 1H), 6.69-6.73 (m, 2H), 4.04-4.08 (m, 1H), 3.91 (s, 3H), 3.30-3.35 (m, 1H), 3.14-3.19 (m, 1H).

The Second Step 2-(2-Fluoro-6-methoxyphenyl)-2-((tetrahydro-2H-pyran-4-yl)oxy)ethanol 2-(2-Fluoro-6-methoxyphenyl)ethylene oxide 7b (1.20 g, 7.14 mmol) was added in tetrahydro-2H-pyran-4-ol 1c (2.19 g, 21.4 mmol) and aluminum trifluoromethanesulfonate (339 mg, 0.714 mmol) with stirring, and the mixture was reacted at room temperature for 2 h. 100 mL water was added into the reaction mixture, and the reaction mixture was extracted with ethyl acetate (100 mL×2). The organic phases were combined, washed with saturated sodium chloride solution (100 mL), dried with anhydrous sodium sulfate, filtered, and concentrated under reduced pressure. The residue was purified by silica gel column chromatography (eluent: A system) to obtain the crude product 2-(2-fluoro-6-methoxyphenyl)-2-((tetrahydro-2H-pyran-4-yl)oxy)ethanol 7c (1.0 g, colorless oily product); yield: 52%.

$^1$H NMR (400 MHz, CDCl$_3$) δ 7.18-7.24 (m, 1H), 6.64-6.71 (m, 2H), 5.17-5.21 (m, 1H), 4.05-4.11 (m, 1H), 3.78-3.96 (m, 5H), 3.60-3.65 (m, 1H), 3.32-3.47 (m, 3H), 2.30-2.36 (m, 1H), 1.67-1.97 (m, 1H), 1.43-1.67 (m, 2H).

The Third Step

Tert-butyl 2-(6-cyano-1-(2-(2-fluoro-6-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate Under nitrogen protection, tert-butyl 2-(6-cyano-5-methyl-2,4-dioxo-1,2-dihydrothieno[2,3-d]pyrimidin-3(4H)-yl)-2-methylpropionate 11 (150 mg, 0.43 mmol), 2-(2-fluoro-6-methoxyphenyl)-2-((tetrahydro-2H-pyran-4-yl)oxy)ethanol 7c (174 mg, 0.65 mmol) and triphenylphosphine (169 mg, 0.65 mmol) were dissolved in 10 mL tetrahydrofuran, and diisopropyl azodicarboxylate (131 mg, 0.65 mmol) was added, and the mixture was reacted at room temperature for 18 h. TLC test showed that most of the raw materials were surplus. The mixture was heated to 80° C. to react for 4 h. The reaction mixture was cooled to room temperature, and 50 mL water was added. The mixture was extracted with ethyl acetate (50 mL×2). The organic phases were combined, washed with saturated sodium chloride solution (50 mL), dried with anhydrous sodium sulfate, filtered, and concentrated under reduced pressure. The residue was purified by silica gel column chromatography (eluent: A system), and the obtained crude product was further purified by silica gel thin layer chromatography (developing solvent: A system) to obtain the crude product tert-butyl 2-(6-cyano-1-(2-(2-fluoro-6-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate 7d (200 mg, white solid); yield: 77.5%.

MS m/z(ESI): 601.9 [M+1]

The Fourth Step 2-(6-Cyano-1-(2-(2-fluoro-6-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid Tert-butyl 2-(6-cyano-1-(2-(2-fluoro-6-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate 7d (200 mg, 0.333 mmol) was dissolved in 5 mL dichloromethane, and 1 mL trifluoroacetic acid was added. The mixture was reacted at room temperature for 1 h. 30 mL water was added into the reaction mixture, which was then extracted with ethyl acetate (30 mL×2). The organic phases were combined, washed with saturated sodium chloride solution (30 mL), dried with anhydrous sodium sulfate, filtered, and concentrated under reduced pressure. The residue was purified by silica gel thin layer chromatography (developing solvent: C system) to obtain 2-(6-cyano-1-(2-(2-fluoro-6-methoxyphenyl)-2-((tetrahydro-2H-pyran-4-yl)

oxy)ethyl)-5-methyl-2,4-dioxo-1,2-dihydrothiopheno[2,3-d]pyrimidin-3(4H)-yl)-2-methylpropionic acid 7 (8 mg, white solid); yield: 18%.

MS m/z(ESI): 568.8[M+23]

$^1$H NMR (400 MHz, CDCl$_3$) δ 7.25-7.29 (m, 1H), 6.70-6.75 (m, 2H), 5.43-5.46 (m, 1H), 4.30-4.33 (m, 2H), 3.87 (s, 3H), 3.60-3.65 (m, 2H), 3.34-3.43 (m, 3H), 2.63 (s, 3H), 1.74-1.83 (m, 7H), 1.60-1.65 (m, 1H), 1.33-1.42 (m, 2H).

EXAMPLE 8

2-(6-Cyano-1-(2-(2-methoxy-5-(trifluoromethyl) phenyl)-2-((tetrahydro-2H-pyran-4-yl)oxy))ethyl)-5-methyl-2,4-dioxo-1,2-dihydrothiopheno[2,3-d]pyrimidin-3(4H)-yl)-2-methylpropionic acid

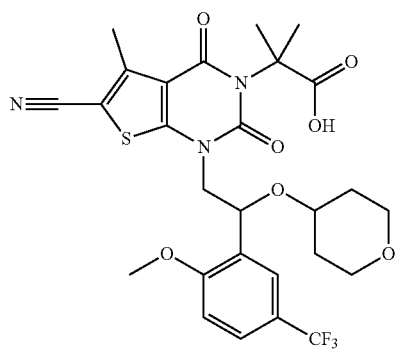

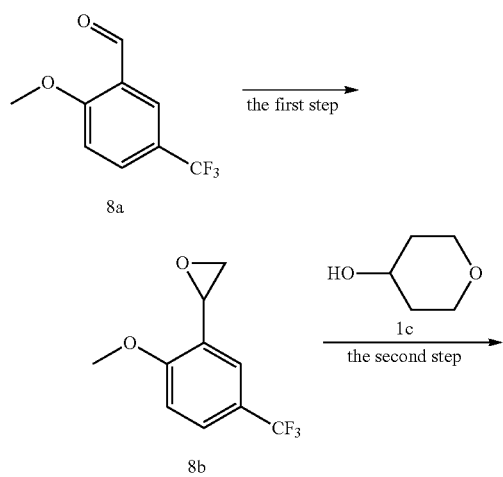

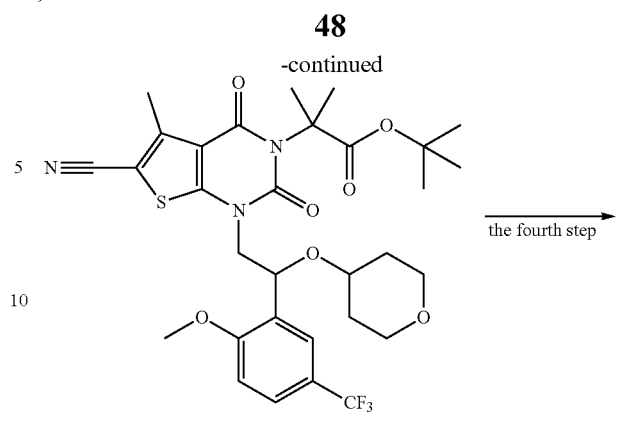

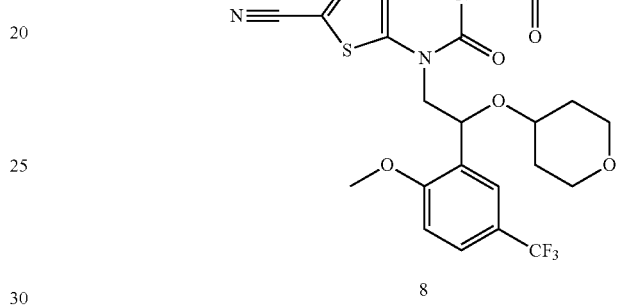

The First Step (2-methoxy-5-(trifluoromethyl))ethylene oxide

Tert-butylthiohypoiodite (360 mg, 1.77 mmol) and potassium hydroxide (247 mg, 4.41 mmol) were dissolved in 30 mL dimethylsulfoxide, and 2-methoxy-5-(trifluoromethyl) benzaldehyde 8a (300 mg, 1.47 mmol) was added, and the mixture was heated to 80° C. to react for 1 h. The reaction mixture was cooled to room temperature, 50 mL water was added, and the reaction mixture was extracted with ethyl acetate (50 mL×2). The organic phases were combined, washed with saturated sodium chloride solution (50 mL), dried with anhydrous sodium sulfate, filtered, and concentrated under reduced pressure, to obtain the rude product (2-methoxy-5-(trifluoromethyl))ethylene oxide 8b (300 mg, colorless oily product); yield: 94%.

$^1$H NMR (400 MHz, CDCl$_3$) δ 7.53 (d, J=0.8 Hz, 1H), 7.43 (s, 1H), 6.94 (d, J=0.8 Hz, 1H), 4.19-4.21 (m, 1H), 3.93 (s, 3H), 3.17-3.19 (m, 1H), 2.64-2.70 (m, 1H).

The Second Step 2-(2-methoxy-5-(trifluoromethyl))-2-((tetrahydro-2H-pyran-4-yl)oxy)ethanol (2-Methoxy-5-(trifluoromethyl))ethylene oxide 8b (300 mg, 1.38 mmol) was added in tetrahydro-2H-pyran-4-ol 1c (423 mg, 4.14 mmol) and aluminum trifluoromethanesulfonate (66 mg, 0.138 mmol) with stirring, and the mixture was reacted at room temperature for 2 h. 50 mL water was added in the reaction mixture, which was then extracted with ethyl acetate (50 mL×2). The organic phases were combined, washed with saturated sodium chloride solution (50 mL), dried with anhydrous sodium sulfate, filtered, and concentrated under reduced pressure. The residue was purified by silica gel column chromatography (eluent: A system) to obtain the 2-(2-methoxy-5-(trifluoromethyl))-2-((tetrahydro-2H-pyran-4-yl)oxy)ethanol 8c (170 mg, colorless oily product); yield: 39%.

$^1$H NMR (400 MHz, CDCl$_3$) δ 7.70 (s, 1H), 7.54 (d, J=0.8 Hz, 1H), 6.94 (d, J=0.8 Hz, 1H), 5.02-5.05 (m, 1H), 3.87-3.98 (m, 5H), 3.70-3.75 (m, 1H), 3.37-3.48 (m, 4H), 2.25-2.28 (m, 1H), 1.90-1.95 (m, 1H), 1.55-1.68 (m, 2H).

The Third Step

Tert-butyl 2-(6-cyano-1-(2-(2-methoxy-5-(trifluoromethyl)phenyl)-2-((tetrahydro-2H-pyran-4-yl)oxy) ethyl)-5-methyl-2,4-dioxo-1,2-dihydrothiopheno[2,3-d]pyrimidin-3(4H)-yl)-2-methylpropionate Under nitrogen protection, tert-butyl 2-(6-cyano-5-methyl-2,4-dioxo-1,2-dihydrothieno[2,3-d]pyrimidin-3 (4H)-yl)-2-methylpropionate 1I (150 mg, 0.44 mmol), 2-(2-methoxy-5-(trifluoromethyl))-2-((tetrahydro-2H-pyran-4-yl)oxy)ethanol 8c (170 mg, 0.53 mmol) and triphenylphosphine (173 mg, 0.66 mmol) were dissolved in 10 mL tetrahydrofuran, and diisopropyl azodicarboxylate (134 mg, 0.66 mmol) was added, and the mixture was heated to 50° C. to react for 3 h. The reaction mixture was cooled to room temperature, and 50 mL water was added, and the reaction mixture was extracted with ethyl acetate (50 mL×2). The organic phases were combined, washed with saturated sodium chloride solution (50 mL), dried with anhydrous sodium sulfate, filtered, and concentrated under reduced pressure. The residue was purified by silica gel column chromatography (eluent: A system), and the obtained crude product was further purified by silica gel thin layer chromatography (developing solvent: A system) to obtain the crude product tert-butyl 2-(6-cyano-1-(2-(2-methoxy-5-(trifluoromethyl)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate 8d (170 mg, white solid); yield: 61%.

MS m/z(ESI): 673.8 [M+23]

The Fourth Step 2-(6-Cyano-1-(2-(2-methoxy-5-(trifluoromethyl) phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid Tert-butyl 2-(6-cyano-1-(2-(2-methoxy-5-(trifluoromethyl)phenyl)-2-((tetrahydro-2H-pyran-4-yl)oxy)ethyl)-5-methyl-2,4-dioxo-1,2-dihydrothiopheno[2,3-d]pyrimidin-3 (4H)-yl)-2-methylpropionate 8d (170 mg, 0.261 mmol) was dissolved in 5 mL dichloromethane, and 1 mL trifluoroacetic acid was added, and the mixture reacted at room temperature for 1 h. 50 mL water was added in the reaction mixture, which was then extracted with ethyl acetate (50 mL×2). The organic phases were combined, washed with saturated sodium chloride solution (50 mL×3), dried with anhydrous sodium sulfate, filtered, and concentrated under reduced pressure. The residue was purified by silica gel thin layer chromatography (developing solvent: A system) to obtain 2-(6-cyano-1-(2-(2-methoxy-5-(trifluoromethyl)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid 8 (5 mg, white solid); yield: 16%.

MS m/z(ESI): 577.8 [M-18]

$^1$H NMR (400 MHz, CDCl$_3$) δ 7.78 (s, 1H), 7.60 (d, J=0.8 Hz, 1H), 6.96 (d, J=0.8 Hz, 1H), 5.30-5.35 (m, 1H), 4.15-4.25 (m, 1H), 3.75-4.00 (m, 4H), 3.60-3.80 (m, 2H), 3.25-3.50 (m, 3H), 2.65 (s, 3H), 1.75-1.87 (m, 8H), 1.53-1.59 (m, 1H), 1.39-1.44 (m, 1H).

EXAMPLE 9

2-(6-Cyano-1-(2-(4-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid

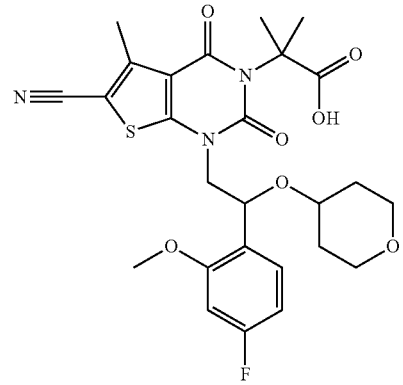

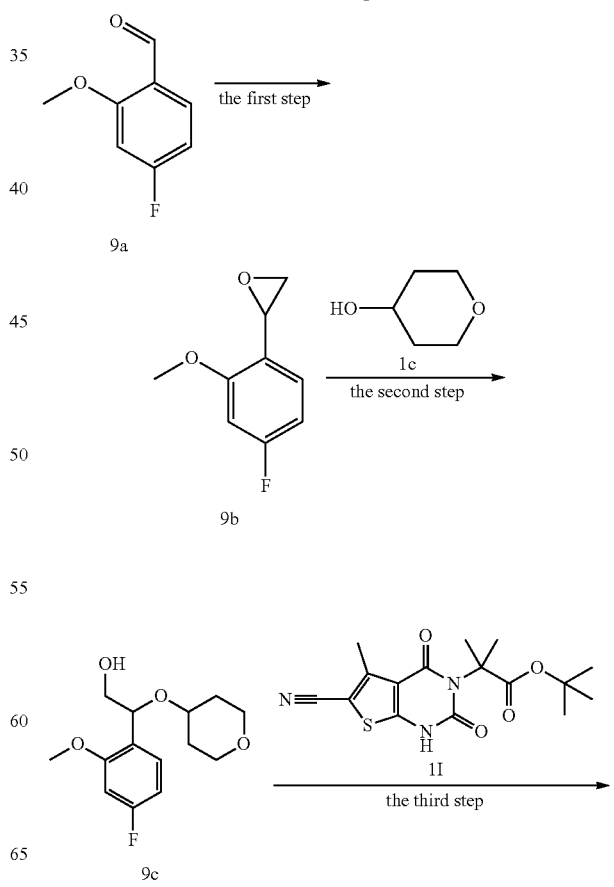

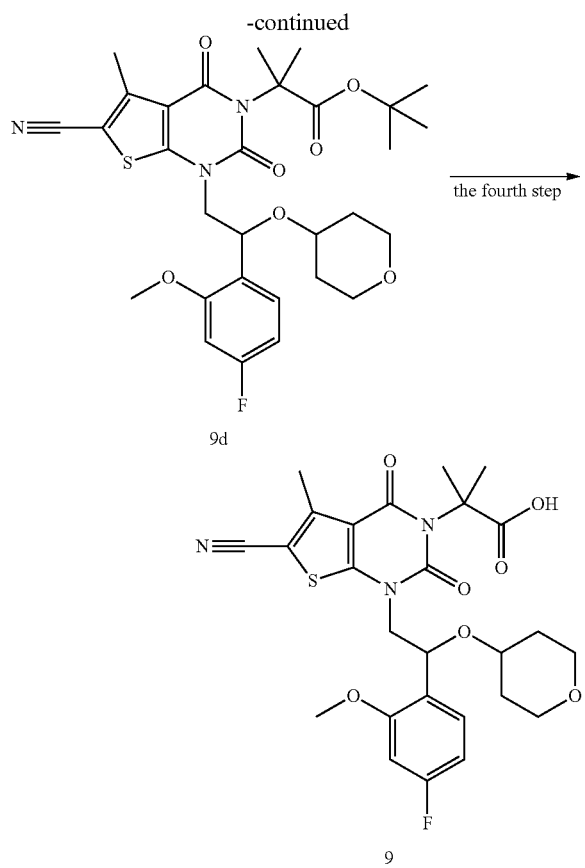

The First Step

2-(4-fluoro-2-methoxyphenyl)ethylene oxide

4-Fluoro-2-methoxybenzaldehyde 9a (0.50 g, 3.25 mmol) was dissolved in 3 mL dimethylsulfoxide, and tert-butylthiohypoiodite (0.79 g, 3.89 mmol) was added. The mixture was heated to 40° C., and potassium hydroxide (0.55 g, 9.75 mmol) was added, and the mixture was reacted at 80° C. for 1.5 h. The reaction mixture was cooled to room temperature, and 10 mL water was added, and the reaction mixture was extracted with ethyl acetate (6 mL×3). The organic phases were combined, successively washed with water (5 mL×2) and saturated sodium chloride solution (5 mL), and concentrated under reduced pressure to obtain 2-(4-fluoro-2-methoxyphenyl)ethylene oxide 9b (0.50 g, light yellow oily product); yield: 91.5%.

MS m/z(ESI): 169.0 [M+1]

The Second Step

2-(4-fluoro-2-methoxyphenyl)-2-((tetrahydro-2H-pyran-4-yl)oxy)ethanol 2-(4-Fluoro-2-methoxyphenyl)ethylene oxide 9b (0.50 g, 2.90 mmol) and tetrahydro-2H-pyran-4-ol 1c (0.90 g, 8.90 mmol) was uniformly mixed, and then aluminum trifluoromethanesulfonate (57 mg, 0.12 mmol) was added, and the mixture was reacted at room temperature for 2 h. 5 mL water was added, and the mixture was extracted with ethyl acetate (5 mL×3). The organic phases were combined, successively washed with water (5 mL×2) and saturated sodium chloride solution (5 mL), and concentrated under reduced pressure. The residue was purified by silica gel column chromatography (eluent: A system) to obtain 2-(4-fluoro-2-methoxyphenyl)-2-((tetrahydro-2H-pyran-4-yl)oxy)ethanol 9c (200 mg, light yellow oily product); yield: 25.5%.

$^1$H NMR (400 MHz, CDCl$_3$) δ 7.49-7.42 (m, 1H), 6.78-6.68 (m, 1H), 6.60 (dd, J=10.7, 2.2 Hz, 1H), 5.28-5.22 (m, 1H), 4.09 (dd, J=14.6, 5.8 Hz, 1H), 4.03-3.90 (m, 1H), 3.83 (s, 3H), 3.73 (dd, J=16.9, 12.2 Hz, 2H), 3.46-3.27 (m, 3H), 2.64 (s, 3H), 1.82 (d, J=10.7 Hz, 6H), 1.73 (s, 2H), 1.52 (d, J=9.0 Hz, 1H), 1.39 (d, J=8.7 Hz, 1H).

The Third Step

Tert-butyl 2-(6-cyano-1-(2-(4-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate Under nitrogen protection, tert-butyl 2-(6-cyano-5-methyl-2,4-dioxo-1,2-dihydrothieno[2,3-d]pyrimidin-3(4H)-yl)-2-methylpropionate 11 (118.8 mg, 0.34 mmol), 2-(4-fluoro-2-methoxyphenyl)-2-((tetrahydro-2H-pyran-4-yl)oxy)ethanol 9c (140 mg, 0.52 mmol) and triphenylphosphine (178.3 mg, 0.68 mmol) were dissolved in 3 mL tetrahydrofuran. The mixture was cooled to 0° C., and diisopropyl azodicarboxylate (137.5 mg, 0.80 mmol) was added.

After the completion of addition, the mixture was heated to room temperature to react for 18 h. The reaction mixture was concentrated under reduced pressure. The obtained residue was purified by silica gel column chromatography (eluent: A system) to obtain the crude product tert-butyl 2-(6-cyano-1-(2-(4-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3 (4H)-yl)-2-methylpropionate 9d (200 mg, bubble-like white solid); yield: 98%.

MS m/z(ESI): 623.8 [M+23]

The Fourth Step

2-(6-Cyano-1-(2-(4-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid Tert-butyl 2-(6-cyano-1-(2-(4-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate 9d (200 mg, 0.33 mmol) was dissolved in 6 mL dichloromethane. The mixture was cooled to 0° C., and 1.2 mL trifluoromethanesulfonic acid was added. After the completion of addition, the mixture was heated to room temperature to react for 4 h. 5 mL water was added into the reaction mixture, which was then extracted with ethyl acetate (5 mL×3). The organic phases were combined, successively washed with water (5 mL×3) until the pH of water phase was about 7. The filtrate was concentrated under reduced pressure. The obtained residue was purified by silica gel column chromatography (eluent: B system) to obtain 2-(6-cyano-1-(2-(4-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionicacid 9 (12 mg, white solid); yield: 9.4%.

MS m/z(ESI): 527.8 [M+1-18]

$^1$H NMR (400 MHz, CDCl$_3$) δ 7.49-7.42 (m, 1H), 6.78-6.68 (m, 1H), 6.60 (dd, J=10.7, 2.2 Hz, 1H), 5.28-5.22 (m,

1H), 4.09 (dd, J=14.6, 5.8 Hz, 1H), 4.03-3.90 (m, 1H), 3.83 (s, 3H), 3.73 (dd, J=16.9, 12.2 Hz, 2H), 3.46-3.27 (m, 3H), 2.64 (s, 3H), 1.82 (d, J=10.7 Hz, 6H), 1.73 (s, 2H), 1.52 (d, J=9.0 Hz, 1H), 1.39 (d, J=8.7 Hz, 1H).

Example 10

2-(6-Cyano-1-(2-(3-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid

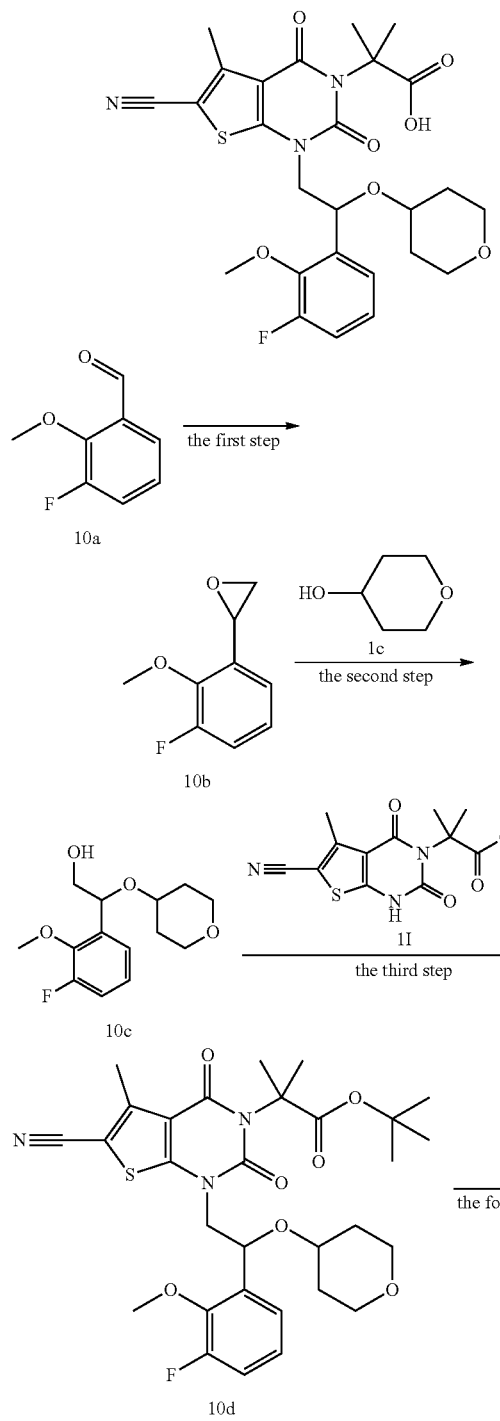

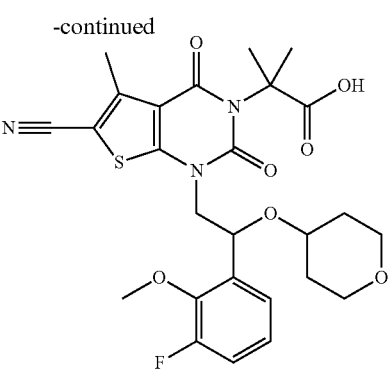

The First Step 2-(3-fluoro-2-methoxyphenyl)ethylene oxide

Tert-butylthiohypoiodite (1.23 g, 6.0 mmol) and potassium hydroxide (840 mg, 15.0 mmol) were dissolved in 30 mL dimethylsulfoxide, and 3-fluoro-2-methoxybenzaldehyde 10a (770 mg, 5.0 mmol) was added. The mixture was heated to 80° C. to react for 1 h. The reaction mixture was cooled to room temperature, 50 mL water was added, and the reaction mixture was extracted with ethyl acetate (50 mL×2). The organic phases were combined, washed with saturated sodium chloride solution (50 mL), dried with anhydrous sodium sulfate, filtered, and concentrated under reduced pressure to obtain the crude product 2-(3-fluoro-2-methoxyphenyl)ethylene oxide 10b (840 mg, colorless oily product); yield: 100%.

$^1$H NMR (400 MHz, CDCl3) δ 6.98-7.08 (m, 2H), 6.90-6.95 (m, 1H), 4.17-4.19 (m, 1H), 3.99 (s, 3H), 3.15-3.18 (m, 1H), 2.70-2.74 (m, 1H).

The Second Step 2-(3-Fluoro-2-methoxyphenyl)-2-((tetrahydro-2H-pyran-4-yl)oxy)ethanol 2-(3-Fluoro-2-methoxyphenyl)ethylene oxide 10b (840 mg, 5.0 mmol) was added into tetrahydro-2H-pyran-4-ol 1c (1.53 g, 15.0 mmol) and aluminum trifluoromethanesulfonate (237 mg, 0.5 mmol) with stirring, and the mixture was reacted at room temperature for 2 h. 50 mL water was added in the reaction mixture, which was then extracted with ethyl acetate (50 mL×2). The organic phases were combined, washed with saturated sodium chloride solution (50 mL), dried with anhydrous sodium sulfate, filtered, and concentrated under reduced pressure. The residue was purified by silica gel column chromatography (eluent: A system) to obtain the crude product 2-(3-fluoro-2-methoxyphenyl)-2-((tetrahydro-2H-pyran-4-yl)oxy)ethanol 10c (174 mg, colorless oily product); yield: 13%.

$^1$H NMR (400 MHz, CDCl$_3$) δ 7.10-7.20 (m, 1H), 7.01-7.05 (m, 2H), 5.01-5.04 (m, 1H), 3.90-4.00 (m, 5H), 3.36-3.63 (m, 5H), 2.25-2.30 (m, 1H), 1.76-2.02 (m, 1H), 1.70-1.75 (m, 1H), 1.60-1.65 (m, 1H).

The Third Step

Tert-butyl 2-(6-cyano-1-(2-(3-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate Under nitrogen protection, tert-butyl 2-(6-cyano-5-methyl-2,4-dioxo-1,2-dihydrothieno[2,3-d]pyrimidin-3(4H)-yl)-2-methylpropionate 1l (150 mg, 0.43 mmol), 2-(3-fluoro-2-methoxyphenyl)-2-((tetrahydro-2H-pyran-4-yl)oxy)ethanol 10c (174 mg, 0.65 mmol), triphenylphosphine (169 mg, 0.65 mmol) and diisopropyl azodicarboxylate (131 mg, 0.65 mmol) were dissolved in 10 mL tetrahydrofuran, and the mixture was reacted at room temperature for 18 h. 50 mL water was added in the reaction mixture, which was then extracted with ethyl acetate (50 mL×2). The organic phases were combined, washed with saturated sodium chloride solution (50 mL), dried with anhydrous sodium sulfate, filtered, and concentrated under reduced pressure. The residue was purified by silica gel column chromatography (eluent: A system), and the obtained crude product was further purified by silica gel thin layer chromatography (developing solvent: A system) to obtain the crude product tert-butyl 2-(6-cyano-1-(2-(3-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate 10d (200 mg, white solid); yield: 78%.

MS m/z(ESI): 623.8 [M+23]

The Fourth Step

2-(6-Cyano-1-(2-(3-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid Tert-butyl 2-(6-cyano-1-(2-(3-fluoro-2-methoxyphenyl)-2-((tetrahydro-2H-pyran-4-yl) oxy)ethyl)-5-methyl-2,4-dioxo-1,2-dihydrothiopheno[2,3-d]pyrimidin-3(4H)-yl)-2-methylpropionate 10d (200 mg, 0.333 mmol) was dissolved in 5 mL dichloromethane, and 1 mL trifluoroacetic acid was added. The mixture was reacted at room temperature for 3 h. 50 mL water was added in the reaction mixture, which was then extracted with ethyl acetate (50 mL×2). The organic phases were combined, washed with saturated sodium chloride solution (50 mL), dried with anhydrous sodium sulfate, filtered, and concentrated under reduced pressure. The residue was purified by silica gel thin layer chromatography (developing solvent: A system) to obtain 2-(6-cyano-1-(2-(3-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid 10 (30 mg, white solid); yield: 17%.

MS m/z(ESI): 568.8[M+23]

$^1$H NMR (400 MHz, CDCl$_3$) δ 7.24-7.27 (m, 1H), 7.05-7.10 (m, 2H), 5.25-5.28 (m, 1H), 4.10-4.16 (m, 1H), 4.02 (s, 3H), 3.96-4.00 (m, 1H), 3.50-3.70 (m, 2H), 3.32-3.45 (m, 3H), 2.66 (s, 3H), 1.85 (s, 3H), 1.83 (s, 3H), 1.60-1.70 (m, 1H), 1.40-1.55 (m, 1H), 1.30-1.40 (m, 2H).

EXAMPLE 11

(R)-2-(6-Cyano-1-(2-(5-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid

EXAMPLE 12

(S)-2-(6-Cyano-1-(2-(5-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid

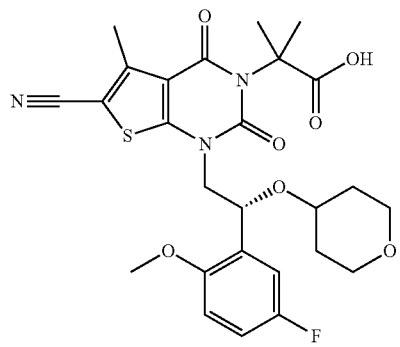

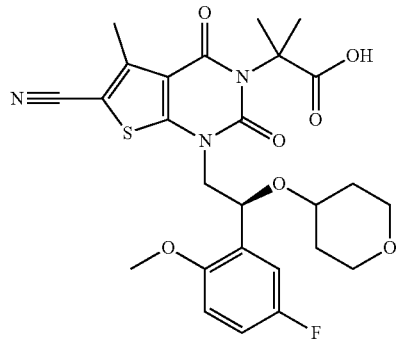

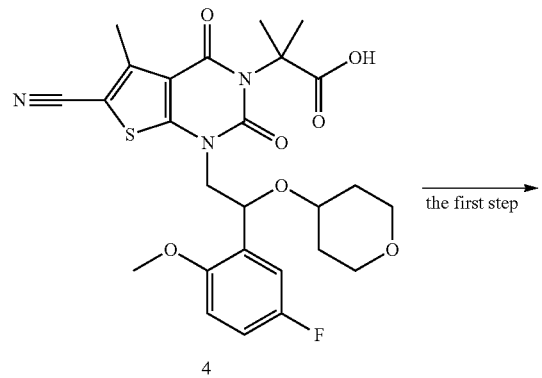

the first step →

4

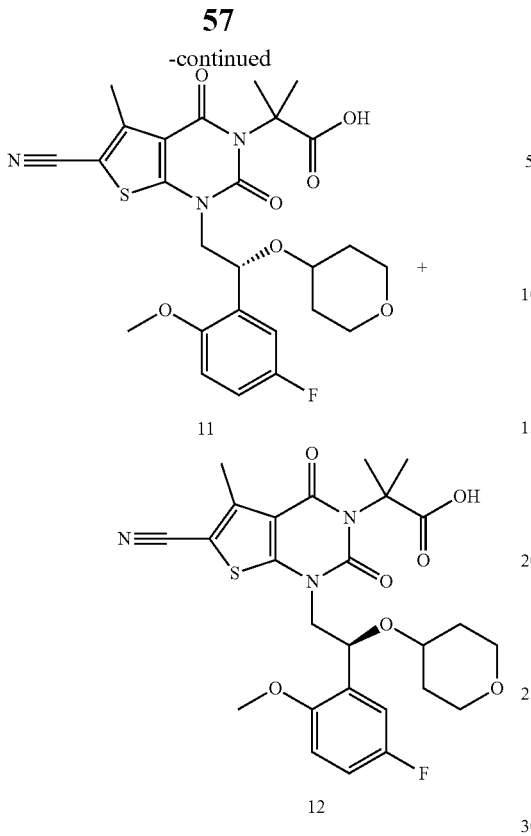

11

12

The First Step (R)-2-(6-Cyano-1-(2-(5-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid (S)-2-(6-Cyano-1-(2-(5-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid The 2-(6-cyano-1-(2-(5-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid 4 (160 mg, 0.29 mmol) obtained in Example 4 was further separated by supercritical fluid chromatography (SFC) using preparative equipment and chiral column to separate chiral isomers (chiral column ChiralPak AD, 250× 30 mm I.D., 5 μm, 60 mL/min; mobile phase A for CO₂ and B for EtOH), to obtain (R)-2-(6-cyano-1-(2-(5-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid 11 (74.29 mg, white solid); yield: 46.4%, 100% ee, retention time: 2.737 min; (S)-2-(6-cyano-1-(2-(5-fluoro-2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid 12 (59.96 mg, white solid); yield: 37.4%, 99.5% ee, retention time: 2.748 min.

11

MS m/z(ESI): 567.8 [M+23]

¹H NMR (400 MHz, CDCl₃) δ 7.23 (dd, J=9.0, 2.8 Hz, 1H), 7.02-6.95 (m, 1H), 6.79 (dd, J=8.9, 4.2 Hz, 1H), 5.32-5.25 (m, 1H), 4.11 (dd, J=13.1, 10.2 Hz, 1H), 4.05-3.87 (m, 1H), 3.81 (s, 3H), 3.71 (d, J=20.8 Hz, 2H), 3.49-3.41 (m, 1H), 3.33 (dd, J=22.9, 4.2 Hz, 2H), 2.64 (s, 3H), 1.83 (d, J=11.3 Hz, 6H), 1.79-1.71 (m, 2H), 1.57 (ddd, J=6.4, 5.0, 2.3 Hz, 1H), 1.45-1.34 (m, 1H).

12

MS m/z(ESI): 567.8 [M+23]

¹H NMR (400 MHz, CDCl₃) δ 6 7.21 (d, J=11.8 Hz, 1H), 6.90-7.02 (m, 1H), 6.79 (dd, J=9.0, 4.0 Hz, 1H), 5.33-5.25 (m, 1H), 4.15-4.05 (m, 1H), 4.03-3.92 (m, 1H), 3.82 (s, 3H), 3.78-3.70 (m, 2H), 3.44 (s, 1H), 3.35 (dd, J=18.7, 9.1 Hz, 2H), 2.65 (s, 3H), 1.83 (d, J=11.6 Hz, 6H), 1.78-1.72 (m, 2H), 1.61-1.51 (m, 1H), 1.47-1.32 (m, 1H).

EXAMPLE 13

2-(6-Cyano-1-(2-(2-(cyclopropylmethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid

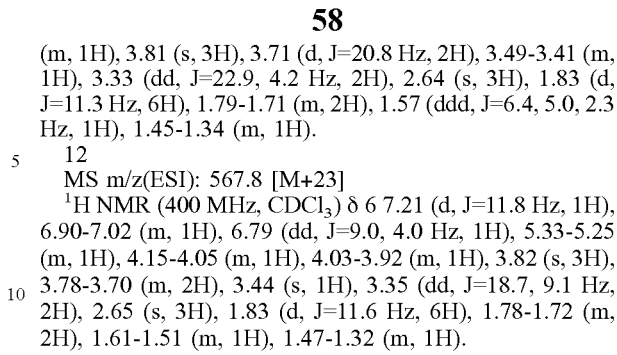

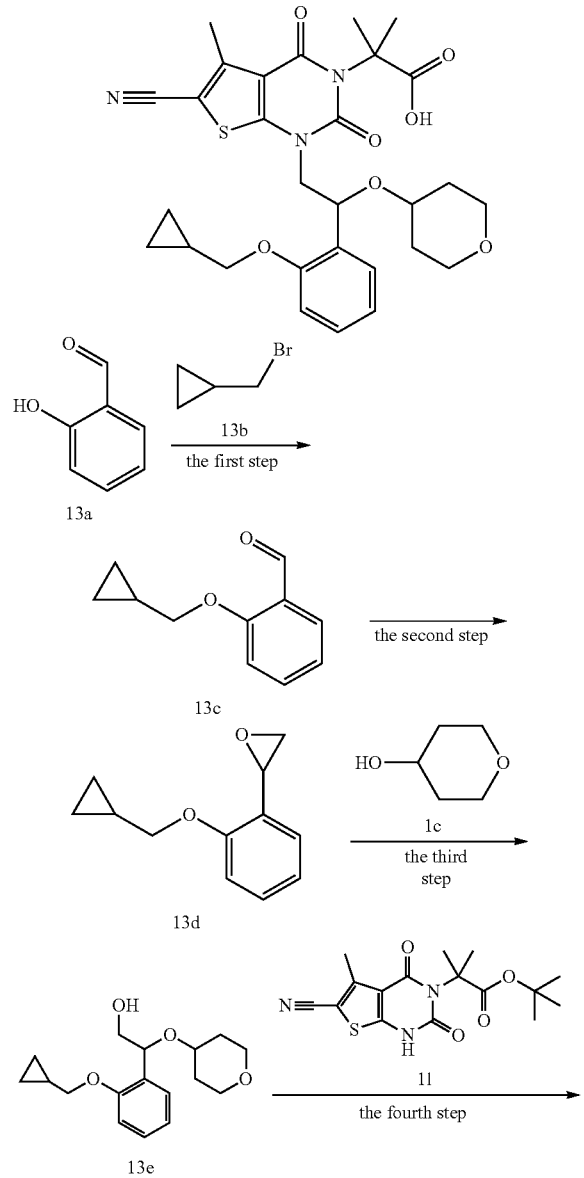

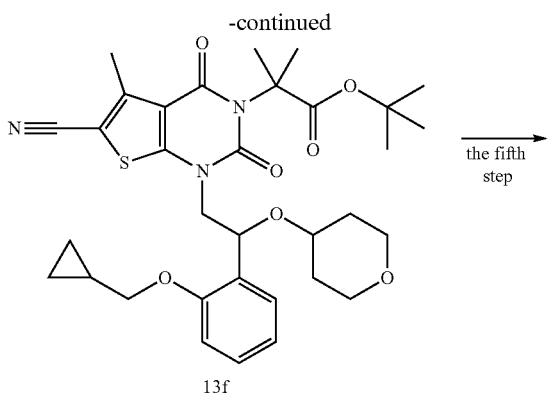

13f

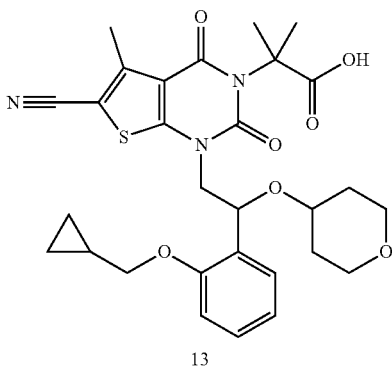

13

The First Step

2-(Cyclopropylmethoxy)benzaldehyde 2-(Hydroxy)benzaldehyde 13a (1.22 g, 10.0 mmol), (bromomethyl)cyclopropane 13b (1.35 g, 10.0 mmol) and potassium carbonate (2.76 g, 20.0 mmol) were dissolved in 20 mL N,N-dimethylformamide, and the mixture was heated to 50° C. to react for 6 h. The reaction mixture was cooled to room temperature, and 50 mL water was added, and the reaction mixture was extracted with ethyl acetate (50 mL×2). The organic phases were combined, washed with saturated sodium chloride solution (50 mL×2), dried with anhydrous sodium sulfate, filtered, concentrated under reduced pressure. The residue was purified by silica gel column chromatography (eluent: A system) to obtain 2-(cyclopropylmethoxy)benzaldehyde 13c (1.50 g, colorless oily product); yield: 85%.

$^1$H NMR (400 MHz, CDCl$_3$) δ 10.57 (s, 1H), 7.84 (d, J=8.0 Hz, 1H), 7.52 (t, J=8.0 Hz, 1H), 7.02 (t, J=8.0 Hz, 1H), 6.95 (d, J=8.0 Hz, 1H),3.94 (d, J=8.0 Hz, 2H), 1.30-1.35 (m, 1H), 0.65-0.70 (m, 2H), 0.35-0.40 (m, 2H).

The Second Step

2-(2-(Cyclopropylmethoxy)phenyl)ethylene oxide

Tert-butylthiohypoiodite (1.39 g, 6.82 mmol) and potassium hydroxide (955 mg, 17.04 mmol) were dissolved in 30 mL dimethylsulfoxide, and 2-(cyclopropylmethoxy)benzaldehyde 13c (1.00 g, 5.68 mmol) was added, and the mixture was heated to 80° C. to react for 1 h. The reaction mixture was cooled to room temperature, and 50 mL water was added, and the reaction mixture was extracted with ethyl acetate (50 mL×2). The organic phases were combined, washed with saturated sodium chloride solution (50 mL), dried with anhydrous sodium sulfate, filtered, concentrated under reduced pressure to obtain the crude product 2-(2-(cyclopropylmethoxy)phenyl)ethylene oxide 13d (1.00 g, colorless oily product); yield: 100%.

$^1$H NMR (400 MHz, CDCl$_3$) δ7.24 (t, J=8.0 Hz, 1H), 7.15 (d, J=8.0 Hz, 1H), 6.94 (t, J=8.0 Hz, 1H), 6.86 (d, J=8.0 Hz, 1H), 4.30 (t, J=4.0 Hz, 1H), 3.83-3.93 (m, 2H), 3.16-3.19 (m, 1H), 2.73-2.75 (m, 1H), 1.26-1.32 (m, 1H), 0.62-0.67 (m, 2H), 0.36-0.39 (m, 2H).

The Third Step

2-(2-(Cyclopropylmethoxy)phenyl)-2-((tetrahydro-2H-pyran-4-yl)oxy)ethanol 2-(2-(Cyclopropylmethoxy)phenyl)ethylene oxide 13d (1.00 g, 5.26 mmol) was added in tetrahydro-2H-pyran-4-ol 1c (1.62 g, 15.08 mmol) and aluminum trifluoromethanesulfonate (249 mg, 0.526 mmol) with stirring, and the mixture was reacted at room temperature for 3 h. 50 mL water was added in the reaction mixture, which was then extracted with ethyl acetate (50 mL×2). The organic phases were combined, washed with saturated sodium chloride solution (50 mL), dried with anhydrous sodium sulfate, filtered, and concentrated under reduced pressure. The residue was purified by silica gel column chromatography (eluent: A system) to obtain the crude product 2-(2-(cyclopropylmethoxy)phenyl)-2-((tetrahydro-2H-pyran-4-yl)oxy) ethanol 13e (70 mg, colorless oily product); yield: 33%.

$^1$H NMR (400 MHz, CDCl$_3$) δ7.42 (d, J=8.0 Hz, 1H), 7.25 (t, J=8.0 Hz, 1H), 6.97 (t, J=8.0 Hz, 1H), 6.83 (d, J=8.0 Hz, 1H), 5.10-5.20 (m, 1H), 3.90-4.00 (m, 2H), 3.60-3.85 (m, 3H), 3.34-3.57 (m, 3H), 2.31-2.34 (m, 1H), 2.00-2.05 (m, 1H), 1.60-1.80 (m, 3H), 1.25-1.30 (m, 2H), 0.60-0.65 (m, 2H), 0.30-0.35 (m, 2H).

The Fourth Step

Tert-butyl 2-(6-cyano-1-(2-(2-(cyclopropylmethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate Under nitrogen protection, tert-butyl 2-(6-cyano-5-methyl-2,4-dioxo-1,2-dihydrothieno[2,3-d]pyrimidin-3 (4H)-yl)-2-methylpropionate 11 (324 mg, 0.93 mmol), 2-(2-(cyclopropylmethoxy)phenyl)-2-((tetrahydro-2H-pyran-4-yl)oxy) ethanol 13e (300 mg, 1.03 mmol), triphenylphosphine (406 mg, 1.55 mmol) and diisopropyl azodicarboxylate (314 mg, 1.55 mmol) were dissolved in 15 mL tetrahydrofuran, and the mixture was heated to 50° C. to react for 8 h. 50 mL water was added in the reaction mixture, which was then extracted with ethyl acetate (50 mL×2). The organic phases were combined, washed with saturated sodium chloride solution (50 mL), dried with anhydrous sodium sulfate, filtered, and concentrated under reduced pressure. The residue was purified by silica gel column chromatography (eluent: A system), and the obtained crude product was further purified by silica gel thin layer chromatography (developing solvent: A system) to obtain the crude product tert-butyl 2-(6-cyano-1-(2-(2-(cyclopropylmethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate 13f (500 mg, white solid); yield: 78%.

MS m/z(ESI): 623.9 [M+1]

The Fifth Step 2-(6-Cyano-1-(2-(2-(cyclopropylmethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid Tert-butyl 2-(6-cyano-1-(2-(2-(cyclopropylmethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate 13f (500 mg, 0.80 mmol) was dissolved in 5 mL dichloromethane, and 1 mL trifluoroacetic acid was added, and the mixture was reacted at room temperature for 2 h. 50 mL water was added in the reaction mixture, which was then extracted with ethyl acetate (50 mL×2). The organic phases were combined, washed with saturated sodium chloride solution (50 mL), dried with anhydrous sodium sulfate, filtered, and concentrated under reduced pressure. The residue was purified by silica gel column chromatography (eluent: A system) to obtain 2-(6-cyano-1-(2-(2-(cyclopropylmethoxy)phenyl)-2-((tetrahydro-2H-pyran-4-yl)oxy)ethyl)-5-methyl-2,4-dioxo-1,2-dihydrothiopheno[2,3-d]pyrimidin-3 (4H)-yl)-2-methylpropionic acid 13 (30 mg, white solid); yield: 7%.

MS m/z(ESI): 589.9[M+23]

$^1$H NMR (400 MHz, CDCl$_3$) δ 7.51 (d, J=8.0 Hz, 1H), 7.31 (t, J=8.0 Hz, 1H), 7.02 (t, J=8.0 Hz, 1H), 6.87 (d, J=8.0 Hz, 1H), 5.35-5.40 (m, 1H), 4.05-4.15 (m, 2H), 3.84-3.93 (m, 2H), 3.66-3.78 (m, 2H), 3.30-3.45 (m, 3H), 2.66 (s, 3H), 1.84 (s, 3H), 1.81 (s, 3H), 1.73-1.80 (m, 2H), 1.52-1.57 (m, 1H), 1.27-1.38 (m, 3H), 0.66-0.69 (m, 2H), 0.35-0.39 (m, 2H).

EXAMPLE 14

2-(6-Cyano-1-(2-(5-fluoro-2-(2-fluoroethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid

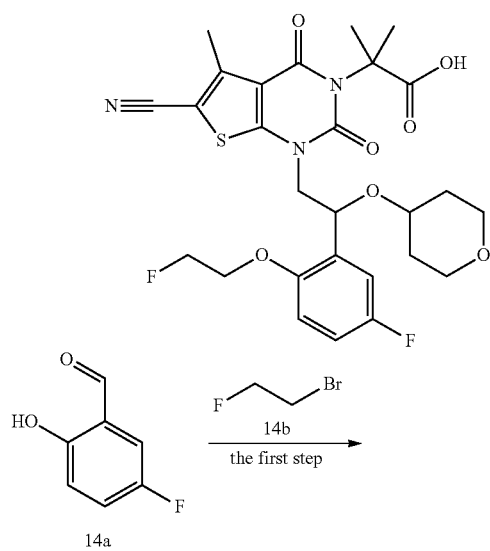

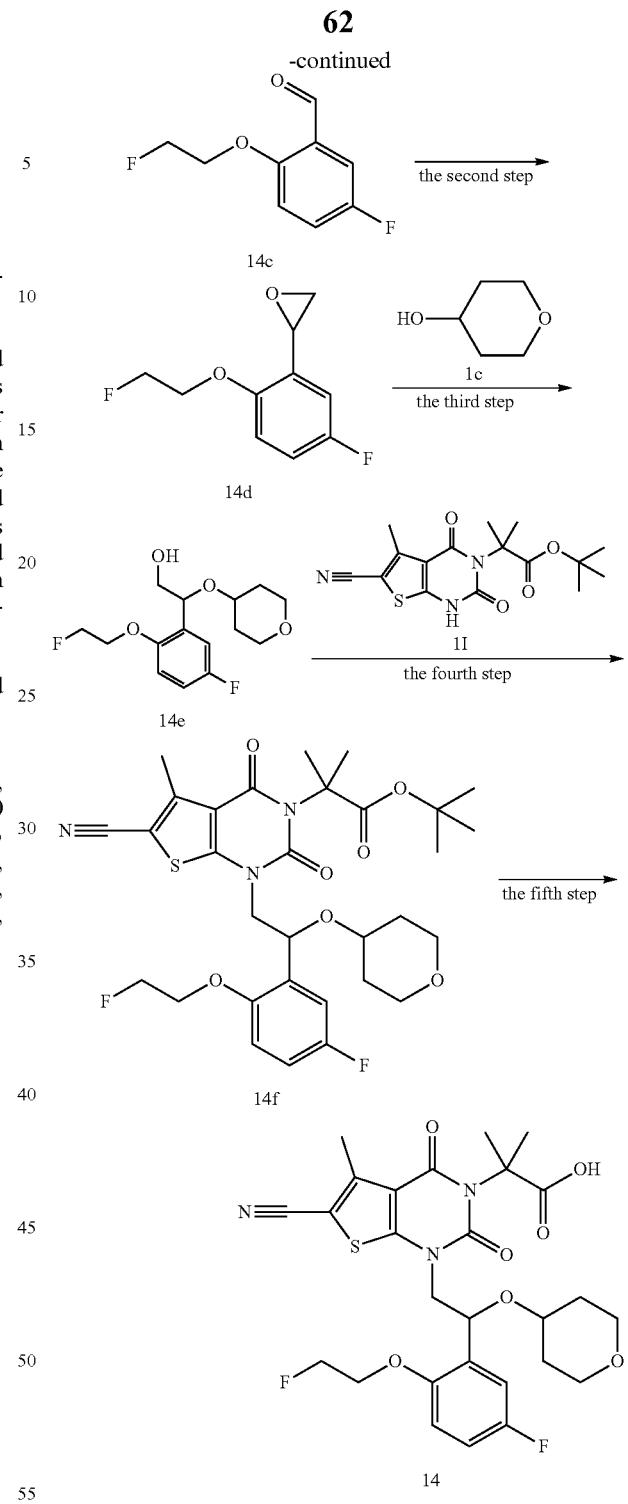

The First Step

5-Fluoro-2-(2-fluoroethoxy)benzaldehyde

5-Fluoro-2-hydroxybenzaldehyde 14a (2.80 g, 20.0 mmol) was dissolved in 30 mL N,N-dimethylformamide, and potassium carbonate (4.14 g, 30.0 mmol) was added. The mixture was stirred at room temperature for 5 min, and 1-bromo-2-fluoroethane 14b (3.5 mL, 50.0 mmol) was added, and the mixture was heated to 65° C. to react for 1 h. The reaction mixture was cooled to room temperature, and 100 mL water was added, and the reaction mixture was extracted with ethyl acetate (50 mL×3). The organic phases were combined, washed with water (30 mL×3), and concentrated under reduced pressure. The residue was purified by silica gel column chromatography (eluent: A system) to obtain 5-fluoro-2-(2-fluoroethoxy)benzaldehyde 14c (3.60 g, light yellow solid); yield: 97%.

$^1$H NMR (400 MHz, CDCl$_3$) δ 10.47 (d, J=3.2 Hz, 1H), 7.52 (dd, J=8.2, 3.3 Hz, 1H), 7.30-7.22 (m, 1H), 6.97 (dd, J=9.1, 3.8 Hz, 1H), 4.87 (dd, J=4.8, 3.3 Hz, 1H), 4.75 (dd, J=4.8, 3.3 Hz, 1H), 4.40-4.34 (m, 1H), 4.33-4.27 (m, 1H).

The Second Step 2-(5-Fluoro-2-(2-fluoroethoxy)phenyl)ethylene oxide

Tert-butylthiohypoiodite (4.5 g, 22.03 mmol) was dissolved in 12 mL dimethylsulfoxide, and potassium hydroxide (3.0 g, 55.08 mmol) was added. The mixture was stirred for 5 min, and 5-fluoro-2-(2-fluoroethoxy)benzaldehyde 14c (3.4 g, 18.36 mmol) was added. The mixture was heated to 70° C. to react for 1.5 h. The reaction mixture was cooled to room temperature, and 100 mL water was added, and the reaction mixture was extracted with ethyl acetate (30 mL×3). The organic phases were combined, washed with water (30 mL×2), dried with anhydrous sodium sulfate, filtered, and concentrated under reduced pressure to obtain 2-(5-fluoro-2-(2-fluoroethoxy) phenyl)ethylene oxide 14d (3.2 g, colorless oily product); yield: 87%.

MS m/z(ESI): 200.9 [M+1]

The Third Step 2-(5-Fluoro-2-(2-fluoroethoxy) phenyl)-2-((tetrahydro-2H-pyran-4-yl)oxy)ethanol Tetrahydro-2H-pyran-4-ol 1c (3.2 g, 31.2 mmol) and aluminum trifluoromethanesulfonate (296 mg, 0.63 mmol) were stirred for 5 min, and 2-(5-fluoro-2-(2-fluoroethoxy) phenyl)ethylene oxide 14d (2.50 g, 12.5 mmol) was added, and the mixture was reacted at room temperature for 1.5 h. 20 mL water was added, and the mixture was extracted with ethyl acetate (30 mL×3). The organic phases were combined, washed with water (20 mL×2), dried with anhydrous sodium sulfate, filtered, and concentrated under reduced pressure. The residue was purified by silica gel column chromatography (eluent: A system) to obtain 2-(5-fluoro-2-(2-fluoroethoxy) phenyl)-2-((tetrahydro-2H-pyran-4-yl) oxy)ethanol 14e (1.9 g, colorless oily product); yield: 50.4%.

$^1$H NMR (400 MHz, CDCl$_3$) δ 7.14 (dd, J=9.1, 3.1 Hz, 1H), 6.97-6.86 (m, 1H), 6.77 (dd, J=8.9, 4.2 Hz, 1H), 5.03 (dd, J=7.8, 3.1 Hz, 1H), 4.78 (dd, J=7.5, 3.4 Hz, 1H), 4.66 (dd, J=7.3, 3.4 Hz, 1H), 4.22 (dd, J=4.8, 3.2 Hz, 1H), 4.19-4.13 (m, 1H), 3.94 (dd, J=8.0, 3.7 Hz, 2H), 3.81 (d, J=5.2 Hz, 1H), 3.73-3.62 (m, 1H), 3.54-3.45 (m, 1H), 3.39 (dd, J=8.7, 6.3 Hz, 2H), 2.46 (dd, J=9.4, 3.6 Hz, 1H), 1.98 (ddd, J=12.9, 5.2, 3.2 Hz, 1H), 1.80-1.72 (m, 1H), 1.67-1.57 (m, 2H).

The Fourth Step

Tert-butyl 2-(6-cyano-1-(2-(5-fluoro-2-(2-fluoroethoxy)phenyl)-2-((tetrahydro-2H-pyran-4-yl)oxy) ethyl)-5-methyl-2,4-dioxo-1,2-dihydrothiopheno[2,3-d]pyrimidin-3 (4H)-yl)-2-methylpropionate Under nitrogen protection, tert-butyl 2-(6-cyano-5-methyl-2,4-dioxo-1,2-dihydrothieno [2,3-d]pyrimidin-3 (4H)-yl)-2-methylpropionate 11 (300 mg, 0.86 mmol) and triphenylphosphine (450 mg, 1.72 mmol) were dissolved in 5 mL tetrahydrofuran, and 2-(5-fluoro-2-(2-fluoroethoxy) phenyl)-2-((tetrahydro-2H-pyran-4-yl)oxy)ethanol 14e (389 mg, 1. 29 mmol) in 3 mL tetrahydrofuran was added. Diisopropyl azodicarboxylate (158.6 μL, 0.80 mmol) was further added. After completion of adding, the mixture was reacted at 33° C. for 8 h. The reaction mixture was concentrated under reduced pressure. The obtained residue was purified by silica gel column chromatography (eluent: A system) to obtain tert-butyl 2-(6-cyano-1-(2-(5-fluoro-2-(2-fluoroethoxy)phenyl)-2-((tetrahydro-2H-pyran-4-yl)oxy) ethyl)-5-methyl-2,4-dioxo-1,2-dihydrothiopheno[2,3-d]pyrimidin-3(4H)-yl)-2-methylpropionate 14f (80 mg, yellow oily product); yield: 15%.

MS m/z(ESI): 633.9 [M+1]

The Fifth Step 2-(6-Cyano-1-(2-(5-fluoro-2-(2-fluoroethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid Tert-butyl 2-(6-cyano-1-(2-(5-fluoro-2-(2-fluoroethoxy) phenyl)-2-((tetrahydro-2H-pyran-4-yl)oxy)ethyl)-5-methyl-2,4-dioxo-1,2-dihydrothiopheno[2,3-d]pyrimidin-3 (4H)-yl)-2-methylpropionate 14f (80 mg, 0.126 mmol) was dissolved in 5 mL dichloromethane, and 1 mL trifluoromethanesulfonic acid was added. After the completion of addition, the mixture was heated to room temperature and reacted for 8 h. 5 mL water was added in the reaction mixture, which was then extracted with dichloromethane (3 mL×2). The organic phases were combined, washed with water (3 mL×2), and the filtrate was concentrated under reduced pressure. The obtained residue was purified by silica gel column chromatography (eluent: B system) to obtain 2-(6-cyano-1-(2-(5-fluoro-2-(2-fluoro ethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid 14 (12 mg, off-white solid); yield: 16.4%.

MS m/z(ESI): 599.8[M+23]

$^1$H NMR (400 MHz, CDCl$_3$) δ 7.23 (dd, J=8.6, 3.0 Hz, 1H), 7.00 (td, J=8.1, 3.3 Hz, 1H), 6.83 (dd, J=9.0, 4.1 Hz, 1H), 5.32 (d, J=13.3 Hz, 1H), 4.85 (dd, J=43.2, 34.0 Hz, 3H), 4.42-4.12 (m, 2H), 3.82-3.61 (m, 3H), 3.47-3.25 (m, 3H), 2.66 (s, 3H), 1.83 (d, J=19.2 Hz, 6H), 1.75 (s, 2H), 1.54 (d, J=8.2 Hz, 1H), 1.34 (d, J=8.8 Hz, 1H).

EXAMPLE 15

2-(6-Cyano-1-(2-(2-ethoxy-5-fluorophenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid

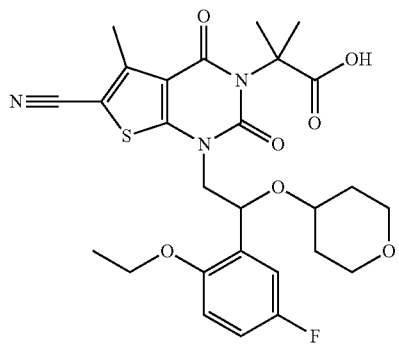

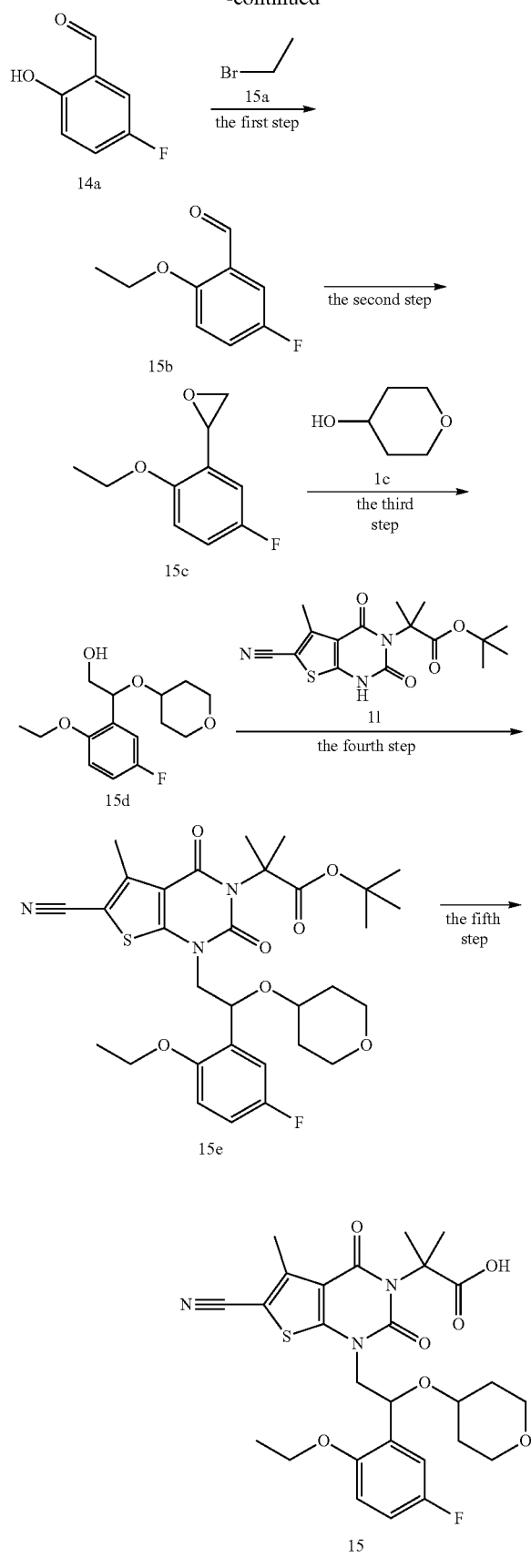

The First Step

5-Fluoro-2-(2-fluoroethoxy)benzaldehyde

5-Fluoro-2-hydroxybenzaldehyde 14a (1.40 g, 10.0 mmol), bromoethane 15a (1.31 g, 12.0 mmol) and potassium carbonate (2.76 g, 20.0 mmol) were dissolved in 20 mL N,N-dimethylformamide, and the mixture was reacted at room temperature for 18 h. 50 mL water was added in the reaction mixture, which was then extracted with ethyl acetate (50 mL×2). The organic phases were combined, washed with saturated sodium chloride solution (50 mL), dried with anhydrous sodium sulfate, filtered, and concentrated under reduced pressure. The residue was purified by silica gel column chromatography (eluent: A system) to obtain 2-ethoxy-5-fluorobenzaldehyde 15b (1.30 g, white solid); yield: 78%.

$^1$H NMR (400 MHz, CDCl$_3$) δ 10.46 (d, J=4.0 Hz, 1H), 7.49-7.53 (m, 1H), 7.23-7.27 (m, 1H), 6.93-6.96 (m, 1H), 4.15 (q, J=8.0, 16.0 Hz, 2H), 1.48 (t, J=8.0 Hz, 3H).

The Second Step

2-(2-Ethoxy-5-fluorophenyl)ethylene oxide

Tert-butylthiohypoiodite (1.89 g, 9.28 mmol) and potassium hydroxide (1.30 g, 23.2 mmol) were dissolved in 30 mL dimethylsulfoxide, and 2-ethoxy-5-fluorobenzaldehyde 15b (1.30 g, 7.73 mmol) was added. The mixture was heated to 80° C. to react for 1 h. The reaction mixture was cooled to room temperature, and 50 mL water was added, and the mixture was extracted with ethyl acetate (50 mL×2). The organic phases were combined, washed with saturated sodium chloride solution (50 mL), dried with anhydrous sodium sulfate, filtered, and concentrated under reduced pressure to obtain the crude product 2-(2-ethoxy-5-fluorophenyl)ethylene oxide 15c (1.30 g, light yellow oily product); yield: 92%.

$^1$H NMR (400 MHz, CDCl$_3$) δ 6.85-6.92 (m, 2H), 6.78-6.82 (m, 1H), 4.19-4.22 (m, 1H), 4.02-4.10 (m, 2H), 3.15-3.17 (m, 1H), 2.66-2.68 (m, 1H), 1.44 (t, J=8.0 Hz, 3H).

The Third Step

2-(2-Ethoxy-5-fluorophenyl)-2-((tetrahydro-2H-pyran-4-yl)oxy)ethanol 2-(2-Ethoxy-5-fluorophenyl)ethylene oxide 15c (1.30 g, 7.14 mmol) was added in tetrahydro-2H-pyran-4-ol 1c (2.19 g, 21.4 mmol) and aluminum trifluoromethanesulfonate (339 mg, 0.71 mmol) with stirring, and the mixture was reacted at room temperature for 3 h. 50 mL water was added in the reaction mixture, which was then extracted with ethyl acetate (50 mL×2). The organic phases were combined, washed with saturated sodium chloride solution (50 mL), dried with anhydrous sodium sulfate, filtered, and concentrated under reduced pressure. The residue was purified by silica gel column chromatography (eluent: A system) to obtain crude product 2-(2-ethoxy-5-fluorophenyl)-2-((tetrahydro-2H-pyran-4-yl)oxy)ethanol 15d (700 mg, colorless oily product); yield: 35%.

$^1$H NMR (400 MHz, CDCl$_3$) δ 7.12-7.16 (m, 1H), 6.90-7.00 (m, 1H), 6.70-6.80 (m, 1H), 5.00-5.05 (m, 1H), 3.90-4.05 (m, 5H), 3.65-6.75 (m, 1H), 3.35-3.55 (m, 4H), 2.27-2.30 (m, 1H), 1.95-2.05 (m, 1H), 1.70-1.80 (m, 1H), 1.60-1.70 (m, 1H), 1.41 (t, J=8.0 Hz, 3H).

The Fourth Step

Tert-butyl 2-(6-cyano-1-(2-(2-ethoxy-5-fluorophenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate Under nitrogen protection, tert-butyl 2-(6-cyano-5-methyl-2,4-dioxo-1,2-dihydrothieno[2,3-d]pyrimidin-3(4H)-yl)-2-methylpropionate 11 (333 mg, 0.95 mmol), 2-(2-ethoxy-5-fluorophenyl)-2-((tetrahydro-2H-pyran-4-yl)oxy)ethanol 15d (300 mg, 1.06 mmol), triphenylphosphine (417 mg, 1.59 mmol) and diisopropyl azodicarboxylate (322 mg, 1.59 mmol) were dissolved in 15 mL tetrahydrofuran, and the mixture was heated to 50° C. to react for 8 h. 50 mL water was added in the reaction mixture, which was then extracted with ethyl acetate (50 mL×2). The organic phases were combined, washed with saturated sodium chloride solution (50 mL), dried with anhydrous sodium sulfate, filtered, and concentrated under reduced pressure. The residue was purified by silica gel column chromatography (eluent: A system) to obtain tert-butyl 2-(6-cyano-1-(2-(2-ethoxy-5-fluorophenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate 15e (400 mg, white solid); yield: 62%.

MS m/z(ESI): 615.9 [M+1]

The Fifth Step

2-(6-Cyano-1-(2-(2-ethoxy-5-fluorophenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid Tert-butyl 2-(6-cyano-1-(2-(2-ethoxy-5-fluorophenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate 15e (400 mg, 0.65 mmol) was dissolved in 5 mL dichloromethane, and 1 mL trifluoroacetic acid was added. The mixture was reacted at 30° C. for 2 h. 50 mL water was added in the reaction mixture, which was then extracted with ethyl acetate (50 mL×2). The organic phases were combined, washed with saturated sodium chloride solution (50 mL), dried with anhydrous sodium sulfate, filtered, and concentrated under reduced pressure. The residue was purified by silica gel column chromatography (eluent: A system) to obtain 2-(6-cyano-1-(2-(2-ethoxy-5-fluorophenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid 15 (20 mg, white solid); yield: 6%.

MS m/z(ESI): 582.8 [M+23]

$^1$H NMR (400 MHz, CDCl$_3$) δ 7.21-7.24 (m, 1H), 6.96-7.01 (m, 1H), 6.80-6.85 (m, 1H), 5.28-5.30 (m, 1H), 4.20-4.30 (m, 2H), 4.01-4.09 (m, 2H), 3.65-3.80 (m, 2H), 3.31-3.45 (m, 3H), 2.66 (s, 3H), 1.70-1.82 (m, 7H), 1.55-1.60 (m, 1H), 1.45 (t, J=8.0 Hz, 3H), 1.25-1.40 (m, 2H).

EXAMPLE 16

(R)-2-(6-cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-N-methoxy-2-methylpropanamide

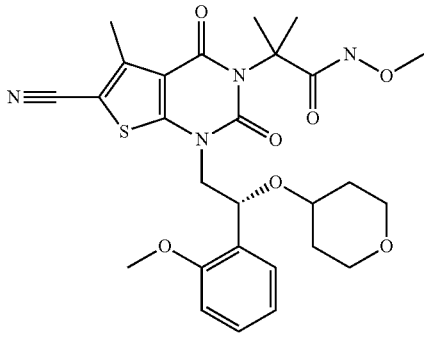

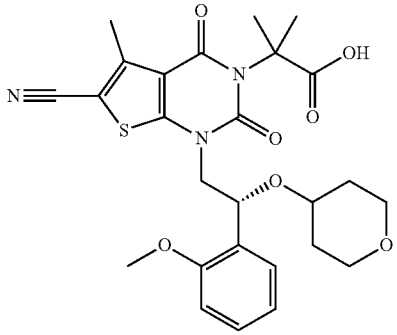

3 the first step →

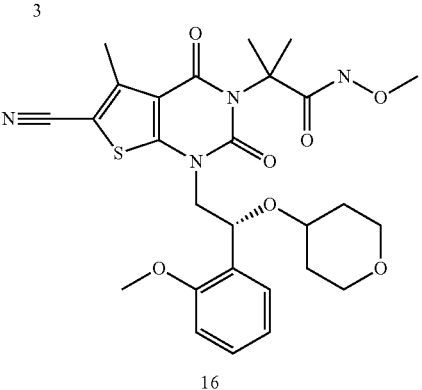

16

The First Step

(R)-2-(6-cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-N-methoxy-2-methylpropanamide Under nitrogen protection, (R)-2-(6-cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-N-methoxy-2-methylpropionic acid 3 (20 mg, 0.038 mmol) was dissolved in 1.5 mL tetrahydrofuran, and O-methylhydroxylamine hydrochloride (19 mg, 0.23 mmol) and N,N-diisopropylethylamine (49.1 mg, 0.38 mmol) were added. The mixture was stirred for 3 min, and bis(2-oxo-3- oxazolidinyl)phosphinyl chloride (19.3 mg, 0.076 mmol) was added. The mixture was reacted at 30° C. for 1 h. Bis(2-oxo-3-oxazolidinyl)phosphinyl chloride (38.6 mg, 0.15 mmol) and N,N-diisopropylethylamine (49.1 mg, 0.38 mmol) were supplemented, and the mixture was reacted at room temperature for 3 h. 10 mL water as added, and the mixture was extracted with ethyl acetate (6 mL×3). The organic phases were combined, successively washed with water (5 mL×2) and saturated sodium chloride solution (5 mL), and concentrated under reduced pressure. The obtained residue was purified by silica gel thin layer chromatography (developing solvent: B system) to obtain (R)-2-(6-cyano-1-(2-(2-methoxyphenyl)-2-((tetrahydro-2H-pyran-4-yl)oxy)ethyl)-5-methyl-2,4-dioxo-1,2-dihydrothiopheno[2,3-d]pyrimidin-3(4H)-yl)-N-methoxy-2-methylpropanamide 16 (5.0 mg, white solid); yield: 24%.

MS m/z(ESI): 578.8[M+23]

$^1$H NMR (400 MHz, CDCl$_3$) δ 8.20 (s, 1H), 7.50 (d, J=7.7 Hz, 1H), 7.38-7.26 (m, 1H), 7.02 (t, J=7.4 Hz, 1H), 6.84 (d, J=8.1 Hz, 1H), 5.41-5.26 (m, 1H), 4.07 (s, 1H), 3.99 (s, 1H), 3.81 (s, 6H), 3.75 (d, J=11.4 Hz, 2H), 3.45 (d, J=11.0 Hz, 1H), 3.35 (s, 2H), 2.61 (s, 3H), 1.80 (d, J=19.6 Hz, 6H), 1.72 (s, 1H), 1.54 (s, 1H), 1.42 (s, 2H).

EXAMPLE 17

2-(6-Cyano-1-(2-(2-(cyanomethoxy)-5-fluorophenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid

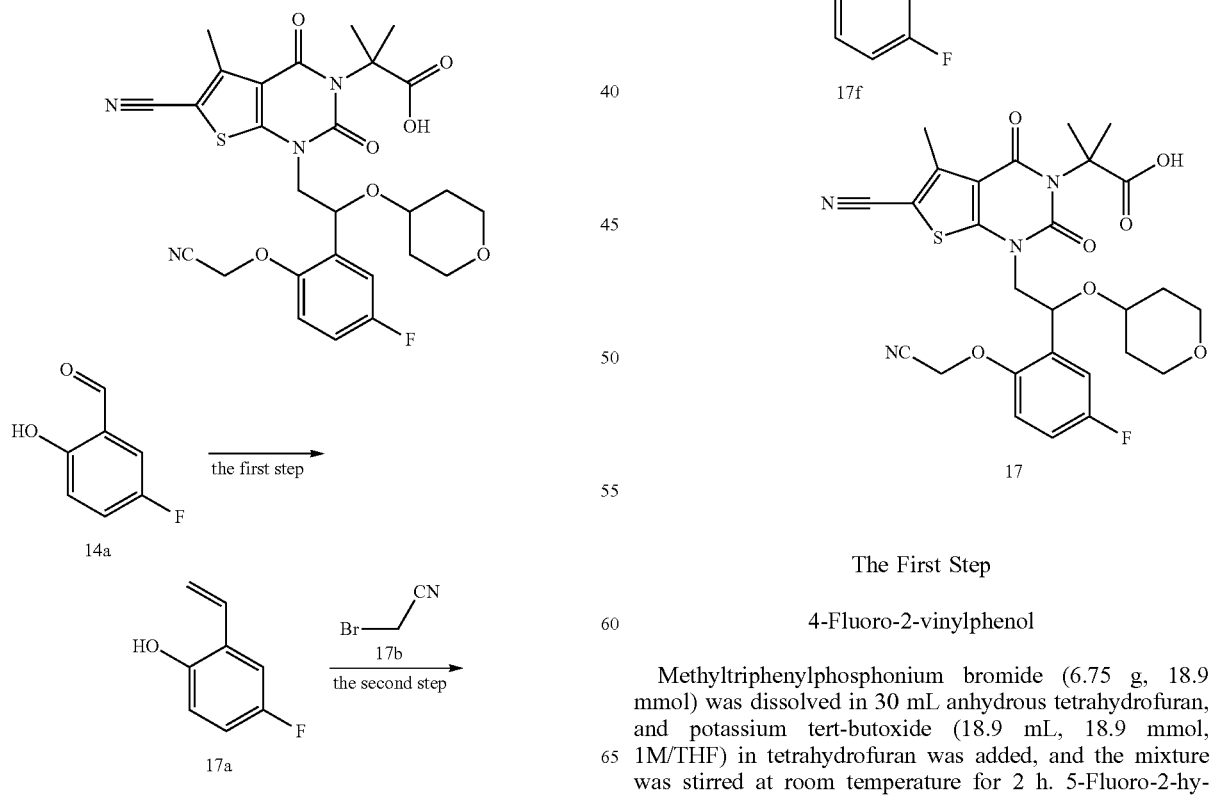

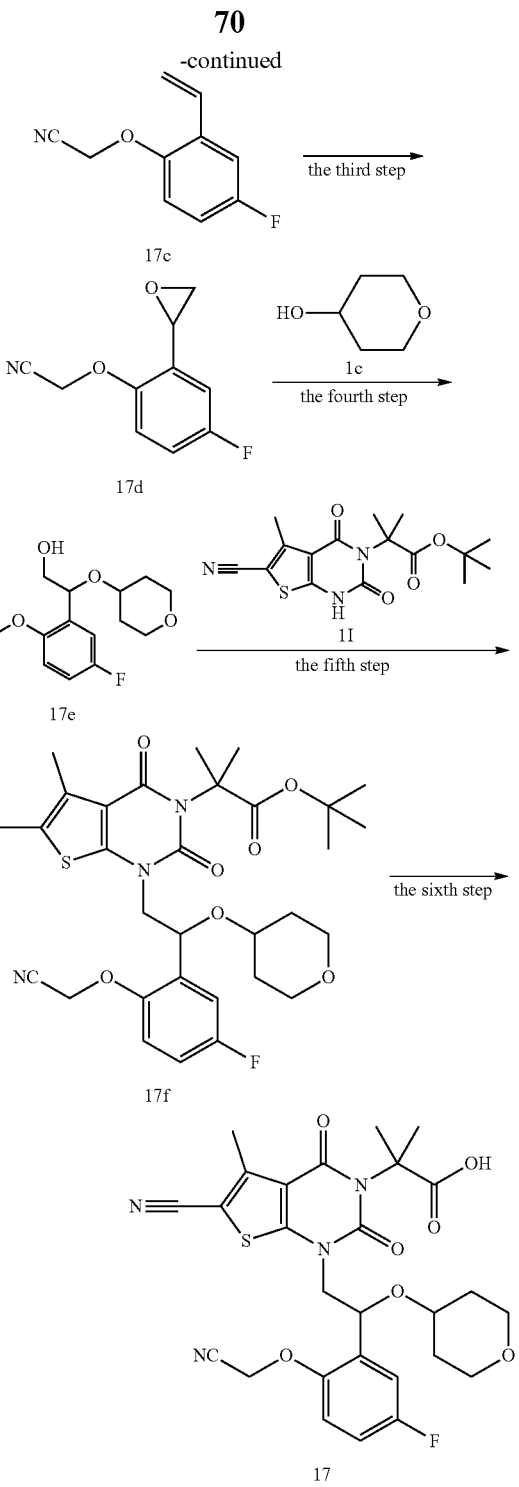

The First Step

4-Fluoro-2-vinylphenol

Methyltriphenylphosphonium bromide (6.75 g, 18.9 mmol) was dissolved in 30 mL anhydrous tetrahydrofuran, and potassium tert-butoxide (18.9 mL, 18.9 mmol, 1M/THF) in tetrahydrofuran was added, and the mixture was stirred at room temperature for 2 h. 5-Fluoro-2-hydroxybenzaldehyde 14a (1.15 g, 8.2 mmol) was dissolved in 5 mL tetrahydrofuran for use. The reaction mixture was cooled to −78° C., and the above tetrahydrofuran solution was added. After the temperature spontaneously rose to room temperature, the mixture continued to react for 4 h. 100 mL water was added in the reaction mixture, which was then extracted with ethyl acetate (80 mL×3). The organic phases were combined, and successively washed with water (80 mL×2) and saturated sodium chloride solution (80 mL×2). The organic phase was dried with anhydrous sodium sulfate, filtered, and concentrated under reduced pressure. The obtained residue was purified by silica gel thin layer chromatography (developing solvent: A system) to obtain 4-fluoro-2-vinylphenol 17a (0.96 g, wax-like yellow solid); yield: 84%.

$^1$H NMR (400 MHz, CDCl$_3$) δ 7.10 (dd, J=9.6, 3.2 Hz, 1H), 6.94-6.81 (m, 2H), 6.73 (dd, J=8.8, 4.4 Hz, 1H), 5.73 (d, J=18.0 Hz, 1H), 5.39 (d, J=10.8 Hz, 1H), 5.07 (s, 1H).

The Second Step 2-(4-fluoro-2-vinylphenoxy)acetonitrile

4-Fluoro-2-vinylphenol 17a (0.4 g, 2.89 mmol) and potassium carbonate (0.8 g, 5.79 mmol) were dissolved in 2 mL N,N-dimethylformamide, and the mixture was stirred at room temperature for 5 min. 2-Bromoacetonitrile 17b (520.6 mg, 4.34 mmol) was added, and the mixture was reacted at room temperature for 1 h. 10 mL water was added in the reaction mixture, which was then extracted with ethyl acetate (5 mL×3). The organic phases were combined, and washed with saturated sodium chloride solution (5 mL). The organic phase was dried with anhydrous sodium sulfate, filtered, and concentrated under reduced pressure to obtain 2-(4-fluoro-2-vinylphenoxy) acetonitrile 17c (450 mg, white crystal); yield: 88%.

MS m/z(ESI): 177.9 [M+1]

The Third Step 2-(4-Fluoro-2-(oxiran-2-yl)phenoxy)acetonitrile 2-(4-Fluoro-2-vinylphenoxy)acetonitrile 17c (450 mg, 2.54 mmol) was dissolved in 2 mL dichloromethane, m-chloroperbenzoic acid (1.31 g, 7.62 mmol) was added, and the mixture was reacted at room temperature for 3 h. The mixture was washed with saturated sodium bicarbonate (10 mL), and extracted with dichloromethane (5 mL×3). The organic phase was dried with anhydrous sodium sulfate, filtered, and concentrated under reduced pressure to obtain 2-(4-fluoro-2-(oxiran-2-yl)phenoxy)acetonitrile 17d (300 mg, white crystal); yield: 62%.

MS m/z(ESI): 194.1 [M+1]

The Fourth Step 2-(4-Fluoro-2-(2-hydroxy-1-((tetrahydro-2H-pyran-4-yl)oxy)ethyl)phenoxy)acetonitrile Tetrahydro-2H-pyran-4-ol 1c (476 mg, 4.66 mmol) and aluminum trifluoromethanesulfonate (36 mg, 0.075 mmol) were stirred at room temperature for 20 min, 2-(4-fluoro-2-(oxiran-2-yl)phenoxy)acetonitrile 17d (300 mg, 1.55 mmol) was added, and the mixture continued to react at room temperature for 2 h. 10 mL water was added in the reaction mixture, which was then extracted with ethyl acetate (10 mL×3). The organic phases were combined, and washed with water (10 mL×2). The organic phase was dried with anhydrous sodium sulfate, filtered, and concentrated under reduced pressure. The obtained residue was purified by silica gel column chromatography (eluent: A system) to obtain 2-(4-fluoro-2-(2-hydroxy-1-((tetrahydro-2H-pyran-4-yl)oxy)ethyl)phenoxy)acetonitrile 17e (160 mg, dark yellow oily product); yield: 35%.

$^1$H NMR (400 MHz, CDCl$_3$) δ 7.22 (dd, J=8.4, 2.8 Hz, 1H), 7.04-6.99 (m, 1H), 6.92 (dd, J=9.2, 4.0 Hz, 1H), 4.98 (dd, J=8.0, 3.6 Hz, 1H), 4.81 (d, J=5.2 Hz, 2H), 3.99-3.89 (m, 2H), 3.69-3.63 (m, 1H), 3.55-3.48 (m, 2H), 3.43-3.35 (m, 2H), 2.23 (dd, J=9.2, 3.2 Hz, 1H), 2.03-1.99 (m, 1H), 1.81-1.77 (m, 1H), 1.68-1.63 (m, 2H).

The Fifth Step

Tert-butyl 2-(6-cyano-1-(2-(2-(cyanomethoxy)-5-fluorophenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate Under nitrogen protection, tert-butyl 2-(6-cyano-5-methyl-2,4-dioxo-1,2-dihydrothieno[2,3-d]pyrimidin-3 (4H)-yl)-2-methylpropionate 11 (180 mg, 0.54 mmol), 2-(4-fluoro-2-(2-hydroxy-1-((tetrahydro-2H-pyran-4-yl)oxy) ethyl)phenoxy)acetonitrile 17e (160 mg, 0.54 mmol) and triphenylphosphine (283 mg, 1.08 mmol) were dissolved in 3 mL anhydrous tetrahydrofuran. The mixture was cooled to 0° C., and diisopropyl azodicarboxylate (218 mg, 1.08 mmol) was added. After the completion of addition, the mixture was heated to room temperature to react for 18 h. 20 mL water was added in the reaction mixture, which was then extracted with ethyl acetate (10 mL×3). The organic phases were combined, washed with saturated saline solution (10 mL×2), dried with anhydrous sodium sulfate, filtered, concentrated under reduced pressure. The obtained residue was purified by silica gel column chromatography (eluent: A system) to obtain tert-butyl 2-(6-cyano-1-(2-(2-(cyanomethoxy)-5-fluorophenyl)-2-((tetrahydro-2H-pyran-4-yl) oxy)ethyl)-5-methyl-2,4-dioxo-1,2-dihydrothiopheno[2,3-d]pyrimidin-3 (4H)-yl)-2-methylpropionate 17f (300 mg, white solid); yield: 88.7%.

MS m/z(ESI): 570.8 [M-55]

The Sixth Step 2-(6-Cyano-1-(2-(2-(cyanomethoxy)-5-fluorophenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid Tert-butyl 2-(6-cyano-1-(2-(2-(cyanomethoxy)-5-fluorophenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate 17f (300 mg, 0.48 mmol) was dissolved in 3.5 mL dichloromethane. The mixture was cooled to 0° C., and 0.7 mL trifluoromethanesulfonic acid was added. After the completion of addition, the mixture was heated to room temperature and reacted for 3 h. 10 mL water was added to the reaction mixture, which was then extracted with dichloromethane (10 mL×3). The organic phases were combined, washed with water (10 mL×3), filtered, and concentrated under reduced pressure. The obtained residue was purified by silica gel thin layer chromatography (developing solvent: B system) to obtain 2-(6-cyano-1-(2-(2-(cyanomethoxy)-5-fluorophenyl)-2-((tetrahydro-2H-pyran-4-yl)oxy)ethyl)-5-methyl-2,4-dioxo-1,2- dihydrothiopheno[2,3-d]pyrimidin-3(4H)-yl)-2-methylpropionic acid 17 (40 mg, white solid); yield: 14.6%.

MS m/z(ESI): 552. 8 [M-H$_2$O+1]

$^1$H NMR (400 MHz, CDCl$_3$) δ 7.30 (dd, J=8.6, 3.0 Hz, 1H), 7.10-7.04 (m, 1H), 6.97 (dd, J=8.8, 4.4 Hz, 1H), 5.29 (dd, J=8.4, 3.6 Hz, 1H), 4.87 (d, J=8.4 Hz, 2H), 4.24-4.20 (m, 1H), 3.80-3.71 (m, 3H), 3.49-3.45 (m, 1H), 3.40-3.32 (m, 2H), 2.65 (s, 3H), 1.85 (s, 3H), 1.81 (s, 3H), 1.82-1.74 (m, 2H), 1.62-1.52 (m, 1H), 1.42-1.36 (m, 1H).

EXAMPLE 18

2-(6-Cyano-1-(2-(5-fluoro-2-(2-methoxyethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid

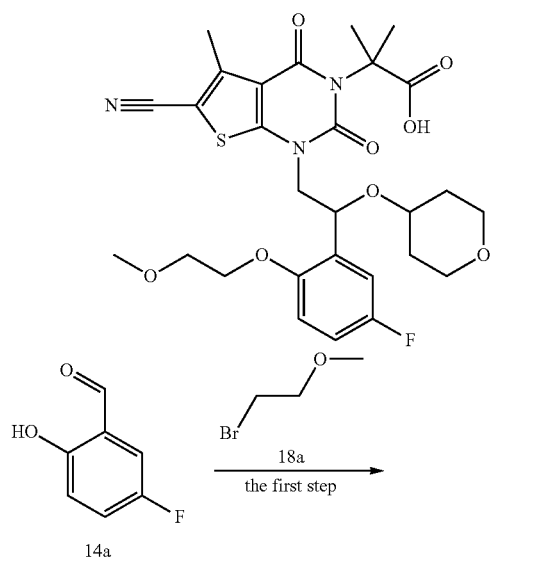

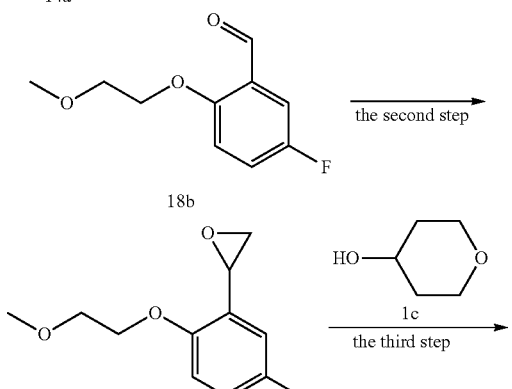

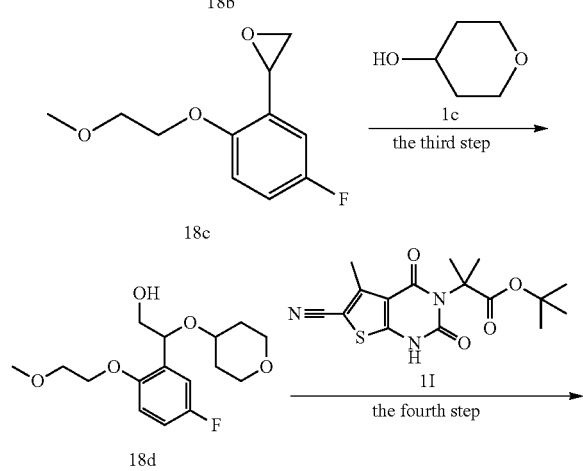

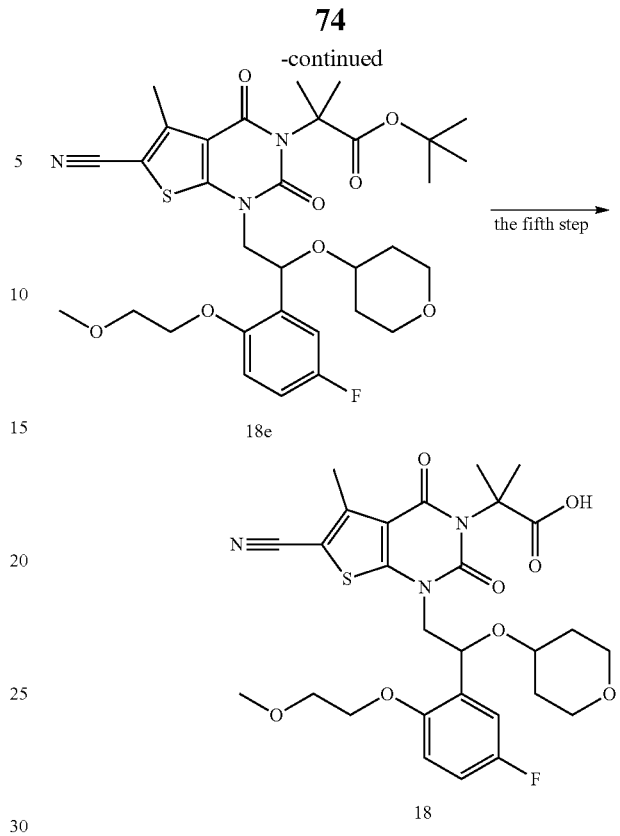

The First Step

5-Fluoro-2-(2-methoxyethoxy)benzaldehyde

5-Fluoro-2-hydroxybenzaldehyde 14a (1.40 g, 10 mmol), 1-bromo-2-methoxyethane 18a (2.08 g, 15 mmol) and potassium carbonate (3.45 g, 25 mmol) were dissolved in 20 mL N,N-dimethylformamide, and the mixture was reacted at 50° C. for 4 h. 50 mL water was added in the reaction mixture, which was then extracted with ethyl acetate (50 mL×2). The organic phases were combined, and washed with saturated sodium chloride solution (50 mL). The organic phase was dried with anhydrous sodium sulfate, filtered, and concentrated under reduced pressure. The obtained residue was purified by silica gel column chromatography (eluent: B system) to obtain 5-fluoro-2-(2-methoxyethoxy)benzaldehyde 18b (1.6 g, white solid); yield: 80%.

$^1$H NMR (400 MHz, CDCl$_3$) δ 10.47 (d, J=3.2 Hz, 1H), 7.51 (dd, J=8.4, 3.2 Hz, 1H), 7.25-7.22 (m, 1H), 6.98 (dd, J=9.2, 4.0 Hz, 1H), 4.23 (t, J=4.4 Hz, 2H), 3.80 (t, J=4.8 Hz, 2H), 3.46 (s, 3H).

The Second Step 2-(5-Fluoro-2-(2-methoxyethoxy)phenyl)ethylene oxide

5-Fluoro-2-(2-methoxyethoxy)benzaldehyde 18b (1.6 g, 8.07 mmol), trimethylsulfonium iodide (1.98 g, 9.69 mmol) and potassium hydroxide (1.36 g, 24.2 mmol) were dissolved in 30 mL dimethylsulfoxide, and the mixture was reacted at 80° C. for 1 h. 100 mL water was added in the reaction mixture, and the reaction mixture was extracted with ethyl acetate (100 mL×2). The organic phases were combined, and washed with saturated sodium chloride solution (100 mL×3). The organic phase was dried with anhydrous sodium sulfate, filtered, and concentrated under reduced pressure to obtain 2-(5-fluoro-2-(2-methoxyethoxy)phenyl)ethylene oxide 18c (1.6 g, light yellow oily product); yield: 94%.

$^1$H NMR (400 MHz, CDCl$_3$) δ 6.93-6.88 (m, 1H), 6.86-6.81 (m, 2H), 4.23-4.22 (m, 1H), 4.17-4.10 (m, 2H), 3.76 (t, J=4.8 Hz, 2H), 3.45 (s, 3H), 3.15 (dd, J=5.6, 4.0 Hz, 1H), 2.66 (dd, J=6.0, 2.4 Hz, 1H).

The Third Step 2-(5-Fluoro-2-(2-methoxyethoxy)phenyl)-2-((tetrahydro-2H-pyran-4-yl)oxy)ethanol Tetrahydro-2H-pyran-4-ol 1c (2.3 g, 22.6 mmol) and aluminum trifluoromethanesulfonate (358 mg, 0.754 mmol) were stirred at room temperature for 20 min, and 2-(5-fluoro-2-(2-methoxyethoxy)phenyl)ethylene oxide 18c (1.6 g, 7.54 mmol) was added. The mixture continued to react at room temperature for 3 h. 100 mL water was added in the reaction mixture, which was then extracted with ethyl acetate (100 mL×3). The organic phases were combined, and successively washed with water (10 mL) and saturated sodium chloride solution (100 mL). The organic phase was dried with anhydrous sodium sulfate, filtered, and concentrated under reduced pressure. The obtained residue was purified by silica gel column chromatography (developing solvent: A system) to obtain 2-(5-fluoro-2-(2-methoxyethoxy)phenyl)-2-((tetrahydro-2H-pyran-4-yl)oxy)ethanol 18d (900 mg, yellow oily product); yield: 38%.

MS m/z(ESI): 336.9 [M+23]

The Fourth Step

Tert-butyl 2-(6-cyano-1-(2-(5-fluoro-2-(2-methoxyethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate Under nitrogen protection, tert-butyl 2-(6-cyano-5-methyl-2,4-dioxo-1,2-dihydrothieno[2,3-d]pyrimidin-3(4H)-yl)-2-methylpropionate 11 (348 mg, 0.999 mmol), 2-(5-fluoro-2-(2-methoxyethoxy)phenyl)-2-((tetrahydro-2H-pyran-4-yl)oxy)ethanol 18d (350 mg, 1.11 mmol) and triphenylphosphine (437 mg, 1.67 mmol) were dissolved in 15 mL anhydrous tetrahydrofuran, and the mixture was cooled to 0° C., and diisopropyl azodicarboxylate (337 mg, 1.67 mmol) was added. After the completion of addition, the mixture was reacted at 60° C. for 8 h. 50 mL water was added in the reaction mixture, which was then extracted with ethyl acetate (50 mL×2). The organic phases were combined, washed with saturated sodium chloride solution (50 mL×2), dried with anhydrous sodium sulfate, filtered, and concentrated under reduced pressure. The obtained residue was purified by silica gel column chromatography (eluent: A system) to obtain tert-butyl 2-(6-cyano-1-(2-(5-fluoro-2-(2-methoxyethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate 18e (200 mg, light yellow oily product); yield: 31.1%.

MS m/z(ESI): 645.9 [M+1]

The Fifth Step 2-(6-Cyano-1-(2-(5-fluoro-2-(2-methoxyethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid Tert-butyl 2-(6-cyano-1-(2-(5-fluoro-2-(2-methoxyethoxy)phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionate 18e (200 mg, 0.31 mmol) was dissolved in 5 mL dichloromethane, and the mixture was cooled to 0° C., and 1 mL trifluoromethanesulfonic acid was added. After the completion of addition, the mixture was heated to room temperature to react for 3 h. 20 mL water was added to the reaction mixture, which was then extracted with dichloromethane (20 mL×3). The organic phases were combined, washed with saturated sodium chloride solution (20 mL×2), dried with anhydrous sodium sulfate, filtered, and concentrated under reduced pressure. The obtained residue was purified by silica gel thin layer chromatography (developing solvent: B system) to obtain 2-(6-cyano-1-(2-(5-fluoro-2-(2-methoxyethoxy)phenyl)-2-((tetrahydro-2H-pyran-4-yl)oxy))ethyl)-5-methyl-2,4-dioxo-1,2-dihydrothiopheno[2,3-d]pyrimidin-3(4H)-yl)-2-methylpropionic acid 18 (10 mg, white solid); yield: 5.5%.

MS m/z(ESI): 589.9 [M+1]

$^1$H NMR (400 MHz, CDCl$_3$) δ 7.25-7.23 (m, 1H), 6.70-6.95 (m, 1H), 6.78 (dd, J=8.4, 4.0 Hz, 1H), 5.32 (d, J=8.4 Hz, 1H), 4.56 (t, J=11.2 Hz, 1H), 4.27-4.19 (m, 2H), 4.05-3.97 (m, 3H), 3.93-3.86 (m, 2H), 3.51-3.49 (m, 1H), 3.47 (s, 3H), 3.43-3.36 (m, 2H), 2.67 (s, 3H), 2.07-2.06 (m, 1H), 2.05 (s, 3H), 1.85 (s, 3H), 1.81-1.80 (m, 1H), 1.70-1.63 (m, 2H).

EXAMPLE 19

(R)-2-(6-cyano-1-(2-(2-ethoxy-5-fluoro-phenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid

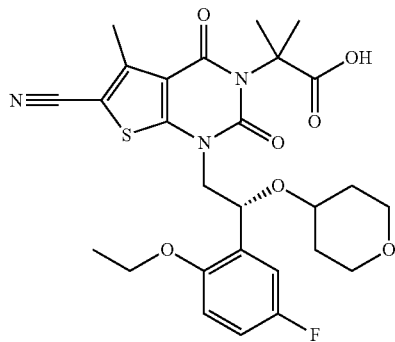

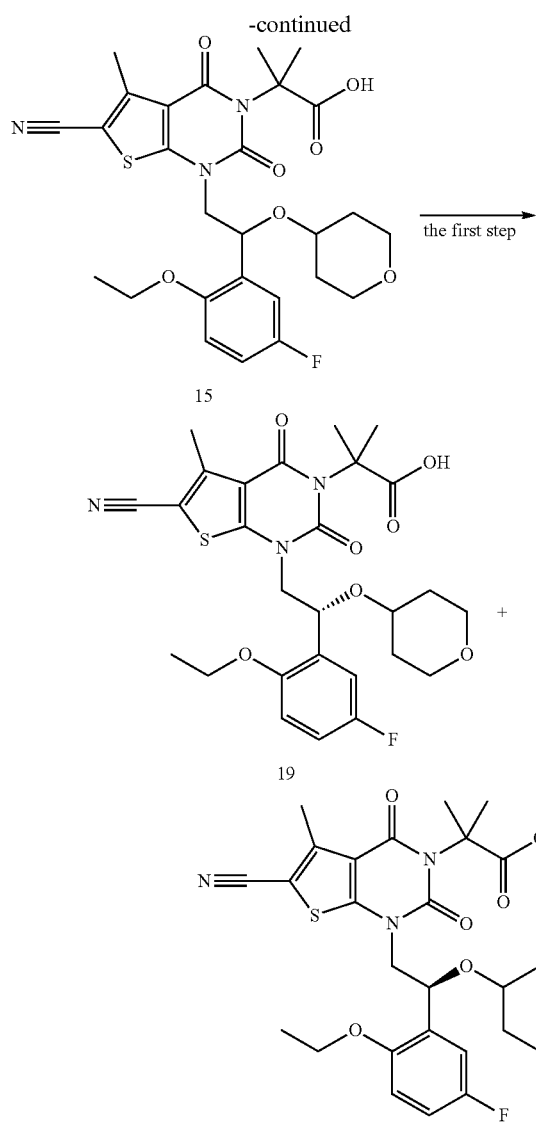

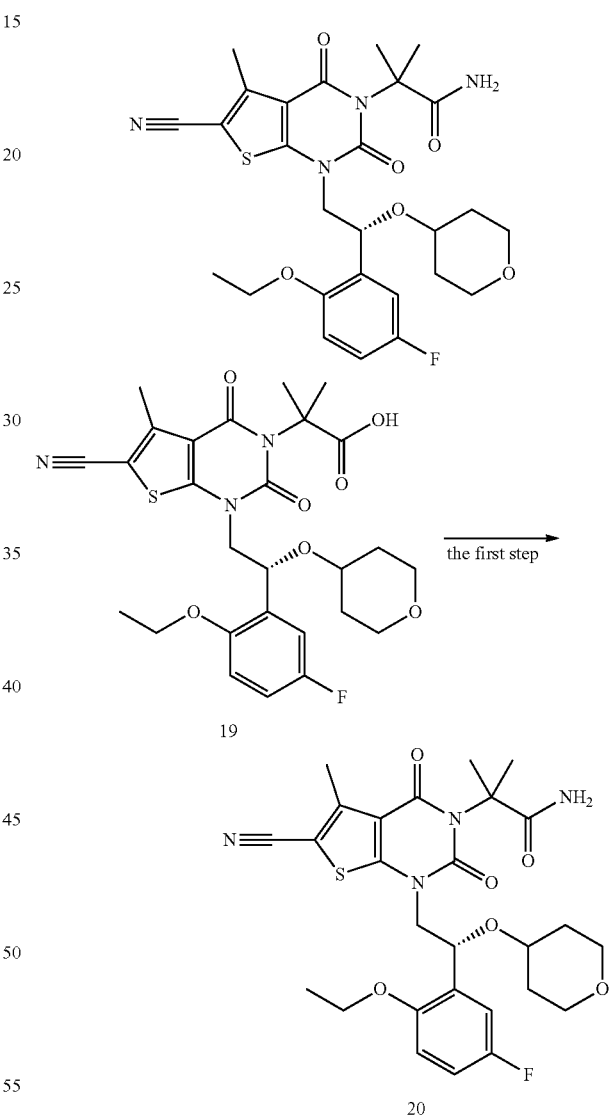

The First Step (R)-2-(6-cyano-1-(2-(2-ethoxy-5-fluorophenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid 2-(6-Cyano-1-(2-(2-ethoxy-5-fluorophenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropionic acid 15 (120 mg, 0.21 mmol) was further separated by supercritical fluid chromatography (SFC) using preparative high-performance liquid chromatography and chiral column to separate chiral isomers (chiral column ChiralPak AD, 250×30mm I.D., 10 μm, 60 mL/min; mobile phase A for $CO_2$ and B for EtOH (0.1% $NH_3.H_2O$)) to obtain (R)-2-(6-cyano-1-(2-(2-ethoxy-5-fluorophenyl)-2-((tetrahydro-2H-pyran-4-yl)oxy)ethyl)-5-methyl-2,4-dihydrothiopheno[2,3-d]pyrimidin-3 (4H)-yl)-2-methylproponic acid 19 (69.47 mg, white solid); yield: 57.9%; 100.0% ee, retention time: 4.55min.

MS m/z(ESI): 582.8[M+23]

$^1$H NMR (400 MHz, CDCl$_3$) δ 7.24-7.21 (m, 1H), 7.01-6.96 (m, 1H), 6.85-6.80 (m, 1H), 5.28-5.26 (m, 1H), 4.30-4.20 (m, 1H), 4.09-4.01 (m, 2H), 3.80-3.65 (m, 2H), 3.45-3.40 (m, 2H), 3.38-3.30 (m, 2H), 2.65 (s, 3H), 1.71 (s, 3H), 1.70 (s, 3H), 1.82-1.70 (m, 2H), 1.60-1.55 (m, 2H), 1.45 (t, J=8.0 Hz, 3H).

EXAMPLE 20

(R)-2-(6-cyano-1-(2-(2-ethoxy-5-fluorophenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropanamide

The First Step (R)-2-(6-cyano-1-(2-(2-ethoxy-5-fluorophenyl)-2-((tetrahydro-2H-pyran-4-yl)oxy)ethyl)-5-methyl-2,4-dioxo-1,2-dihydrothiopheno[2,3-d]pyrimidin-3(4H)-yl)-2-methylpropanamide (R)-2-(6-Cyano-1-(2-(2-ethoxy-5-fluorophenyl)-2-((tetrahydro-2H-pyran-4-yl)oxy)ethyl1-5-methyl-2,4-dioxo-1,2- dihydrothipheno[2,3-d]pyrimidin-3(4H)-yl)-2-methylpropionic acid (20 mg, 0.0357 mmol), ammonium chloride (4.8 mg, 0.0893 mmol), N,N'-dicyclohexylcarbimide (11 mg, 0.0536 mmol) and 4-dimethylaminopyridine (6.6 mg, 0.0536 mmol) were dissolved in 5 mL dichloromethane, and the mixture was reacted at 40° C. for 8 h. 50 mL water was added in the reaction mixture, which was then extracted with ethyl acetate (50 mL×2). The organic phases were combined, and washed with saturated sodium chloride solution (50 mL). The organic phase was dried with anhydrous sodium sulfate, filtered, and concentrated under reduced pressure. The obtained residue was purified by silica gel thin layer chromatography (developing solvent: B system) to obtain (R)-2-(6-cyano-1-(2-(2-ethoxy-5-fluorophenyl)-2-((tetrahydro-2H-pyran-4-yl)oxy)ethyl)-5-methyl-2,4-dioxo-1,2-dihydrothipheno[2,3-d]pyrimidin-3(4H)-yl)-2-methylpropanamide 20 (8.0 mg, white solid); yield: 40%.

MS m/z(ESI): 541.8 [M-H₂O+1]

¹H NMR (400 MHz, CDCl₃) δ 7.24-7.21 (m, 1H), 7.01-6.96 (m, 1H), 6.85-6.80 (m, 1H), 5.42 (s, 2H), 5.28-5.26 (m, 1H), 4.30-4.20 (m, 1H), 4.09-4.01 (m, 2H), 3.80-3.65 (m, 2H), 3.45-3.40 (m, 2H), 3.38-3.30 (m, 2H), 2.65 (s, 3H), 1.71 (s, 3H), 1.70 (s, 3H), 1.82-1.70 (m, 2H), 1.60-1.55 (m, 2H), 1.45 (t, J=8.0 Hz, 3H).

EXAMPLE 21

(R)-2-(6-Cyano-1-(2-(5-fluoro-2-(2-fluoroethoxy)phenyl)-2-((tetrahydro-2H-pyran-4-yl)oxy)ethyl)-5-methyl-2,4-dioxo-1,2-dihydrothipheno[2,3-d]pyrimidin-3(4H)-yl)-2-methylpropionic acid

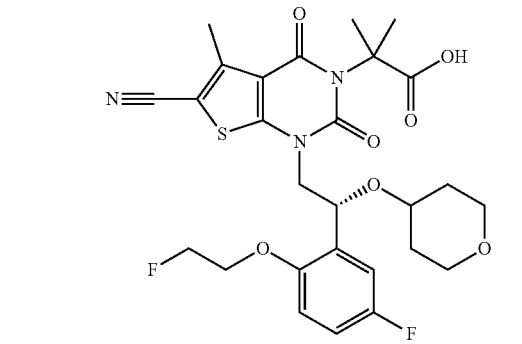

14 the first step

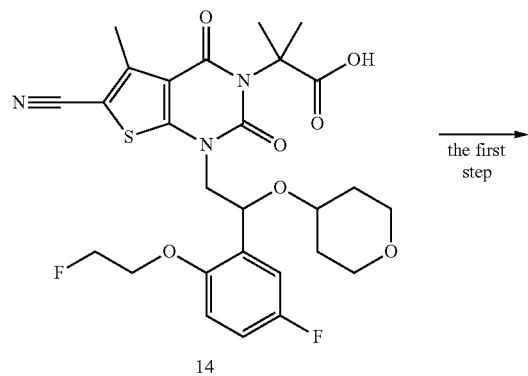

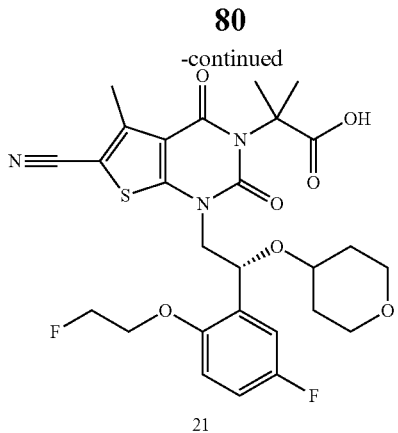

21

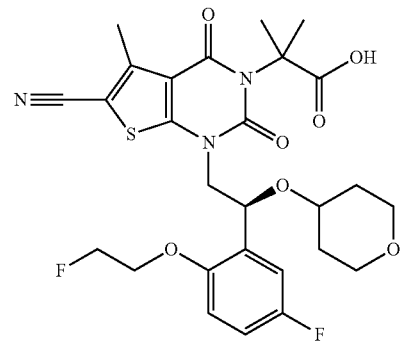

The First Step (R)-2-(6-cyano-1-(2-(5-fluoro-2-(2-fluoroethoxy)phenyl)-2-((tetrahydro-2H-pyran-4-yl)oxy)ethyl)-5-methyl-2,4-dioxo-1,2-dihydrothipheno[2,3-d]pyrimidin-3(4H)-yl)-2-methylpropionic acid 2-(6-Cyano-1-(2-(5-fluoro-2-(2-fluoroethoxy)phenyl)-2-((tetrahydro-2H-pyran-4-yl)oxy)ethyl)-5-methyl-2,4-dioxo-1,2-dihydrothipheno[2,3-d]pyrimidin-3(4H)-yl)-2-methylpropionic acid 14 (435 mg, 0.75 mmol) was further separated by supercritical fluid chromatography (SFC) using preparative high-performance liquid chromatography and chiral column to separate chiral isomers (chiral column ChiralPak AD, 250×30 mm I.D., 10 μm, 60 mL/min; mobile phase A for CO₂ and B for EtOH (0.1% NH₃.H₂O)) to obtain (R)-2-(6-cyano-1-(2-(5-fluoro-2-(2-fluoroethoxy)phenyl)-2-((tetrahydro-2H-pyran-4-yl)oxy)ethyl)-5-methyl-2,4-dioxo-1,2-dihydrothipheno[2,3-d]pyrimidin-3 (4H)-yl)-2-methylpropionic acid 21 (109.31 mg, white solid); yield: 25.1%; 100.0% ee, retention time: 4.71 min.

MS m/z(ESI): 599.8 [M+23]

¹H NMR (400 MHz, CDCl₃) δ 7.23 (dd, J=8.8, 3.6 Hz, 1H), 7.00 (td, J=8.8, 3.2 Hz, 1H), 6.83 (dd, J=8.8, 4.0 Hz, 1H), 5.32 (dd, J=9.2, 3.6 Hz, 1H), 4.96-4.72 (m, 2H), 4.34-4.27 (m, 2H), 4.24-4.20 (m, 1H), 3.77-3.72 (m, 2H), 3.69-3.65 (m, 1H), 3.45-3.28 (m, 3H), 2.65 (s, 3H), 1.82 (s, 3H), 1.78 (s, 3H), 1.75-1.73 (m, 2H), 1.59-1.50 (m, 1H), 1.38-1.30 (m, 1H).

BIOLOGICAL EVALUATION

TEST EXAMPLE 1

Determination of $IC_{50}$ of Inhibition of Enzymatic Activity of ACC1 and ACC2 by the Compound of the Present Disclosure The degree of inhibition of the enzymatic activity of recombinant human ACC1, ACC2 proteins under in-vitro conditions by the preferred compounds of the present disclosure is determined by the following method.

The principle of the method was based on the reaction of ACC protein-catalyzed acetyl-CoA to form malonyl-CoA. ATP was consumed during this reaction and ADP was produced. The produced ADP was reconverted into ATP by using ADP-Glo™ Kinase Kit from Promega. This part of ATP reacted with the luciferase-fluorescence in the kit, and generated chemiluminescent signals. Thus, by measuring the intensity of chemiluminescent signal, the amount of ADP produced in the catalytic reaction was reflected, thereby indirectly determining the enzymatic activity of ACC protein and the effect of the tested compound on the enzymatic activity. The main reagents used included ACC1, ACC2 proteins (purchased from BPS bioscience, ACC1 Art. No. 50200, ACC2 Art. No. 50201), acetyl-CoA (acetyl-CoA, purchased from Sigma, Art. No. A2056), $NaHCO_3$ (purchased from Sigma, Art. No. S6014), ADP-Glo™ Kinase assay kit (purchased from Promega, Art. No. V9102).

The test procedure was briefly described as follows: firstly, a 1× buffer solution required for the reaction was prepared, comprising: 50 mM HEPES (pH7.4 purchased from Invitrogen, Art. No. 15630), 2 mM magnesium chloride ($MgCl_2$, purchased from Sigma, Art. No. M1028), 2 mM potassium citrate (Potassium citrate, purchased from Sigma, Art. No. 89306), 0.01% Brij-35 detergent (purchased from Merck, Art. No. 203728), 2 mM DTT (purchased from Sigma, Art. No. D0632). The test compound powder was dissolved in DMSO to prepare a stock solution having a concentration of 10 mM, followed by three-fold dilution to prepare the concentration required for the test, and each compound was set at 10 concentration points ranging from 10 μm to 0.5 nM. Firstly, appropriate amount of ACC protein (2 nM) was added to a 384-well microplate, and then diluted test compound solutions were added to each well. A duplicate well was provided at each concentration, and a solution control group (blank group) and a negative control group (DMSO group) were set at the same time. The 384-well plates were then shaken on a microwell plate oscillator and incubated for 15 minutes at room temperature. Thereafter, a substrate mixture containing ATP, acetyl-CoA and $NaHCO_3$ which was diluted with the aforementioned buffer solution was added to each well to start the reaction, and the final concentrations of the three components were respectively ATP 20 μM, acetyl-CoA 10 μM, and $NaHCO_3$ 30 mM. After reacting for 30 minutes at room temperature, the corresponding reaction solution and detection solution were added to each well according to the method in the specification of ADP-Glo™ Kinase assay kit (referring to the specification of the kit for specific methods). Finally, the relative light unit (RLU) values of each well were tested using an Envision 2104 multi-function microplate reader (Perkin Elmer). The percentage inhibition rate of a compound at a concentration on ACC enzyme activity was calculated by the following formula:

Inhibition rate %=[(RLU average value of negative control wells−RLU average value of blank control wells)−(RLU average values of test wells−RLU average values of blank control wells)]/(RLU average values of negative control wells−RLU average values of blank control wells)*100

Finally, nonlinear regression analysis of the logarithm of the concentration of the compound and the percentage inhibition rate of the corresponding concentration was carried out in the GraphPad Prism5 software to obtain the half maximal inhibitory concentration ($IC_{50}$) of the compound.

TABLE 1

$IC_{50}$ data for inhibition of ACC1 and ACC2 enzyme activities by the compounds of the present disclosure

| Example No. | $IC_{50}$(nM)/ACC1 | $IC_{50}$(nM)/ACC2 |
|---|---|---|
| 1 | 38 | ND |
| 2 | 16 | ND |
| 3 | 11.6 | ND |
| 4 | 16.5 | ND |
| 6 | 21 | ND |
| 11 | 15 | ND |
| 13 | 36 | ND |
| 14 | 7.9 | ND |
| 15 | 4.4 | ND |
| 17 | 20.7 | ND |
| 19 | 2.7 | 6 |
| 20 | 13.1 | ND |
| 21 | 6.4 | 22 |

Comment: ND means the sample was not tested.

Conclusion: The compounds of the present disclosure have a good inhibition effects on both ACC1 enzyme and ACC2 enzyme.

TEST EXAMPLE 2

Oral Pharmacokinetic Researches of the Compounds of the Present Disclosure in SD Rats 1. Summary SD rat was used as the experimental animal. The drug concentrations in plasma and liver at different times were tested after the rats were intragastrically administered with the compound of Example 19 by LC/MS/MS methods, so as to research the pharmacokinetic characteristics of compound of present disclosure in rats.

2. Experimental Scheme 2.1 Experimental Drugs and Animals

The compound of Example 19;

6 healthy male adult SD rats; purchased from Shanghai Xipuer-Bikai Experimental Animal Co., Ltd.; the body weight of the animals: 180-220 g.

2.2 Drug Preparation and Drug Delivery

An appropriate amount of experimental drug was weighed, and 0.5% sodium carboxymethylcellulose (CMC-Na) was added, and the mixture was milled to prepare a 1 mg/mL suspension;

6 healthy adult male rats were divided into 2 groups, fasted overnight and respectively intragastrically administered with the drug at a dosage of 10 mg/kg, at a volume of 10 mL/kg. The rats were feed 2 h after the administration.

2.3 Sample Collection

Blood was collected by jugular vein puncture, and about 0.25 mL was collected for each sample, which was anticoagulated by using heparin sodium, and the samples were placed on ice after collection. The time points of blood collection were as follows:

The first group of animals: blood collection time: before administration, and 0.083 h, 0.25 h, 0.5 h, 1 h, 2 h, 4 h, 6 h, 8 h and 24 h after administration.

The second group of animals: the animals were euthanized 0.5 h after administration, and the liver tissues were collected, 3 rats/time point.

Blood samples were collected and placed on ice, and plasma was separated by centrifugation (centrifugation conditions: 8000 rpm, 6 min, 2-8° C.). The collected plasma was stored at −80° C. before analysis.

The content of the test compound in the plasma and liver of the rats after intragastrically administration was analyzed by LC-MS/MS.

3. Results of the Pharmacokinetic Parameters

The pharmacokinetic parameters of the compound in Example 19 of the present disclosure were shown below:

| | Pharmacokinetic experiments (10 mg/kg) | | | |
|---|---|---|---|---|
| Example No. | Blood concentration Cmax (ng/mL) | Curve area $AUC_{0-\infty}$ (ng · h/mL) | Half-life period $T\frac{1}{2}(h)$ | Residence time MRT(h) |
| 19 | 920 ± 362 | 1941 ± 1189 | 3.39 ± 0.65 | 2.82 ± 0.34 |

Conclusion: The compound of Example 19 was well absorbed in pharmacokinetics, and had good pharmacokinetic properties; at the same time, after 0.5 h of administration, the drug concentration in the liver was 46830±14015 ng/mL, indicating that the compound of Example 19 was well enriched in the liver.

All documents mentioned in the present application are incorporated herein by reference, as if each document is cited separately as a reference. In addition, it should be understood that those skilled in the art, after reading the details of the present disclosure, can make various modifications and changes on the present disclosure, and these equivalent forms are also within the scope defined by the claims in the present disclosure.

The invention claimed is:

1. A compound as shown in Formula (I):

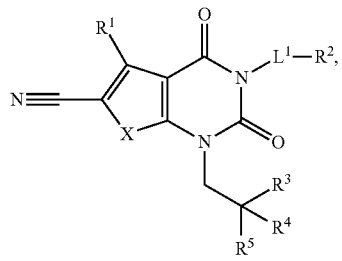

(I)

or stereoisomers, tautomers, or pharmaceutically acceptable salts thereof,
wherein
X is selected from —NH—, —O— or —S—;
$L^1$ is selected from alkylene, cycloalkylene or heterocyclylene;
$R^1$ is selected from hydrogen atom, alkyl, halogen, alkoxy or cyano, wherein the alkyl or alkoxy is optionally further substituted by one or more substituent groups selected from halogen, hydroxy, cyano, nitro, alkoxy, cycloalkyl, heterocyclyl, aryl, heteroaryl, —$NR^8R^9$, —C(O)$NR^8R^9$, —C(O)$R^6$, —OC(O)$R^6$, —S(O)$_q NR^8R^9$, —$NR^8S(O)_2R^9$ or —$NR^8C(O)R^9$;

$R^2$ is selected from hydrogen atom, hydroxy, halogen, nitro, cyano, alkyl, alkoxy, cycloalkyl, heterocyclyl, aryl, heteroaryl, —$NR^8R^9$, —C(O)$NR^8R^9$, —C(O)$R^6$, —OC(O)$R^6$, —S(O)$_q NR^8R^9$, —$NR^8S(O)_2R^9$ or —$NR^8C(O)R^9$, wherein the alkyl, alkoxy, cycloalkyl, heterocyclyl, aryl or heteroaryl is optionally further substituted by one or more substituent groups selected from hydroxy, halogen, nitro, cyano, alkyl, alkoxy, cycloalkyl, heterocyclyl, aryl, heteroaryl, —$NR^{10}R^{11}$, —C(O)$NR^{10}R^{11}$, —C(O)$R^{12}$, —C(O)O$R^{12}$ or —$NR^{10}C(O)R^{11}$;

$R^3$ is selected from aryl or heteroaryl, wherein the aryl or heteroaryl is optionally further substituted by one or more substituent groups selected from $R^7$;

$R^4$ and $R^5$ are each independently selected from hydrogen atom, alkyl, —$OR^6$, —$SR^6$, —$NR^8R^9$, —C(O)$NR^8R^9$, —C(O)$R^6$, —OC(O)$R^6$, —S(O)$_q NR^8R^9$, —$NR^8S(O)_2R^9$ or —$NR^8C(O)R^9$;

or, $R^4$ and $R^5$, together with the atom to which they are attached, form a $C_{3-8}$ saturated or partly unsaturated cycloalkyl, or form a $C_{4-8}$ saturated or partly unsaturated heterocyclyl having one or more heteroatoms selected from N, O and S(O)q, wherein the cycloalkyl or heterocyclyl is optionally further substituted by one or more substituent groups selected from hydroxy, halogen, nitro, cyano, alkyl, alkoxy, cycloalkyl, heterocyclyl, aryl, heteroaryl, —$NR^8R^9$, —C(O)$NR^8R^9$, —C(O)$R^6$, —OC(O)$R^6$, —S(O)$_q NR^8R^9$, —$NR^8S(O)_2R^9$ or —$NR^8C(O)R^9$;

$R^7$ is each independently selected from hydrogen atom, hydroxy, halogen, cyano, nitro, alkyl, alkoxy, cycloalkyl, heterocyclyl, aryl, heteroaryl, —$NR^8R^9$, —C(O)$NR^8R^9$, —C(O)$R^6$, —OC(O)$R^6$, —S(O)$_q NR^8R^9$, —$NR^8S(O)_2R^9$ or —$NR^8C(O)R^9$, wherein the alkyl, alkoxy, cycloalkyl, heterocyclyl, aryl or heteroaryl is optionally further substituted by a substituent group selected from hydroxy, halogen, nitro, cyano, alkyl, alkoxy, cycloalkyl, heterocyclyl, aryl, heteroaryl, —$NR^8R^9$, —C(O)$NR^8R^9$, —C(O)$R^6$, —OC(O)$R^6$, —S(O)$_q NR^8R^9$, —$NR^8S(O)_2R^9$ or —$NR^8C(O)R^9$;

$R^6$, $R^8$ and $R^9$ are each independently selected from hydrogen atom, alkyl, —$OR^{12}$, cyano, hydroxy, halogen, cycloalkyl, heterocyclyl, aryl or heteroaryl, wherein the alkyl, cycloalkyl, heterocyclyl, aryl or heteroaryl is optionally further substituted by one or more substituent groups selected from hydroxy, halogen, nitro, cyano, alkyl, alkoxy, cycloalkyl, heterocyclyl, aryl, heteroaryl, —$NR^{10}R^{11}$, —C(O)$NR^{10}R^{11}$, —C(O)$R^{12}$, —C(O)O$R^{12}$ or —$NR^{10}C(O)R^{11}$;

or, $R^8$ and $R^9$, together with the N atom to which they are attached, form a $C_{4-8}$ heterocyclyl, wherein the $C_{4-8}$ heterocycle comprises one or more atoms selected from N, O and S(O)$_q$, and the $C_{4-8}$ heterocycle is optionally further substituted by one or more substituent groups selected from hydroxy, halogen, nitro, cyano, alkyl, alkoxy, cycloalkyl, heterocyclyl, aryl, heteroaryl, =O, —$NR^{10}R^{11}$, —C(O)$NR^{10}R^{11}$, —C(O)$R^{12}$, —C(O)O$R^{12}$ or —$NR^{10}C(O)R^{11}$;

$R^{10}$, $R^{11}$ and $R^{12}$ are each independently selected from hydrogen atom, alkyl, alkenyl, cycloalkyl, heterocyclyl, aryl or heteroaryl, wherein the alkyl, cycloalkyl, heterocyclyl, aryl or heteroaryl is optionally further substituted by one or more substituent groups selected from hydroxy, halogen, nitro, cyano, alkyl, alkoxy, cycloalkyl, heterocyclyl, aryl, heteroaryl, carboxylic acid or carboxylic ester; and q is 0, 1 or 2.

2. The compound according to claim 1, which has a structure of Formula (II):

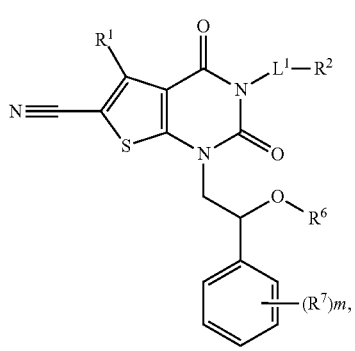

wherein, m is 1, 2, 3, 4 or 5; and $L^1$, $R^1$, $R^2$, $R^6$ and $R^7$ are as defined in claim 1.

3. The compound according to claim 2, which has a structure of Formula (III):

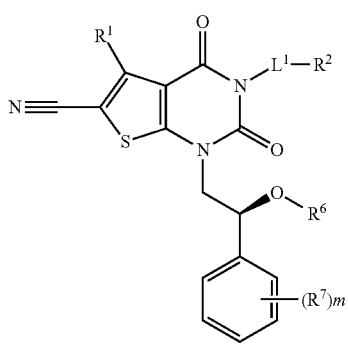

wherein, m is 1, 2, 3, 4 or 5.

4. The compound according to claim 2, which has a structure of Formula (IV):

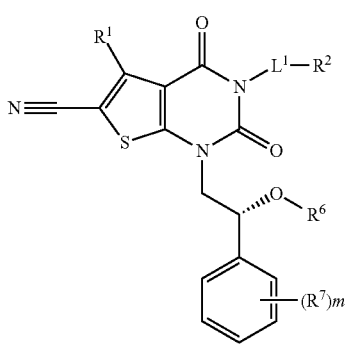

wherein, m is 1, 2, 3, 4 or 5.

5. The compound according to claim 1, wherein $R^1$ is selected from methyl or trifluoromethyl.

6. The compound according to claim 1, wherein:

$R^2$ is selected from tetrazolyl, —C(O)OR$^{12}$ or —C(O)NR$^8$R$^9$;

$R^8$ is selected from hydrogen atom or alkyl;

$R^9$ is selected from cyano or —OR$^{12}$; and $R^{12}$ is selected from hydrogen atom, alkyl, alkenyl, cycloalkyl, heterocyclyl, aryl or heteroaryl, wherein the alkyl, cycloalkyl, heterocyclyl, aryl or heteroaryl is optionally further substituted by one or more substituent groups selected from hydroxy, halogen, nitro, cyano, alkyl, alkoxy, cycloalkyl, heterocyclyl, aryl, heteroaryl, carboxylic acid or carboxylic ester.

7. The compound according to claim 1, wherein $L^1$ is:

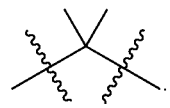 [SMILES: *C(*)(C)C]

8. The compound according to claim 1, wherein $R^6$ is tetrahydropyranyl.

9. The compound according to claim 1, wherein $R^7$ is selected from alkoxy or halogen, wherein the alkoxy is optionally further substituted by halogen or cycloalkyl.

10. The compound according to claim 1, wherein the compound is selected from:

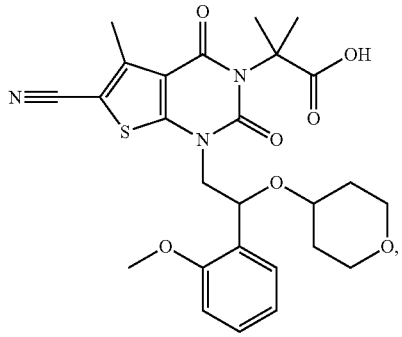

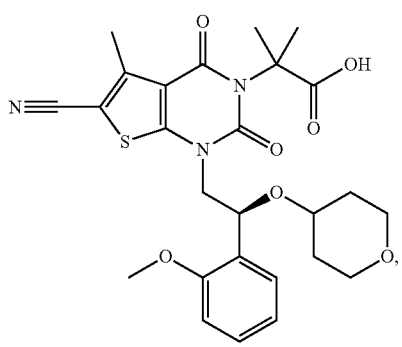

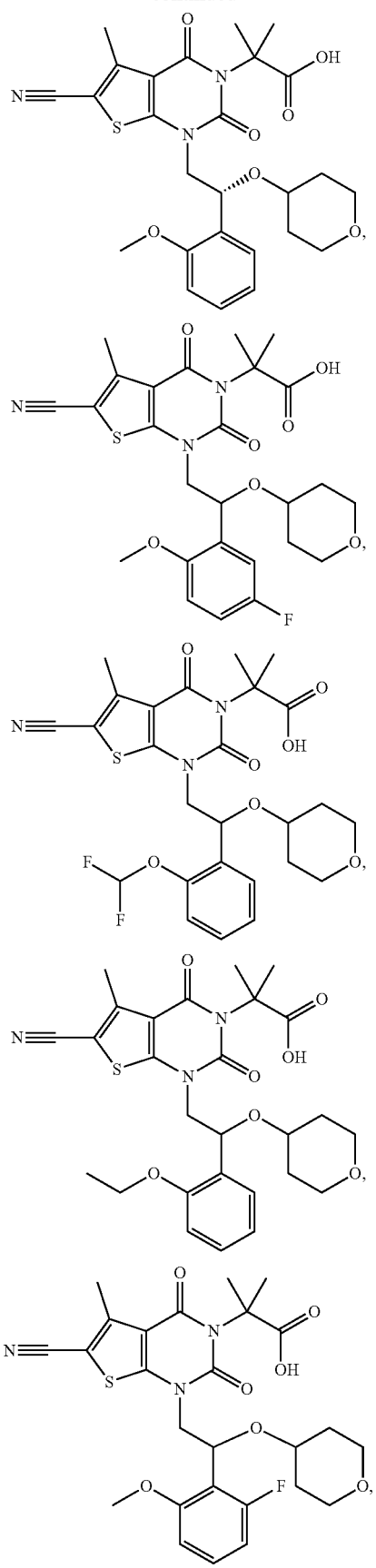
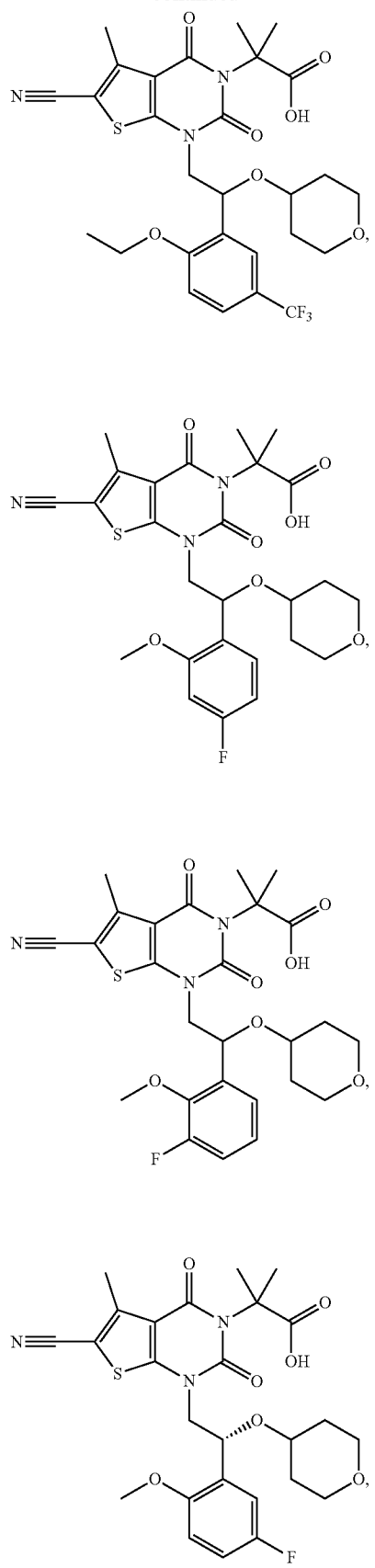

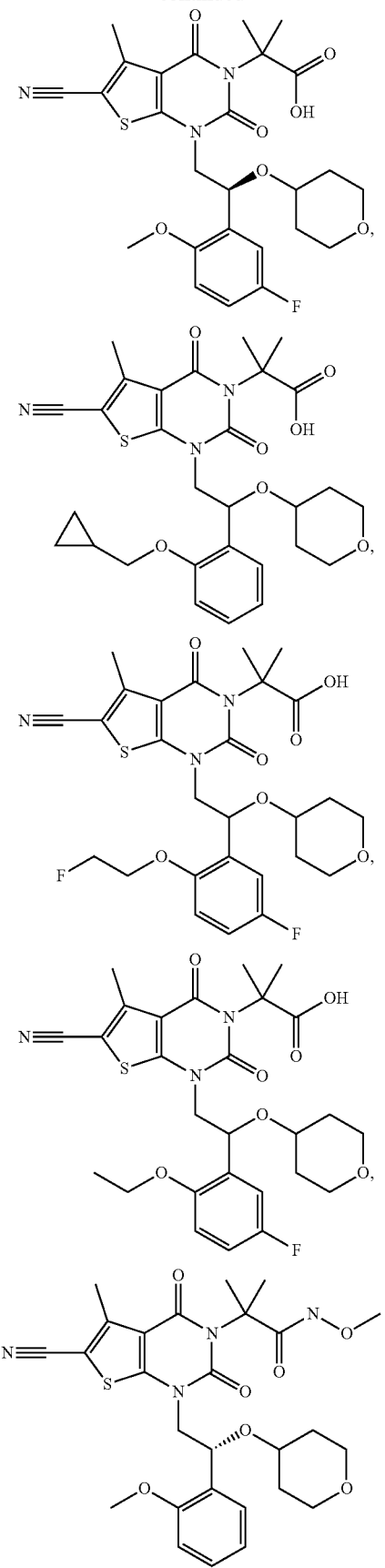
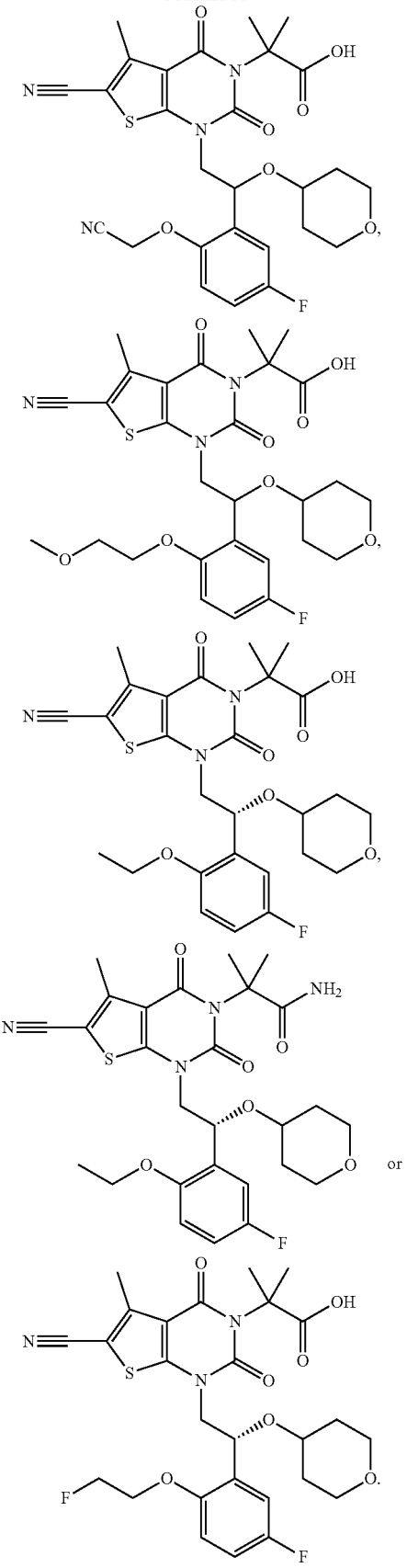

11. A method for preparing the compound of Formula (I) according to claim 1, comprising:

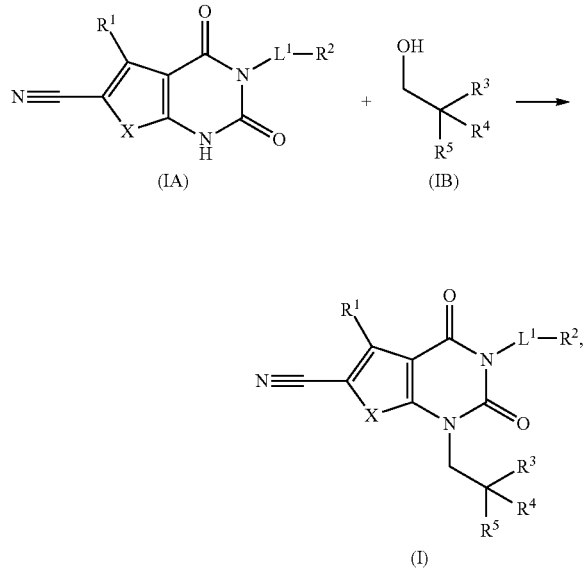

reacting a compound of Formula (IA) with a compound of Formula (IB) or a salt thereof in the presence of triphenylphosphine and diisopropyl azodicarboxylate, optionally further performing esterolysis, or optionally further reacting with NHR⁸R⁹ or a salt thereof, to obtain the compound of Formula (1);
wherein X, L¹, R¹-R⁵, R⁸ and R⁹ are as defined in claim 1; and
R² is —C(O)OH or —C(O)NR⁸R⁹.

12. A compound as shown in Formula (IA)

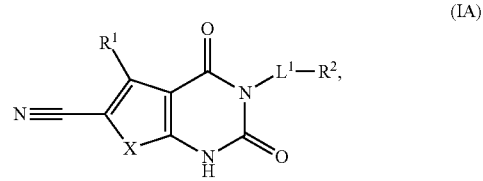

or stereoisomers, tautomers or pharmaceutically acceptable salts thereof,
wherein X, L¹, R¹ and R² are as defined in claim 1.

13. The compound according to claim 12, which is

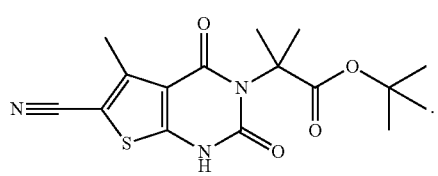

14. A method for preparing the compound of Formula (IA) according to claim 12, comprising:

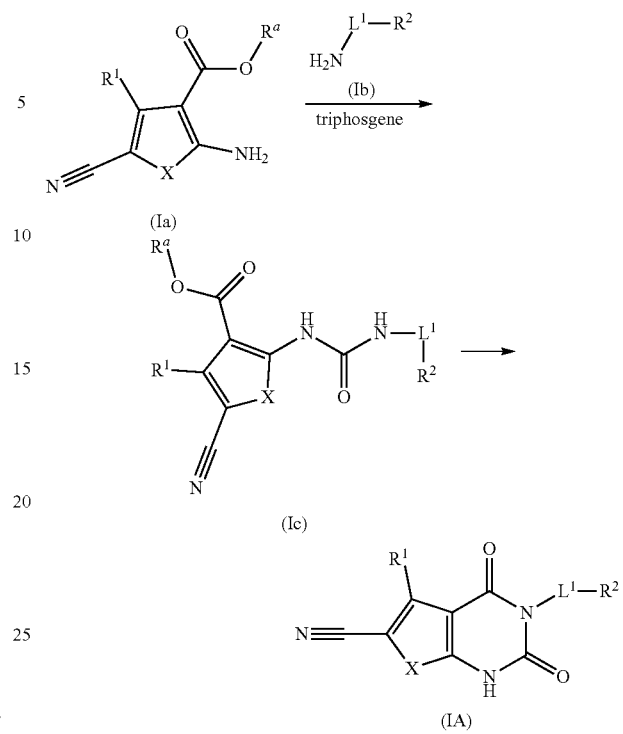

reacting a compound of Formula (Ia) and a compound of Formula (Ib) in the presence of triphosgene under alkaline conditions, to obtain a compound of Formula (Ic); reacting the compound of Formula (Ic) under alkaline conditions to obtain the compound of Formula (IA);
wherein
Rᵃ is selected from alkyl.

15. A pharmaceutical composition, comprising an effective amount of the compound according to claim 1, and optionally a pharmaceutically acceptable carrier, excipient or a combination thereof.

16. A method for inhibiting ACC in a subject in need thereof, comprising administering to the subject a therapeutically effective amount of the compound according to claim 1 or the pharmaceutical composition according to claim 15.

17. A method for treating ACC-related diseases or conditions, comprising administering the compound according to claim 1 or the pharmaceutical composition according to claim 15 to a subject in need thereof.

18. The method according to claim 17, wherein the diseases or conditions are metabolic diseases, cancer, fungus, parasitic or bacterial infection; wherein the metabolic diseases are hepatic steatosis, non-alcoholic fatty liver disease, obesity, dyslipidemia, hyperlipidemia, type II diabetes or metabolic syndrome, wherein the obesity is Prader-Willi syndrome, Bardet-Biedl syndrome, Cohen syndrome or MOMO syndrome, wherein the cancer is hepatocellular carcinoma, non-small cell lung cancer, small cell lung cancer, gastric cancer, colorectal cancer, head and neck tumor, melanoma, ovarian cancer or cervical cancer.

19. The compound according to claim 1, wherein X is —S—.

20. The compound according to claim 9, wherein R⁷ is methoxy, ethoxy, fluoro, difluoromethoxy, fluoroethoxy or cyclopropyl methoxy.

21. The method according to claim 18, wherein the cancer is hepatocellular carcinoma and non-small cell lung cancer.

* * * * *